US007612033B2

(12) United States Patent
Unger et al.

(10) Patent No.: US 7,612,033 B2
(45) Date of Patent: *Nov. 3, 2009

(54) METHODS FOR DELIVERING COMPOUNDS INTO A CELL

(75) Inventors: Evan C. Unger, Tucson, AZ (US); Thomas McCreery, Tucson, AZ (US)

(73) Assignee: ImaRx Pharmaceutical Corp., Tucson, AZ (US)

(*) Notice: Subject to any disclaimer, the term of this patent is extended or adjusted under 35 U.S.C. 154(b) by 407 days.

This patent is subject to a terminal disclaimer.

(21) Appl. No.: 10/802,919

(22) Filed: Mar. 18, 2004

(65) Prior Publication Data

US 2004/0176473 A1 Sep. 9, 2004

Related U.S. Application Data

(60) Division of application No. 08/841,169, filed on Apr. 29, 1997, now Pat. No. 6,743,779, which is a continuation-in-part of application No. 08/785,661, filed on Jan. 17, 1997, now abandoned, which is a continuation-in-part of application No. 08/640,554, filed on May 1, 1996, now abandoned, which is a continuation of application No. 08/346,426, filed on Nov. 29, 1994, now Pat. No. 5,733,572.

(51) Int. Cl.
*A61K 38/00* (2006.01)
*A61K 33/34* (2006.01)

(52) U.S. Cl. .......................... 514/2; 424/632

(58) Field of Classification Search ................... None
See application file for complete search history.

(56) References Cited

U.S. PATENT DOCUMENTS

| 3,015,128 | A |   | 1/1962  | Sommerville et al. ......... 18/2.6 |
|-----------|---|---|---------|-------------------------------------|
| 3,039,929 | A | * | 6/1962  | Stanko                              |
| 3,050,443 | A | * | 8/1962  | Kraus                               |
| 3,073,743 | A | * | 1/1963  | Spero                               |
| 3,138,527 | A | * | 6/1964  | Sprero et al.                       |
| 3,291,843 | A |   | 12/1966 | Fritz et al. ................... 260/614 |
| 3,293,114 | A |   | 12/1966 | Kenaga et al. ............... 162/168 |
| 3,479,811 | A |   | 11/1969 | Walters ........................ 57/153 |
| 3,488,714 | A |   | 1/1970  | Walters et al. ............... 161/161 |
| 3,532,500 | A |   | 10/1970 | Priest et al. ..................... 96/91 |
| 3,557,294 | A |   | 1/1971  | Dear et al. ................... 424/342 |
| 3,594,326 | A |   | 7/1971  | Himmel et al. ............. 252/316 |
| 3,615,972 | A |   | 10/1971 | Morehouse et al. ........... 156/79 |
| 3,650,831 | A |   | 3/1972  | Jungermann et al. ......... 134/27 |
| 3,689,638 | A | * | 9/1972  | Harth et. al. .................. 424/54 |
| 3,732,172 | A |   | 5/1973  | Herbig et al. ............... 252/316 |
| 3,823,229 | A | * | 7/1974  | Jederstrom ................... 424/45 |
| 3,873,564 | A |   | 3/1975  | Schneider et al. ........ 260/309.6 |
| 3,885,028 | A | * | 5/1975  | Cella et al. .................... 424/52 |
| 3,891,757 | A | * | 6/1975  | Higuchi ....................... 514/772 |
| 3,945,956 | A |   | 3/1976  | Garner ..................... 260/2.5 B |
| 3,957,964 | A | * | 5/1976  | Grimm, III ................ 424/10.4 |
| 3,960,583 | A |   | 6/1976  | Netting et al. ............... 106/122 |
| 3,968,203 | A |   | 7/1976  | Spitzer et al. .................. 424/47 |
| 3,989,816 | A | * | 11/1976 | Rajadhyaksha ............... 424/60 |
| 4,027,007 | A |   | 5/1977  | Messina ....................... 424/46 |
| 4,044,126 | A | * | 8/1977  | Cook et al. .................. 424/243 |
| 4,089,801 | A |   | 5/1978  | Schneider ................... 252/316 |
| 4,108,806 | A |   | 8/1978  | Cohrs et al. .................... 521/54 |
| 4,138,383 | A |   | 2/1979  | Rembaum et al. ....... 260/29.7 H |
| 4,152,418 | A | * | 5/1979  | Pader .......................... 424/50 |
| 4,154,815 | A | * | 5/1979  | Pader .......................... 424/50 |
| 4,162,282 | A |   | 7/1979  | Fulwyler et al. ................ 264/9 |
| 4,179,546 | A |   | 12/1979 | Garner et al. .................. 521/56 |
| 4,192,859 | A |   | 3/1980  | Mackaness et al. ............. 424/5 |
| 4,211,771 | A | * | 7/1980  | Witkowski et al. .......... 424/180 |
| 4,224,179 | A |   | 9/1980  | Schneider ................... 252/316 |
| 4,229,360 | A |   | 10/1980 | Schneider et al. ........... 260/403 |
| 4,265,251 | A |   | 5/1981  | Tickner ...................... 128/660 |
| 4,276,885 | A |   | 7/1981  | Tickner et al. .............. 128/660 |
| 4,310,505 | A |   | 1/1982  | Baldeschwieler et al. ....... 424/1 |
| 4,310,506 | A |   | 1/1982  | Baldeschwieler et al. ....... 424/1 |
| 4,315,514 | A |   | 2/1982  | Drewes et al. .............. 128/653 |
| 4,331,654 | A |   | 5/1982  | Morris ......................... 424/38 |
| 4,342,826 | A |   | 8/1982  | Cole ............................. 435/7 |
| 4,344,929 | A |   | 8/1982  | Bonsen et al. ................. 424/15 |
| 4,364,923 | A | * | 12/1982 | Cook et al. .................. 424/243 |

(Continued)

FOREIGN PATENT DOCUMENTS

AU        641363        3/1990

(Continued)

OTHER PUBLICATIONS

Godbey, W.T. at al., "Recent Progress in Gene Delivery Using Non-viral Transfer Complexes", J Control Release 72 (2001), pp. 115-125.

Hawiger J., "Noninvasive Intracellular Delivery of Functional Peptides and Proteins," Curr Opin Chem Biol. 1999, 3:89-94.

Veach et al., Receptor/Transporter-independent Targeting of Functional Peptides Across the Plasma Membrane, J Biol Chem, vol. 279, No. 12, Mar. 19, 2004, pp. 11425-11431.

Nomura et al., "US Contrast Enhancement of Hepatic Tumor with Helium Gas Microbubbles: A Preliminary Repor,t" *Jpn. J. Med. Ultrasonics*, vol. 18, No. 5 (1991) (full English language translation provided).

(Continued)

*Primary Examiner*—Cecilia Tsang
*Assistant Examiner*—Maury Audet
(74) *Attorney, Agent, or Firm*—DLA Piper LLP (US)

(57) ABSTRACT

The present invention is directed, inter alia, to a method for delivering a compound into a cell comprising administering to the cell the compound to be delivered, an organic halide, and/or a carrier. Ultrasound may also be applied, if desired.

12 Claims, 7 Drawing Sheets

U.S. PATENT DOCUMENTS

| | | | |
|---|---|---|---|
| 4,414,209 A * | 11/1983 | Cook et al. ................... 514/180 |
| 4,420,442 A | 12/1983 | Sands ........................... 264/13 |
| 4,421,562 A | 12/1983 | Sands et al. .................... 106/75 |
| 4,426,330 A | 1/1984 | Sears ........................ 260/403 |
| 4,427,649 A | 1/1984 | Dingle et al. ................... 424/38 |
| 4,428,924 A | 1/1984 | Millington ...................... 424/4 |
| 4,442,843 A | 4/1984 | Rasor et al. .................... 128/660 |
| 4,466,442 A | 8/1984 | Hilmann et al. ............. 128/653 |
| 4,485,193 A | 11/1984 | Rubens et al. ................ 521/58 |
| 4,530,360 A | 7/1985 | Duarte .................... 128/419 F |
| 4,533,254 A | 8/1985 | Cook et al. .................. 366/176 |
| 4,534,899 A | 8/1985 | Sears ........................ 260/403 |
| 4,540,629 A | 9/1985 | Sands et al. .................. 428/402 |
| 4,544,545 A | 10/1985 | Ryan et al. .................... 424/1.1 |
| 4,549,892 A | 10/1985 | Baker et al. ................... 65/21.4 |
| 4,569,836 A | 2/1986 | Gordon ........................ 424/1 |
| 4,572,203 A | 2/1986 | Feinstein .................... 128/661 |
| 4,586,512 A | 5/1986 | Do-huu et al. .............. 128/660 |
| 4,603,044 A | 7/1986 | Geho et al. ..................... 424/9 |
| 4,615,879 A | 10/1986 | Runge et al. .................... 424/9 |
| 4,620,546 A | 11/1986 | Aida et al. .................... 128/660 |
| 4,621,023 A | 11/1986 | Redziniak et al. ........ 428/402.2 |
| 4,646,756 A | 3/1987 | Watmough et al. .......... 128/804 |
| 4,657,756 A | 4/1987 | Rasor et al. .................... 424/9 |
| 4,658,828 A | 4/1987 | Dory ............................ 128/660 |
| 4,663,161 A | 5/1987 | Mannino et al. ............... 424/89 |
| 4,675,310 A | 6/1987 | Chapman et al. ................. 514/6 |
| 4,681,119 A | 7/1987 | Rasor et al. .................... 128/660 |
| 4,684,479 A | 8/1987 | D'Arrigo .................... 252/307 |
| 4,689,213 A * | 8/1987 | Golub et al. .................... 424/45 |
| 4,689,986 A | 9/1987 | Carson et al. ................... 73/19 |
| 4,693,999 A | 9/1987 | Axelsson et al. ............ 514/174 |
| 4,718,433 A | 1/1988 | Feinstein .................... 128/660 |
| 4,728,575 A | 3/1988 | Gamble et al. ............ 428/402.2 |
| 4,728,578 A | 3/1988 | Higgins et al. ............. 428/462 |
| 4,731,239 A | 3/1988 | Gordon ........................ 424/9 |
| 4,737,323 A | 4/1988 | Martin et al. ................. 264/4.3 |
| 4,774,958 A | 10/1988 | Feinstein ............... 128/660.01 |
| 4,775,522 A | 10/1988 | Clark, Jr. ........................ 424/9 |
| 4,776,991 A | 10/1988 | Farmer et al. ................ 264/4.3 |
| 4,781,871 A | 11/1988 | West, III et al. .............. 264/4.3 |
| 4,789,501 A | 12/1988 | Day et al. .................... 252/645 |
| 4,790,891 A | 12/1988 | Halliday et al. ................ 149/2 |
| 4,822,534 A | 4/1989 | Lencki et al. ................. 264/4.3 |
| 4,830,858 A | 5/1989 | Payne et al. .................. 424/450 |
| 4,834,964 A | 5/1989 | Rosen ............................ 424/9 |
| 4,844,882 A | 7/1989 | Widder et al. ................... 424/9 |
| 4,845,233 A * | 7/1989 | Higuchi et al. .............. 548/320 |
| 4,863,717 A | 9/1989 | Keana ............................ 424/9 |
| 4,865,836 A | 9/1989 | Long, Jr. ........................ 424/5 |
| 4,877,561 A | 10/1989 | Iga et al. ........................ 264/4.3 |
| 4,893,624 A | 1/1990 | Lele ............................ 128/399 |
| 4,895,719 A | 1/1990 | Radhakrishnan et al. ....... 424/45 |
| 4,898,734 A | 2/1990 | Mathiowitz et al. .......... 424/426 |
| 4,900,540 A | 2/1990 | Ryan et al. ..................... 424/9 |
| 4,918,065 A | 4/1990 | Stindl et al. ................. 514/179 |
| 4,919,895 A | 4/1990 | Heldebrant et al. .......... 422/129 |
| 4,921,706 A | 5/1990 | Roberts et al. ............... 424/450 |
| 4,927,623 A | 5/1990 | Long, Jr. ........................ 424/5 |
| 4,933,121 A | 6/1990 | Law et al. .................... 264/4.3 |
| 4,938,947 A | 7/1990 | Nicolau et al. ................ 424/1.1 |
| 4,957,656 A | 9/1990 | Cerny et al. .................. 252/311 |
| 4,972,002 A | 11/1990 | Volkert ........................ 521/120 |
| 4,981,692 A | 1/1991 | Popescu et al. .............. 424/422 |
| 4,984,573 A | 1/1991 | Leunbach .................... 128/653 |
| 4,985,550 A | 1/1991 | Charpiot et al. ............ 536/18.4 |
| 4,987,154 A | 1/1991 | Long, Jr. ..................... 514/772 |
| 4,993,415 A | 2/1991 | Long ...................... 128/653 A |
| 4,996,041 A | 2/1991 | Arai et al. ..................... 424/9 |
| 5,000,960 A | 3/1991 | Wallach ....................... 424/450 |
| 5,004,611 A | 4/1991 | Leigh ........................ 424/450 |
| 5,008,050 A | 4/1991 | Cullis et al. ................... 264/4.3 |
| 5,008,109 A | 4/1991 | Tin ............................ 424/422 |
| 5,013,556 A | 5/1991 | Woodle et al. .............. 424/450 |
| 5,019,370 A | 5/1991 | Jay et al. ........................ 424/4 |
| 5,045,304 A | 9/1991 | Schneider et al. ............. 424/9 |
| 5,049,388 A | 9/1991 | Knight et al. ............... 424/450 |
| 4,229,360 A | 11/1991 | Schneider et al. ........... 260/403 |
| 5,078,994 A | 1/1992 | Nair et al. .................... 424/501 |
| 5,088,499 A | 2/1992 | Unger ..................... 128/662.2 |
| 5,107,842 A | 4/1992 | Levene et al. .......... 128/662.02 |
| 5,114,703 A | 5/1992 | Wolf et al. ..................... 424/5 |
| 5,123,414 A | 6/1992 | Unger ........................ 128/654 |
| 5,135,000 A | 8/1992 | Akselrod et al. ........ 128/662.02 |
| 5,137,928 A | 8/1992 | Erbel et al. ..................... 521/56 |
| 5,141,738 A | 8/1992 | Rasor et al. .................... 424/2 |
| 5,147,631 A | 9/1992 | Glajch et al. ................... 424/9 |
| 5,149,319 A | 9/1992 | Unger ........................ 604/22 |
| 5,171,755 A | 12/1992 | Kaufman .................... 514/759 |
| 5,186,922 A | 2/1993 | Shell et al. ................... 128/654 |
| 5,190,766 A | 3/1993 | Ishihara ...................... 424/489 |
| 5,190,982 A | 3/1993 | Erbel et al. ..................... 521/56 |
| 5,192,549 A | 3/1993 | Barenolz et al. ............. 424/450 |
| 5,194,188 A | 3/1993 | Guitierrez .................... 264/4.1 |
| 5,194,266 A | 3/1993 | Abra et al. .................... 424/450 |
| 5,195,520 A | 3/1993 | Schlief et al. .......... 128/660.02 |
| 5,196,183 A | 3/1993 | Yudelson et al. ............... 424/9 |
| 5,196,348 A | 3/1993 | Schweighardt et al. ....... 436/173 |
| 5,198,225 A | 3/1993 | Meybeck et al. ............. 424/450 |
| 5,205,287 A | 4/1993 | Erbel et al. .................. 128/632 |
| 5,205,290 A | 4/1993 | Unger ..................... 128/653.4 |
| 5,209,720 A | 5/1993 | Unger ........................ 604/22 |
| 5,213,804 A | 5/1993 | Martin et al. ................. 424/450 |
| 5,215,680 A | 6/1993 | D'Arrigo .................... 252/307 |
| 5,219,538 A | 6/1993 | Henderson et al. ........ 428/402.2 |
| 5,228,446 A | 7/1993 | Unger et al. ........... 128/662.02 |
| 5,230,882 A | 7/1993 | Unger ........................... 424/9 |
| 5,240,694 A * | 8/1993 | Gwaltney ..................... 424/45 |
| 5,247,935 A | 9/1993 | Cline et al. ................ 128/653.2 |
| 5,271,928 A | 12/1993 | Schneider et al. ............... 424/9 |
| 5,276,145 A | 1/1994 | Bottenstein ................ 530/399 |
| 5,281,408 A | 1/1994 | Unger ........................... 424/4 |
| 5,283,255 A | 2/1994 | Levy et al. ................... 514/410 |
| 5,292,523 A * | 3/1994 | Gristina et al. .............. 424/401 |
| 5,305,757 A | 4/1994 | Unger et al. ........... 128/662.02 |
| 5,310,540 A | 5/1994 | Giddey et al. ................... 424/9 |
| 5,315,997 A | 5/1994 | Widder et al. ............. 128/653.3 |
| 5,315,998 A | 5/1994 | Tachibana et al. ....... 128/660.01 |
| 5,316,771 A | 5/1994 | Barenholz et al. ........... 424/450 |
| 5,334,381 A | 8/1994 | Unger ........................... 424/9 |
| 5,339,814 A | 8/1994 | Lasker ..................... 128/653.4 |
| 5,344,930 A | 9/1994 | Riess et al. ..................... 544/84 |
| 5,350,571 A | 9/1994 | Kaufman et al. ............... 424/9 |
| 5,352,435 A | 10/1994 | Unger ........................... 424/9 |
| 5,354,549 A | 10/1994 | Klaveness et al. ............. 424/3 |
| 5,358,702 A | 10/1994 | Unger ........................... 424/9 |
| 5,362,477 A | 11/1994 | Moore et al. ................... 424/9 |
| 5,362,478 A | 11/1994 | Desai et al. .................... 424/9 |
| 5,380,411 A | 1/1995 | Schlief .................. 204/157.15 |
| 5,380,519 A | 1/1995 | Schneider et al. ............... 424/9 |
| 5,393,524 A | 2/1995 | Quay ............................. 424/9 |
| 5,409,688 A | 4/1995 | Quay ............................. 424/9 |
| 5,410,516 A | 4/1995 | Uhlendorf et al. .............. 367/7 |
| 5,413,774 A | 5/1995 | Schneider et al. .......... 424/9.51 |
| 5,425,366 A | 6/1995 | Reinhardt et al. ....... 128/662.02 |
| 5,433,204 A | 7/1995 | Olson ..................... 128/661.08 |
| 5,445,813 A | 8/1995 | Schneider et al. .......... 424/9.51 |
| 5,456,900 A | 10/1995 | Unger ......................... 424/9.4 |
| 5,460,900 A | 10/1995 | Walters ....................... 424/9.6 |
| 5,469,854 A | 11/1995 | Unger et al. ........... 128/662.02 |
| 5,470,582 A | 11/1995 | Supersaxo et al. ........... 424/489 |
| 5,485,839 A | 1/1996 | Aida et al. ................. 128/653.1 |
| 5,487,390 A | 1/1996 | Cohen et al. ............ 128/662.02 |
| 5,496,535 A | 3/1996 | Kirkland ................... 424/9.37 |

| Patent No. | Date | Inventor | Class |
|---|---|---|---|
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,512,268 A | 4/1996 | Grinstaff et al. | 424/9.322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,532,108 A | 7/1996 | Vogelstein | 435/240.2 |
| 5,536,489 A | 7/1996 | Lohrmann et al. | 424/9.52 |
| 5,536,490 A | 7/1996 | Klaveness et al. | 424/9.52 |
| 5,539,094 A | 7/1996 | Reed et al. | 536/23.5 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,550,289 A | 8/1996 | Eppstein et al. | |
| 5,552,133 A | 9/1996 | Lambert et al. | 424/9.52 |
| 5,552,155 A | 9/1996 | Bailey et al. | 424/450 |
| 5,555,664 A * | 9/1996 | Sarzaud et al. | 604/890 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,892 A | 10/1996 | Kirk et al. | 423/555 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.51 |
| 5,567,414 A | 10/1996 | Schneider et al. | 424/9.52 |
| 5,567,415 A | 10/1996 | Porter | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,057 A | 3/1997 | Lanza et al. | 424/450 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,639,443 A | 6/1997 | Schutt et al. | 424/9.52 |
| 5,639,473 A | 6/1997 | Grinstaff et al. | 424/450 |
| 5,643,553 A | 7/1997 | Schneider et al. | 424/9.52 |
| 5,648,095 A | 7/1997 | Illum et al. | 424/489 |
| 5,648,098 A | 7/1997 | Porter | 424/490 |
| 5,656,611 A | 8/1997 | Kabanov et al. | |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |
| 5,686,060 A | 11/1997 | Schneider et al. | 424/9.52 |
| 5,686,102 A | 11/1997 | Gross et al. | 424/450 |
| 5,695,460 A | 12/1997 | Siegel et al. | 604/21 |
| 5,701,899 A | 12/1997 | Porter | 428/662.02 |
| 5,705,187 A | 1/1998 | Unger | |
| 5,707,352 A | 1/1998 | Sekins et al. | 604/56 |
| 5,707,606 A | 1/1998 | Quay | 424/9.52 |
| 5,707,607 A | 1/1998 | Quay | 424/9.52 |
| 5,711,933 A | 1/1998 | Bichon et al. | 424/9.52 |
| 5,716,597 A | 2/1998 | Lohrmann et al. | 424/9.5 |
| 5,732,707 A | 3/1998 | Widder et al. | 128/661.08 |
| 5,733,527 A | 3/1998 | Schutt | 424/9.52 |
| 5,736,121 A | 4/1998 | Unger | 424/9.4 |
| 5,740,807 A | 4/1998 | Porter | 128/662.02 |
| 5,770,222 A | 6/1998 | Unger et al. | |
| 5,773,024 A | 6/1998 | Unger et al. | |
| 5,804,162 A | 9/1998 | Kabalnov et al. | 424/9.51 |
| 5,830,430 A | 11/1998 | Unger et al. | |
| 5,840,023 A | 11/1998 | Oraevsky et al. | 600/407 |
| 5,846,517 A | 12/1998 | Unger et al. | |
| 5,849,727 A | 12/1998 | Porter et al. | 514/156 |
| 5,855,865 A | 1/1999 | Lambert et al. | 424/9.52 |
| 5,858,399 A | 1/1999 | Lanza et al. | 424/450 |
| 5,874,062 A | 2/1999 | Unger | 424/9.4 |
| 5,897,851 A | 4/1999 | Quay et al. | 424/9.52 |
| 5,976,501 A | 11/1999 | Jablonski | 424/9.52 |
| 5,997,898 A | 12/1999 | Unger | |
| 6,033,645 A | 3/2000 | Unger et al. | |
| 6,056,938 A | 5/2000 | Unger et al. | 424/1.21 |
| 6,068,857 A | 5/2000 | Weitschies et al. | 424/489 |
| 6,088,613 A | 7/2000 | Unger | |
| 6,123,923 A | 9/2000 | Unger et al. | |
| 6,139,819 A | 10/2000 | Unger et al. | |
| 6,143,276 A | 11/2000 | Unger | |
| 6,159,445 A | 12/2000 | Klaveness et al. | 424/9.6 |
| 6,261,537 B1 | 7/2001 | Klaveness et al. | 424/9.52 |
| 6,331,289 B1 | 12/2001 | Klaveness et al. | 424/9.52 |
| 6,403,056 B1 | 6/2002 | Unger | |
| 6,414,439 B1 | 7/2002 | Unger et al. | |
| 6,436,368 B1 * | 8/2002 | Love et al. | 424/46 |
| 6,638,767 B2 * | 10/2003 | Unger et al. | 435/458 |
| 6,743,779 B1 | 6/2004 | Unger et al. | |

FOREIGN PATENT DOCUMENTS

| | | |
|---|---|---|
| AU | B-30351/89 | 3/1993 |
| DE | 25 21 003 | 8/1976 |
| DE | 3803972 | 8/1989 |
| DE | 195 41 679 A1 | 5/1997 |
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 224 934 | 6/1987 |
| EP | 0 231 091 | 8/1987 |
| EP | 0 272 091 | 6/1988 |
| EP | 0 320 433 A2 | 12/1988 |
| EP | 0 324 938 | 7/1989 |
| EP | 0 338 971 | 10/1989 |
| EP | 0 359 246 | 3/1990 |
| EP | 357163 A1 | 3/1990 |
| EP | 0 361 894 | 4/1990 |
| EP | 0 216 730 | 1/1991 |
| EP | 0 467 031 A2 | 5/1991 |
| EP | 441468 A2 | 8/1991 |
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 633 030 A1 | 1/1995 |
| EP | 0 727 225 A2 | 8/1996 |
| EP | 0 901 793 A1 | 3/1999 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | 85/01161 | 3/1985 |
| WO | WO 85/02772 | 7/1985 |
| WO | WO 86/00238 | 1/1986 |

| | | |
|---|---|---|
| WO | WO 86/01103 | 2/1986 |
| WO | WO 89/02464 | 3/1989 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/00086 | 1/1991 |
| WO | WO 91/03267 | 3/1991 |
| WO | WO 91/09629 | 7/1991 |
| WO | WO 91/12823 | 9/1991 |
| WO | WO 91/15244 | 10/1991 |
| WO | WO 91/18612 | 12/1991 |
| WO | 92/05806 | 4/1992 |
| WO | WO 92/10166 | 6/1992 |
| WO | WO 92/11873 | 7/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/19768 | 10/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 95/32006 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 96/40285 | 12/1996 |
| WO | WO 98/00172 | 1/1998 |
| WO | WO 98/04292 | 2/1998 |
| WO | WO 99/13919 | 3/1999 |

OTHER PUBLICATIONS

Porter, et al., "Multifold Sonicated Dilutions of Albumin with Fifty Percent Dextrose Improve Left Ventricular Contrast Videointensity After Intravenous Injection in Human Beings," *Journal of the American Society of Echocardiography*, vol. 7, No. 5, pp. 465-471, Sep.-Oct. 1994.

Porter, et al., "Noninvasive Identification of Acute Myocardial Ischemia and Reperfusion With Contrast Ultrasound Using Intravenous Perfluorpropane-Exposed Sonicated Dextrose Albumin," *Journal of the American College of Cardiology*, vol. 26, No. 1, pp. 33-40; 1995.

Porter, et al., "Visually Discernible Myocardial Echocardiographic Contrast After Intravenous Injection of Sonicated Dextrose Albumin Microbubbles Containing High Molecular Weight, Less Soluble Gases," *Journal of the American College of Cardiology*, vol. 25, No. 2, pp. 509-515, Feb. 1995.

Srinivasan, et al., "Characterization of Binding Sites, Extent of Binding, and Drug Interactions of Oligonucleotides with Albumin," *Antisense Research and Development*, vol. 5, pp. 131-139, 1995.

Xie, et al., "Acute Myocardial Ischemia and Reperfusion can be Visually Identified Non-invasively with Intravenous Perfluoropropane-Enhanced Sonicated Dextrose Albumin Ultrasound Contrast," *Circulation*, vol. 90, No. 4, Part 2, Abstract 2989, Oct. 1994.

Frezard, F. et al., "Fluorinated phosphatidylcholine-based liposomes: H+/Na+ permeability, active doxorubican encapsulation and stbility in human serum" *Biochim et Biophys Acta*, 1994, vol. 1194 (1), pp. 61-68.

Gross, U. et al., "Phospholipid vesiculated fluorocarbons promising trend in blood substitutes" *Biomat., Art. Cells & Immob. Biotech.*, 1992, vol. 20, (2-4) pp. 831-833.

Riess, Jean G., "Fluorine in our arteries", *New J. Chem.*, 1995, vol. 19 (8-9), pp. 891-909 (English Abstract).

Riess, Jean G., "Introducing a new element fluorine-into the liposomal membrane" *Journal of Liposome Research*, 1995, vol. 5 (3) pp. 413-430.

Santaella, C. et al., "Extended in vivo blood circulation time of fluorinated liposomes" *FEBS Letters*, 1993, vol. 336(3), pp. 481-484.

Trevino, L, et al., "Incorporation of a perfluroalkylalkane (rfrh) into the phospholipid bilayer of dmpc liposomes results in greater encapsulation stability", *Journal of Liposome Research.*, 1994, vol. 4 (2) pp. 1017-1028.

Zarif L. et al., "Biodistribution and excretion of a mixed flurocarbon-hydrocarbon "dowel" emulsion as determined by 19-F NMR", *Artificial Cells, Blood Substitutes, and Immobilization Biotechnology*, 1994, vol. 22,(4) pp. 1193-1198.

Trevedi and Dickson (1995) "Liposome-mediated gene transfer into normal and dystrophin-deficient mouse myoblasts" *J. Neurochem* 64(5):2230-8 (Abstract only).

Watson, A.J. (1995) "Review article: manipulation of cell death—the development of novel strategies for the treatment of gastrointestinal disease" *Aliment. Pharmacol. Ther.* 9(3):215-26 (Abstract only).

Yla-Herttuala (1996) "Gene therapy for cardiovascular diseases" *Ann. Med.* 28(2):89-93 (Abstract only).

Zabner (1996) "Repeat administration of an adenovirus vector encoding cystic fibrosis transmembrane conductance regulator to the nasal epithelium of patients with cystic fibrosis" *Clin. Invest.* 97(6):1504-1511.

Porter, T. R., et al., "Thrombolytic Enhancement with Perfluorocarbon-exposed Sonicated Dextrose Albumin Microbubbles", *American Heart Journal*, Nov. 1996, vol. 132, No. 5, pp. 964-968.

Kinsler, L. E., et al., *Fundamentals of Acoustics*, $3^{rd}$ Ed., 1982, 228-331.

Meessen, H. (ed.), *Microcirculation*, Springer-Verlag, Berlin Heidelberg, New York, 1997, 44.

Ring, J., et al., "Humanalbuminunverträglichkeit: klinische und inununologische untersuchungen," *Clinical Weekly*, 1974, 52, 595-598 (Abstract-English).

Robinson, et al., F.J. Fry (ed.), "Ultrasound: its applications in medicine and biology," *Elsevier Scientific Publishing Company*, 1978, vol. 3, Chap. XI, 593-596.

Silbernagl, S., et al., "Pocket atlas of physiology," *Georg Thieme Verlag*, Stuttgart, New York, 1983, 156-157.

Wells, P.N.T., "Pulse-echo methods," *Biomedical Ultrasonics*, Academic Press, 1977, 209-216.

Ding, X.C., et al., "Scavenging effect of EDTA-fluorocarbon microspheres on $^{210}$ lead," *Chung Kuo Yao Li Hsueh Pao* 1989, 10(5):473-475. (Abstract).

Chortkoff, B.S. et al., "Pharmacokinetics Do Not Explain the Absence of an Anesthetic Effect of Perfluoropropane or Perfluoropentane," *Anesth. Analog.*, 1994, 79, 234-237.

Sharma, S.K. et al., "Emulsifcation Methods for Perfluorochemicals;" *Drug Devel. Indust. Pharmacy*, 1988, 14(15-17), 2371-2376.

Tilcock, C. et al., "PEG-coated Lipid Vesicles with Encapsulated Technetium-99m as Blood Pool Agents for Nuclear Medicine," *Nucl. Med. Biol.*, 1994, 2, 165-170.

Tilcock, C. et al., "$^{99m}$Tc-labeling of Lipid Vesicles Containing the Lipophilic Chelator PE-DTTA: Effect of Tin-to-chelate Ratio, Chelate Content and Surface Polymer on Labeling Efficiency and Biodistribution Behavior," *Nucl. Med. Biol.*, 1994, 1, 89-96.

Zarif, L. et al., "Synergistic Stabilization of Perfluorocarbon-Pluronic F-68 Emulsion by Perfluoroalkylated Polyhydroxylated Surfactants," *JAOCS*, 1989, 66(10), 1515-1523.

Jackson, B.A. et al., "Effect of ultrasound therapy on the repair of Achilles tendon injuries in rats", *Med & Sci. In Sports & Exercise*, 1991, 23(2), 171-176.

Lejbkowicz, F. et al., "The response of normal and malignant cells to ultrasound in vitro", *Ultrasound Med. Biol.*, 1993, 19(1), 75-82 (abstract only).

Maxwell, L., "Therapeutic Ultrasound: Its Effects on the Cellular and Molecular Mechanisms of Inflammation and Repair", *Physiotherapy*, 1992, 78(6), 421-426.

Tuncay, O. et at, "Expression of Genes Associated with Tissue Remodeling Upon Ultrasound Perturbation in the Gingival Fibroblast", *J. Dental Res.*, 1996, 14, 143, Abstract No. 1007.

Wang, S-J. et al., "Low Intensity Ultrasound Treatment Increases Strength in a Rat Femoral Fracture Model", *J. Orthopaedic Res.*, 1994, 12, 40-47.

Yang, K-H. et al., "Exposure to Low-Intensity Ultrasound Increases Aggrecan Gene Expression in a Rat Femur Fracture Model", *J. Orthopaedic Res.*, 1996, 14, 802-809.

Young, S.R. et al., "The Effect of Therapeutic Ultrasound on Angiogenesis", *Ultrasound in Med. & Biol.*, 1990, 16(3), 261-269.

Young, S.R. et al., "Effect of therapeutic ultrasound on the healing of full-thickness excised skin leasons", *Ultrasonics*, 1990, 28(3), 175-180.

Hynynen et al., "The Usefulness of a Contrast Agent and Gradient Recalled Acquisition in a Steady-State Imaging Sequence for Magnetic Resonance Imaging-Guided Noninvasive Ultrasound Surgery", *Investigative Radiology*, 1994, 29(10), 897-903.

Hautanen, A., et al., "Effects of modifications of the RGD sequence and its context on recognition by the fibronectin receptor," *J Biol. Chem.*, 1989, 264(3), 1437-1442.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP-000952675.

Unger, E.C., et al., "In vitrostudies of a new thrombus-specific ultrasound contrast agent," *J. of Cardiology*, 1998, 81(12), 58G-61G, Abstract XP-002087505.

Wu, Y., et al., "Binding and lysing of blood clots using MRX-408," *Investigate Radiology*, 1998, 33(12), 880-885.

Lindner et al., "Myocardial Perfusion Characteristics and Hemodynamic Profile of MRX-115, a Venous Echocardiographic Contrast Agent, During Acute Myocardial Infarction", *J. Am. Soc. Echocardiography*, 1998, 11(1), 36-46.

Regen et al., "Polymerized Phosphatidylcholine Vesicles. Synthesis and Characterization", *J. Am. Chem. Soc.*, 1982, 104(3), 191-195.

Wei et al., "Quantification of Myocardial Blood Flow with Ultrasound-Induced Destruction of Microbubbles Administered as a Constant Venous Infusion", *Circulation*, 1998, 97, 473-483.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Reexamination of U.S. Patent No. 5,527,521, issued May 16, 2003, Reexam Control No. 90/004,719.

Reexamination of U.S. Patent No. 5,547,656, issued Sep. 13, 2000, Reexam Control No. 90/004,720.

Desir et al., "Assessment of regional myocardial perfusion with myocardial contrast echocardiography in a canine model of varying degrees of coronary stenosis", *Am. Heart J.*, Jan. 1994, 127(1), 56-63.

Sekins et al., "Lung Cancer Hyperthermia via Ultrasound and PFC Liquids", *Published in Proceedings of 5th International Symposium on Hyperthermic Oncology*, Kyoto, Japan, Aug. 29-Sep. 3, 1998, 3 pages.

Pietersen, "A New Warning System for Fires of Electrical Origin", *CERN European Organization for Nuclear Research, Health and Safety Division*, Mar. 1977, 1-5.

Villanueva et al., "Characterization of Spatial Patters of Flow Within the Reperfused Myocardium by Myocardial Contrast Echocardiography", *Circulation*, vol. 88, No. 6, pp. 2596-2606 (Dec. 1993).

Nabel et al., "Combined Experience from Phase I Studies with Allovectin-7, a Direct Gene Transfer Immunotherapeutic in Patients with Metastatic Solid Tumors", *Proceed. ASCO*, Mar. 14, 1995, 14, 226, (31st Annual Meeting of the American Society of Clinical Oncology, May 20-23, 1995) (Abstract No. 582).

Rubin et al., "Phase I Study of Immunotherapy of Hepatic Metastasis of Colorectal Carcinoma by Direct Gene Transfer", *Proceed. ASCO*, Mar. 14, 1995, 14, 228, (31st Annual Meeting of the American Society of Clinical Oncology, May 20-23, 1995) (Abstract No. 589).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568-574 (1974).

Thanassi, "Aminomalonic Acid: Spontaneous Decarboxy-lation and Reaction with 5-Deoxypyridoxal", *Bio-chemistry*, vol. 9, No. 3, pp. 525-532 (1970).

Stelmashok et al., *Koordinatsionnaya Khimiya*, vol. 3, No. 4, pp. 524-527 (1977) (Russian and English language versions).

Mayhew et al., "High-Pressure Continuous-Flow System for Drug Entrapment in Liposomes", *Methods in Enzymology*, vol. 149, pp. 64-77 (1987).

Mayhew et al., "Characterization of Liposomes Prepared Using a Microemulsifier", *Biochimica et Biophysica Acta*, vol. 775, pp. 169-174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55-65 (1985).

Mayer et al., "Vesicles of Variable Size Produced by a Rapid Extrusion Procedure", *Biochimica et Biophysica Acta*, vol. 858, pp. 161-168 (1986).

Cheng, et al., "The Production and Evaluation of Contrast-Carrying Liposomes Made with an Automatic High Pressure System", *Investigative Radiology*, vol. 22, pp. 47-55 (1987).

Jain, et al., *Introduction to Biological Membranes*, Ch. 9, pp. 192-231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Longchain Saturated Phosphatidylcholines by Extrusion Technique", *Biochimica et Biophysica Acta*, vol. 986, pp. 200-206 (1989).

Hope et al., "Generation of Multilamellar and Unilamellar Phospholipid Vesicles", *Chemistry and Physics of Lipids*, vol. 40, pp. 89-107 (1986).

Mattrey et al., "Perfluorochemicals as US Contrast Agents for Tumor-Imaging and Hepatosplenography: Preliminary Clinical Results", *Radiology*, vol. 163, pp. 339-343 (1987).

Mattrey et al., "Perfluoroctylbromide: A Liver/Spleen-Specific and Tumor Imaging Ultrasound Contrast Material", *Radiology*, vol. 145, pp. 759-762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570-575 (1987).

Feinstein et al., "Two-Dimensional Contrast Echocar-diography, I: In Vitro Development and Quantitative Analysis of Echo Contrast Agents", *JACC*, vol. 3, No. 1, pp. 14-20 (1984).

Ten Cate et al., "Two-Dimensional Contrast Echocar-diography, II: Transpulmonary Studies", *JACC*, vol. 3, No. 1, pp. 21-27 (1984).

Unger et al., "Hepatic Metastases: Liposomal Gd-DTPA-enhanced MR Imaging", *Radiology*, vol. 171, pp. 81-85 (1989).

Deamer et al., "Permeability of Lipid Bilayers to Water and Ionic Solutes", *Chemistry and Physics of Lipids*, vol. 40, pp. 167-188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789-797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193-198 (1980).

Tilcock et al., "Liposomal Gd-DTPA: Preparation and Characterization of Relaxivity", *Radiology*, vol. 171, pp. 77-80 (1989).

Mann et al., "Formation of Iron Oxides in Unilamellar Vesicles", *Journal of Colloid and Interface Science*, vol. 122, No. 2, pp. 326-335 (1988).

Anderson et al., "Manganese (III) Complexes in Oxidative Decarboxylation of Acids", *J. Am. Chem. Soc.*, vol. 92, 2450-2460 (1970).

Muhlradt et al., "Vitamin B6 Analogs: An Improved Synthesis of 5-Deoxypyridoxal", *New Compounds*, vol. 10, pp. 129-130 (1967).

Chapman D., "Physiochemical Properties of Phospholipids and Lipid Water Systems", *Liposome Technology*, Gregoriadis, G., ed., vol. 1, pp. 1-19 (CRC Press, Boca Raton, FL, 1984).

Violante et al., "Particulate Suspensions as Ultrasonic Contrast Agents for Liver and Spleen", *Inv. Rad.*, vol. 23, pp. S294-S297, Sep. 1988.

Fritzsch et al., "Preclinical and Clinical Results with an Ultrasonic Contrast Agent", *Inv. Rad.*, vol. 23, pp. S302-S305, Sep. 1988.

Brochure, *Experience*, Sonicator™, Heat Systems-Ultrasonics, Inc. (1987).

M. Ostro, "Liposomes", Marcel Dekker, New York, pp. 102-103 (1983).

Fukuda et al., "Polymer-Encased Vesicles Derived from Diotadecyldimethylammonium Methacrylate", *J. Am. Chem. Soc.*, vol. 108, pp. 2321-2327 (1986).

Regen, "Polymerized Vesicles", *J. Am. Chem. Soc.*, vol. 102, pp. 6638-6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322-326 (1981) (abstract).

J. Vion-Dury et al., *J. Pharmacol. Exper. Ther.*, vol. 250(3), pp. 1113-1118 (1989) (abstract).

M.R. Zalutsky et al., *Invest. Radiol.*, vol. 22(2), pp. 141-147 (1987) (abstract).

Crowe et al., *Archives of Biochemistry and Biophysics*, vol. 242, pp. 240-247 (1985).

Crowe et al., *Archives of Biochemistry and Biophysics*, vol. 220, pp. 477-484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1-18, 29-35, 51-65 and 79-107 (CRC Press Inc., Boca Raton, FL, (1984).

Madden et al., *Chemistry and Physics of Lipids*, vol. 53, pp. 37-46 (1990).

Sinkula et al., *J. Pharm. Sci.*, vol. 64, pp. 181-210 (1975).

Shiina et al., "Hyperthermiaby Low-frequency Synthesized Ultrasound", *IEEE Engineering*, pp. 879-880, vol. 2 (1988) (abstract).

McAvoy et al., *IEEE Engineering, Ultrasonics Symposium Proceedings*, vol. 2, pp. 677-1248 (1989) (abstract).

Chapman et al., "Biomembrane Phase Transitions", *J. Biol. Chem.*, 1974, 249:2512-2521.

Hug et al., "Liposomes for the Transformation of Eukaryotic Cells", *Biochimica et Biophysica Acta*, 1991, 1097:1-17.

Marsh, *CRC Handbook of Lipid Bilayers* (CRC Press, Boca Raton, FL 1990) pp. 139-141.

Szoka et al., "Procedure for Preparation of Liposomes With Large Internal Aqueous Space . . . ", *Proc. Natl. Acad. Sci.* 1978, 75:4194-4198.

Acoustic Imaging; AI5200; Convex Curved Linear Array Ultrasound Transducers Operator's Manual, Nov. 20, 1989, 4700-0003-1C, p. 4.

Bangham et al., "Diffusion of Univalent Ions across the Lamellae of Swollen Phospholipids", *J. Mol. Biol.*, 1965, 13:238-252.

Carson et al., *Ultrasound in Med. & Biol. 3*, 1978, 341-350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387-396 (1985).

deGier et al., "Relations Between Liposomes and Biomembranes", *Annals of the New York Academy of Sciences*, 1978, 308:85-99.

Felgner et al., "Lipofection: A highly efficient, lipid-mediated DNA-transfection procedure", *Proc. Natl. Acad. Sci.*, 1987, 84:7413-7417.

Gabizon et al., "Liposome formulations with prolonged circulation time in blood and enhanced uptake by tumors", *Proc. Natl. Acad. Sci.*, 1988, 85:6949-6953.

Garelli, et al., *Biochimica et Biophysica Acta*, vol. 1127:41-48 (1992).

Kawai et al., "New Procedure for DNA Transfection with Polycation and Dimethyl Sulfoxide", *Molecular and Cellular Biology*, 1984, 4:1172-1174.

Kuo et al., "Metallocene Antitumor Agents. Solution and Solid-State Molybdenocene Coordination . . . ", *J. Am. Chem. Soc.*, 1991, 113:9027-9045.

*Mammalian Cell Biotechnology: A Practical Approach*, M. Butler, 1991 (Oxford University Press, New York), p. 57-70.

Mathiowitz et al., "Photochemical Rupture of Microcapsules: A Model System", *Journal of Applied Polymer Science*, 1981, 26:809-822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277-336.

Sato et al., "Recent Aspects in the Use of Liposomes in Biotechnology and Medicine", *Prog. Lipid Res.* 1992, 4:345-372.

Simons et al., "Antisense c-myb oligonucleotides inhibit intimal arterial smooth muscle cell accumulation in vivo", *Nature*, 1992, 359:67-70.

Thompson, Larry, "At Age 2, Gene Therapy Enters a Growth Phase", *Science* 1992, 258:744-746.

Trubetskoy et al. "Cationic liposomes enhance targeted delivery and expression of exogenous DNA . . . ", Biochimica et Biophysica Acta 1992, 131:311-313.

Umemura et al., "Studies on Sonodynamic Cancer Therapy", *IEEE*, 1992, O-7803-0785, pp. 354-355.

Williams, "Human Gene Therapy: Searching for Better Vectors", *ASM News* [American Society for Microbology] 1992, 58:67-69.

Woodle et al., "Versatility in lipid compositions showing prolonged circulation . . . ", *Biochimica et Biophysica Acta* 1992, 1105:193-200.

Zhou et al., "Targeted delivery of DNA by liposomes and polymers", *J. of Controlled Release* 1992, 19:269-274.

Mathiowitz et al., "Polyanhydride Microspheres as Drug Carriers", *Journal of Applied Polymer Science*, vol. 35, pp. 755-774 (1988).

Sankaram et al., "Cholesterol-Induced Fluid-Phase Immiscibility in Membranes", *Proc. Natl. Acad. Sci.*, vol. 88, pp. 8686-8690 (1991).

*Scientific Apparatus Catalog 92/93* (VWR Scientific, 1991), "Syringes", pp. 1511-1513; "Filtration, Syringe Filters", pp. 766-768; "Filtration, Membranes", pp. 750-753; "Filtration, Filter Holders", p. 744.

Gramiak et al., *Radiology*, "Detection of Intracardiac Blood Flow by Pulsed Echo-Ranging", pp. 415-418 (1971).

Feigenbaum et al., *Circulation*, "Identification of Ultrasound Echoes from the Left Ventricle by Use of Intracardiac Injections of Indocyanine Green", vol. XL1, pp. 615-621 (1970).

Santaella, et al., *FEBS 13463*, "Extended In Vivo Blood Circulation Time of Fluorinated Liposomes", vol. 336, No. 3, pp. 481-484 (1993).

Brown and Langer, *Annual Review Medicine*, 1988, 39:221 29, Annual Review, Inc., "Transdermal Delivery of Drugs", pp. 221-229.

Moseley, et al., *Microbubbles: A Novel MR Susceptibility Contrast Agent*, abstract, 1991 Napa, California Meeting of the Society for Magnetic Resonance in Medicine.

Ter-Pogossia *Tomography*, Kee, et al., n, "Physical Principles and Instrumentation", *Computed Body* eds., Raven Press, New York, Chapter 1, pp. 1-7 (1988).

Aronberg, "Techniques", *Computed Body Tomography*, Kee, et al., eds., Raven Press, New York, Chapter 2, pp. 9-36.

Miller, *Ultrasonics* (Sep. 1981), "Ultrasonic detection of resonant cavitation bubbles in a flow tube by their second-harmonic emissions," pp. 217-224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography-Tissue Imaging & Quantification of Coronary Blood Flow", *The Second Annual International Symposium on Contrast Agents in Diagnostic Ultrasound*, Atlantic City, NJ (May 7, 1996) (abstract).

Keown, W. et al., "Methods for Introducing DNA into Mammalian Cells", *Methods in Enzymology* vol. 185 "Gene Expression Technology", Goeddel, D., ed., Academic Press, Inc., New York, 1991, pp. 527-537.

Wyber, J.A. et al., "The Introduction of Macromolecules into Cells Using Ultrasound", *Pharmaceutical Research* Sep. 1995 (Supplement), 12(9), S-96, Biotec 2069.

"Imarx' Ultrasound Agent Ready for Phase II Trials", *Clinica World Medical Device News* Jun. 26, 1995, p. 17.

Tischer et al., "The Human Gene for Vascular Endothelial Growth Factor", *J. Biol. Chem.*, 1991, 266(18), 11947-11954.

Siegel et al., "Percutaneous Coronary Ultrasonic Angioplasty: Initial Clinical Experience", *Eur. Heart J.*, 1993, 14, 78, abstract 588.

Riessen et al., "Percutaneous arterial gene transfer using pure DNA applied to a hydrogel-coated angioplasty balloon", *Eur. Heart J.*, 1993, 14, 78, abstract 590.

Rennie et al. (eds.), 1996 Scientific American, Sep. 1996, 126-132.

Orkin et al., "Report and Recommendations of the Panel to Assess the NIH Investment in Research on Gene Therapy", Dec. 7, 1995.

Schutt et al., "Osmotically Stabilized Microbubble Sonographic Contrast Agents", *Acad. Radiol.*, vol. 3, Suppl. 2, pp. S188-S190 (Aug. 1996).

Frézard, et al., "Permeability and stability in buffer and in human serum of fluorinated phospholipid-based liposomes", *Biochimica et Biophysica Acta*, 1192, pp. 61-70 (1994).

Frézard, et al., "Fluorinated Phospholipid-Based Vesicles as Potential Drug Carriers: Encapsulation/Sustaining of Drugs and Stability in Human Serum", *Art, Cells, Blood Subs., and Immob. Biotech.*, 22(4), pp. 1403-1408 (1994).

Chang et al., "Semipermeable Aqueous Microcapsules", *Canadian J. Of Phys. And Pharm.*, 1966, 44, 115-128.

Chang, "Semipermeable Microcapsules", *Science*, 1964, 146, 524-525.

Deasy, *Microencapsulation and Related Drug Processes*, 1983, vol. 20, Chs. 9 and 10, 195-240 (Marcel Dekker, Inc., NY).

Yeung et al., "Preparation of Microencapsulated Liposomes", *J. Microencapsulation*, 1988, 5, 331-337.

Mattrey et al., Gas Emulsions as Ultrasound Contrast Agents; Preliminary Results in Rabbits and Dogs, *Investigative Radiology*, vol. 29, June Supp. 2, pp. S139-S141, 1994.

Meltzer et al., Transmission of Ultrasonic Contrast Through the Lungs, *Ultrasound in Med. & Biol.*, vol. 7, No. 4, 377-384, 1981.

PR Newswire, Apr. 1, 1986.

Swanson et al., Chapter 22, "Enhancement Agents for Ultrasound: Fundamentals", *Pharmaceuticals In Medical Imaging*, pp. 682-687 (1990).

Ophir et al., "Contrast Agents in Diagnostic Ultrasound", *Ultrasound in Med. & Biol.*, vol. 15, No. 4, pp. 319-333 (1989).

Jacobs, "Intraocular gas measurement using A-scan ultrasound", *Current Eye Research*, vol. 5, No. 8, pp. 575-578 (1986).

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610-1611.

Lincoff et al., "The Perfluorocarbon Gases in the Treatment of Retinal Detachment", *Ophthalmology*, 1983, 90(5), 546-551.

Gardner et al., "A Survey of Intraocular Gas Use in North America", *Arch. Ophthalmol.*, 1988, 106, 1188-1189.

Unger et al., "Liposomal MR Contrast Agents", *J. Liposome Research*, 1994, 4(2), 811-834.

Feinstein, Steven B., "Myocardial Perfusion Imaging: Contrast Echocardiography Today and Tomorrow," *Journal of the American College of Cardiology*, 8(1):251-253 (1986).

Keller et al., "The Behavior of Sonicated Albumin Microbubbles Within the Microcirulation: A Basis for Their Use During Myocardial Contrast Echocardiography", *Circulation Res.*, 65(2):458-465 (1989).

Lincoff et al., "Perfluoro-n-butane: A Gas for Maximum Duration Retinal Tamponade," *Arch Ophthalmology*, 101:460-462 (1983).

*Remington's Pharmaceutical Sciences*, John Hoover, managing ed., Mack Publishing Company, Easton, PA, pp. 295-298; 736; 1242-1244 (1975).

*Handbook of Pharmaceutical Excipients*, American Pharmaceutical Association, Washington, D.C. and The Pharmaceutical Society of Great Britain, London, England, pp. 181-183 (1986).

Barnhart et al., "Characteristics of Albunex™: Air-Filled Microspheres for Echocardiography Contrast Enhancement," *Investigative Radiology*, 25:S162-164, Sep. 1990.

Levene et al., "Characterization of Albunex™," *J. Acoust. Soc. Am.*, 87(Suppl.1):569-70, 1990.

Miller et al., "Physiochemical Approaches to the Mode of Action of General Anesthetics," *J. Amer. Soc. Anesthesiologists*, 36(4):339-351 (1972).

"Properties and Applications of the 'Freon' Fluorocarbons" in DuPont Freon Technical Bulletin B-2 (E.I. DuPont de Nemours and Company, Wilmington, DE), pp. 1-11 (1964).

"'Freon' Fluorocarbons: Properties and Applications" in DuPont Technical Bulletin G-1 (E.I. DuPont de Nemours and Company, Wilmington, DE), pp. 1-10 (1987).

"Encyclopedia of Polymer Science and Engineering," John Wiley & Sons, New York, 1:164-169 (1985).

"Concise Encyclopedia of Polymer Science and Engineering," J. Kroschwitz, ed., John Wiley & Sons, New York, pp. 12-13 (1990).

Wheatley et al., "Contrast Agents for Diagnostic Ultrasound: Development and Evaluation of Polymer-Coated Microbubbles," *Biomaterials*, 11:713-717 (1990).

Arai et al., "Immunologically Distinct p53 Molecules Generated by Alternative Splicing", *Mol. Cell Biol.*, 1986, 6(9), 3232-3239.

Arai et al., Complete Nucleotide Sequence of the Chromosomal Gene for Human IL-4 and its Expression, *J. Immunol.*, 1989, 142(1), 274-282.

Axel et al., "Transformation of Mammalian Cells with Prokaryotic and Eukaryotic Genes", *J. Supramol. Struct.*, 1979, 8 (Supp. 3), 41.

Barnes et al., "Gene Therapy and Ovarian Cancer: A Review", *Obstetrics and Gynecology*, 1997, 89(1), 145-155.

Bratty et al., "The hammerhead RNA domain, a model ribozyme", *Biochim. Biophys. Acta*, 1993, 1216, 345-349.

Delius et al., "Extracorporeal Shock Waves for Gene Therapy", *Lancet*, 1995, 345, 1377.

Fiddes et al., "Structure of genes for human growth hormone and chorionic somatomammotripin", *Proc. Natl. Acad. Sci. USA*, 1979, 76(9), 4294-4298.

Foecking et al., "Powerful and versatile enhancer-promoter unit for mammalian expression vectors", *Gene*, 1986, 45, 101-105.

Gambihler et al., "Permeabilization of the Plasma Membrane of L1210 Mouse Leukemia Cells Using Lithotripter Shock Waves", *J. Membr. Biol.*, 1994, 141, 267-275.

Giddings et al., "Selective Expression and Developmental Regulation of the Ancestral Rat Insulin II Gene in Fetal Liver", *Mol. Endocrinol.*, 1990, 4(9), 1363-1369.

Higuchi et al., "Characterization of Mutations in the Factor VIII Gene by Direct Sequencing of Amplified Genomic DNA", *Genomics*, 1990, 6, 65-71.

Kawabata et al., "Effect of second-harmonic superimposition in efficient induction of sonochemical effect", *Ultrasonics Sonochem.*, 1996, 3, 1-5.

Lauer et al., "Towards a New Gene Transfer System: Shock Wave-Mediated DNA Transfer", *J. Cell Biochem.*, 1994, (Supp. 18A), 226.

Maier et al., "Thymocytes Express a mRNA that is Identical to Hypothalamic Luteinizing Hormone-Releaseing Hormone mRNA", *Cell Mol. Neurobiol.*, 1992, 12(5), 447-454.

Mobley et al., "Low Energy Lithotripsy with the Lithostar: Treatment Results with 19,962 Genal and ureteral Calculi", *J. Urol.*, 1993, 149, 1419-1424.

McKay, "Structure and function of the hammerhead ribozyme: An unfinished story", *RNA*, 1996, 2, 395-403.

Mitsudomi et al., "Detection and Sequencing of p53 Gene Mutations in Bronchial Biopsy Samples in Patients with Lung Cancer", *Chest*, 1993, 104(2), 362-365.

Rubin et al., 31st Annual Meeting of the American Society of Clinical Oncology, May 20-23, 1995, (Abstract No. 589).

Thompson, "At Age 2, Gene Therapy Enters a Growth Phase", *Science*, 1992, 258, 744-746.

Trucco et al., "Rapid Detection of IDDM Susceptibility with HLA-DQ β-Alleles as Markers", *Diabetes*, 1989, 38, 1617-1622.

Tsujimoto et al., "Analysis of the structure, transcripts, and protein products of *bcl-2*, the gene involved in human follicular lymphoma", *Proc. Natl. Acad. Sci. USA*, 1986, 83, 5214-5218.

Zhang et al., "Ultrasonic Direct Gene Transfer the Establishment of High Efficiency Genetic Transformation System for Tobacco", *Sci. Agric. Sin.*, 1991, 24, 83-89 (Abstract attached).

\* cited by examiner

METHODS FOR DELIVERING COMPOUNDS INTO A CELL

RELATED APPLICATIONS

This is a divisional application Ser. No. 08/841,169 filed Apr. 29, 1997, which is a continuation-in-part of application Ser. No. 08/785,661, filed Jan. 17, 1997 (now abandoned), which is a continuation-in-part of application Ser. No. 08/640,554, filed May 1, 1996 (now abandoned), which is a continuation application of Ser. No. 08/346,426, filed Nov. 29, 1994 (now U.S. Pat. No. 5,733,572), the contents of each of which are incorporated herein by reference in their entirety.

FIELD OF THE INVENTION

This invention relates to the field of intracellular delivery, in particular, to the use of organic halides and/or ultrasound to facilitate the delivery of a compound into a cell.

BACKGROUND OF THE INVENTION

Cells are the basic structural and functional units of all living organisms. All cells contain cytoplasm surrounded by a plasma, or cell, membrane. Most bacterial and plant cells are enclosed in an outer rigid or semi-rigid cell wall. The cells contain DNA which may be arranged in 1) a nuclear membrane or 2) free in cells lacking a nucleus. While the cell membrane is known to contain naturally occurring ion channels, compounds that are therapeutically advantageous to cells are usually too large to pass through the naturally occurring ion channels. Conventional interventional methods of delivery of compounds into cells have proved difficult in view of the need for the compounds to pass through the cell membrane, cell wall, and nuclear membrane.

Molecular biology has resulted in mapping the genomes of many plants and animals including the mapping of much of the human genome. The potential for advances in the understanding of the genetic basis of diseases is great, as is the potential for the development of therapies to treat such diseases. However, to fully take advantage of these advancements and treatment therapies, methods are needed which will allow for the delivery of desired compounds into the target cells. Accordingly, researchers have undertaken the development of a variety of intracellular delivery methods for inserting genes and other compounds into both plant and animal cells.

For example, calcium phosphate DNA precipitation has been used to deliver genetic material into cells in cell culture. However, one drawback of this method is that the resultant efficiency of transfection (delivery of the genetic material into the cells) and subsequent gene expression has been very low.

Improved transfection has been attained using viral vectors, e.g., adenovirus and retrovirus, but again, difficulties with gene expression have persisted. In addition, substantial concerns regarding antigenicity and the potential of mutant viruses and other possible deleterious effects exist.

Liposomes, manufactured more easily than viral vectors, have shown promise as gene delivery agents. Liposomes have less biological concerns (in that, for example, they are generally non-antigenic) but the efficiency of transfection and gene expression using liposomes has typically been lower than with viruses.

Gene guns, wherein genes are attached to heavy metal particles such as gold, have been used to fire the particles at high speed into cells. However, while gene guns have resulted in gene expression in culture systems, they have not worked well in vivo. Furthermore, the blast of heavy metal particles may cause damage to the cells and may result in the introduction of undesirable foreign materials, e.g. gold particle fragments, into the cells.

Electroporation is another method of delivering genes into cells. In this technique, pulses of electrical energy are applied to cells to create pores or openings to facilitate passage of DNA into the cells. However, electroporation may damage cells, and furthermore has not been shown to be highly effective in vivo.

Various publications disclose the use of lithotripsy shock waves for effecting intracellular gene transfer, as well as the delivery of other compounds, including, for example, Delius, M., et al., "Extracorporeal Shock Waves for Gene Therapy," *Lancet* May 27, 1995, 345:1377; Lauer, U., et al., "Towards A New Gene Transfer System: Shock Wave-Mediated DNA Transfer," *J Cell Biochem* 1994, 16A:226; Gambihler, S., et al., "Permeabilization of the Plasma Membrane of L1210 Mouse Leukemia Cells Using Lithotripter Shock Waves," *J Membr Biol* 1994, 141:267-75; and Mobley, T. B., et al., "Low Energy Lithotripsy with the Lithostar: Treatment Results with 19,962 Genal and Ureteral Calculi," *J Urol* 1993, 149:1419-24. Lithotripsy delivers energy in the range of 200-380 bars, and a frequency of 60-120 Hz, but may be as high as 1200 to 1300 bars. The energy and frequency ranges are typically painful to a patient and thus usually require patient sedation. Lithotripsy machines are large and bulky and are typically cost prohibitive. Lauer et al. disclose the delivery of 250 shock waves at 25 kV with a lithotripter to deliver plasmid DNA which expressed hepatitis B virus surface proteins in a HeLa cell suspension. Gambihler et al. (cited above) teach the permeabilization of mouse cells in vitro to deliver dextrans. The lithotripter shock waves are delivered at 25 kV, at a discharge rate of 60/min. Mobley et al. (cited above) disclose the use of lithotripsy to treat renal and ureteral stones. The shock wave pressure was 200 to 380 bar and a generator range of 10 to 29 kV.

Zhang, L., et al., "Ultrasonic direct gene transfer The Establishment of High Efficiency Genetic Transformation System for Tobacco," *Sci Agric. Sin.* 1991, 24:83-89 disclose increased gene expression by tobacco using continuous wave ultrasound at 0.5 W/cm$^2$ for 30 minutes. Zhang et al. do not disclose the ultrasound frequency. The high energy level is in a range necessary for poration to result in the cell wall of tobacco plants.

Rubin, et al., 31st Annual Meeting of the American Society of Clinical Oncology, May 20-23, 1995, disclose the injection of hepatic tumors with a plasmid/cationic lipid complex with ultrasound guidance. Ultrasound is disclosed as a visual guide to monitor the injection of the tumors, rather than as an aid to deliver the complex to the liver tumors.

The present invention provides new and/or better methods for delivering compounds, including genetic material, into a cell. The methods of the present invention may provide a significant advantage over prior art methodology, in that enhanced levels of intracellular delivery, and in the case of nucleotides, gene expression, may be achieved. In addition, the process of the present invention may be performed in cell lines which may be otherwise resistant to intracellular delivery and gene expression using other conventional means. These and/or other aspects of the present invention will become apparent from the further discussions herein.

SUMMARY OF THE INVENTION

The present invention is directed, inter alia, to a method for delivering a compound into a cell comprising administering to the cell a composition which comprises the compound to be delivered and an organic halide.

In addition, the invention provides a method of treating a patient comprising administering to a patient a composition comprising a therapeutically effective amount of a compound and an organic halide.

The subject invention provides a method of effecting the expression of a nucleotide sequence in a cell comprising administering to said cell a composition which comprises a nucleotide sequence and an organic halide.

If desired, the compositions may further comprise a carrier. In addition, the method of the invention may further comprise the application of ultrasound, as desired.

The present invention is also directed to a method for delivering a compound into a cell comprising administering to the cell the compound to be delivered, or a composition comprising the compound to be delivered, and applying ultrasound.

Further, the invention pertains to a method of treating a patient comprising administering to a patient a therapeutically effective amount of a compound, or a composition comprising a therapeutically effective amount of a compound, and applying ultrasound.

Moreover, the subject invention provides a method of effecting the expression of a nucleotide sequence in a cell comprising administering to the cell a nucleotide sequence, or a composition which comprises a nucleotide sequence, and applying ultrasound.

If desired, the composition may further comprise carrier.

Also included in the present invention are compositions and kits comprising, for example, a therapeutically effective or diagnostically effective amount of a compound to be delivered, an organic halide, and/or a carrier, and, in the case of a kit, optionally other conventional kit components.

These, as well as other, aspects of the invention are set forth in greater detail below.

BRIEF DESCRIPTION OF THE FIGURES

In FIG. 1, A represents a standoff platform. B is a six well plate, with individual wells B'. C represents an ultrasound gel, while D represents a therapeutic ultrasound transducer. In accordance with the invention, cells, the compound to be delivered, an organic halide (if desired), and optionally a carrier are placed in the wells. Using ultrasound transducer D, ultrasound is then applied to cell culture plate B such that the standoff platform (A) is cut (G) under each well (B') for focusing ultrasound to the individual wells (B'). Ultrasound transducer D may also be employed for the in vivo delivery of compounds by applying transducer D, with ultrasound gel C, to a patient instead of to a cell culture plate.

In FIG. 4, A is a portion of the standoff platform, B' is one well of six well plate B, C is the ultrasound gel, D is the ultrasound transducer, E represents the cells, and F represents microsphere carriers for the compound to be delivered.

DETAILED DESCRIPTION OF THE INVENTION

Figure 1:
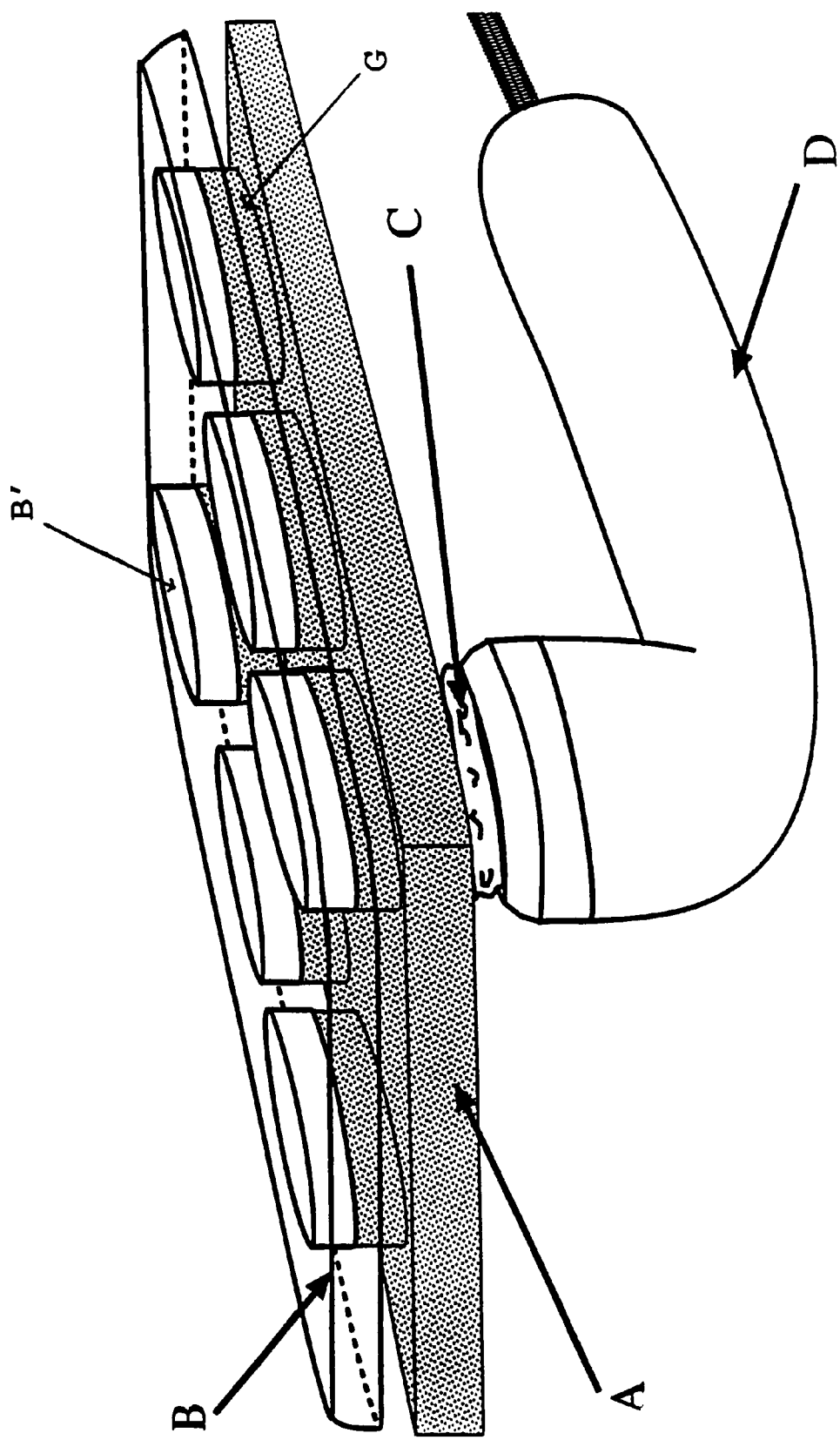
FIG. 1 depicts a test set-up for delivery of compounds to a cell in vitro or ex vivo.
Figure 2:
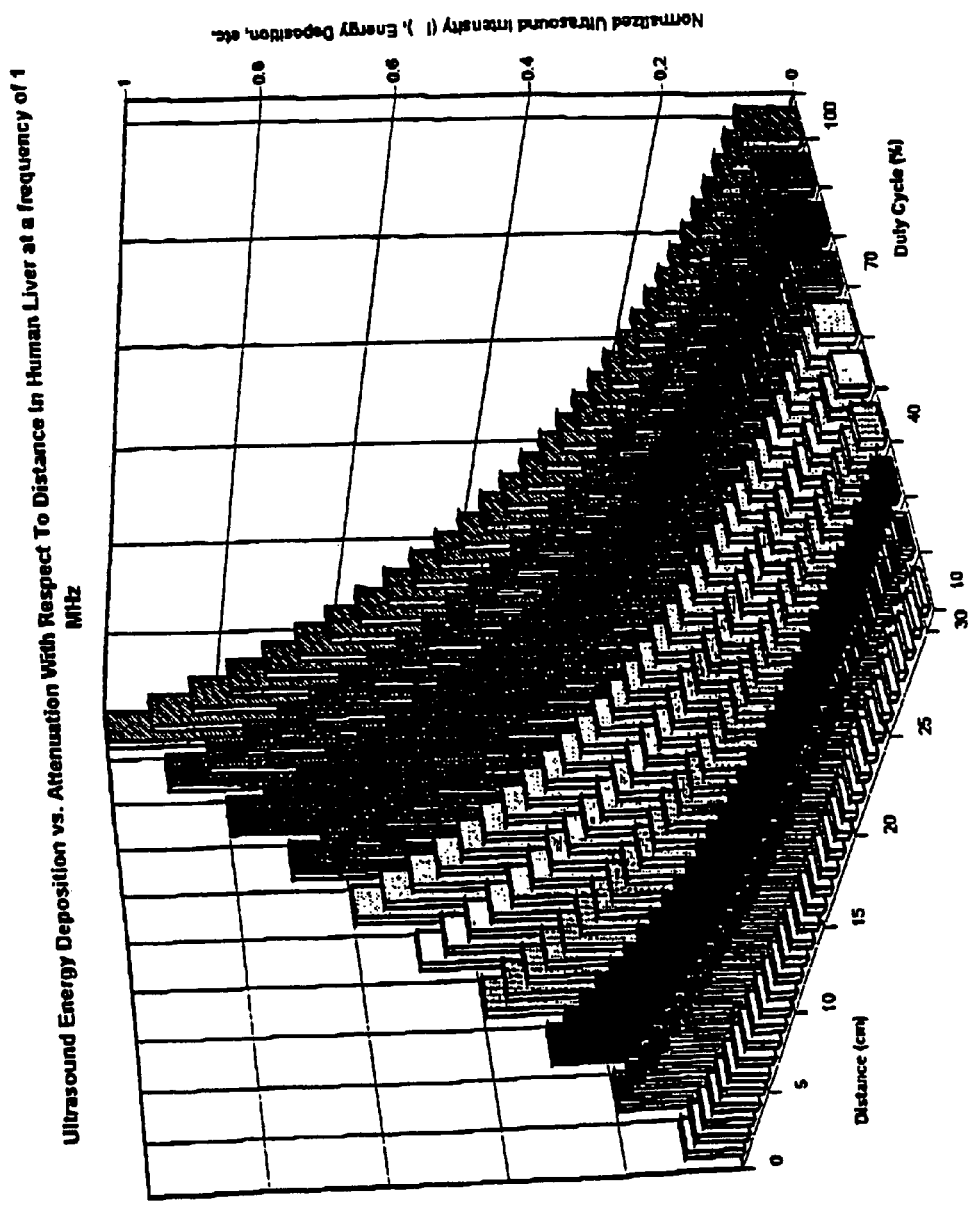
FIG. 2 displays the relationship between energy deposition, ultrasound energy intensity, and ultrasound duty cycle (pulse duration). The effect of attenuation as a function of tissue depth is also portrayed as well as spatial peak temporal average power.

As employed above and throughout the disclosure, the following terms, unless otherwise indicated, shall be understood to have the following meanings.

For purposes of the present invention, an "organic halide" (also sometimes referred to as a halogenated organic compound) denotes a compound which contains at least one carbon atom (or optionally sulfur or selenium atom, such as in the case of $SF_6$ and $SeF_6$) and at least one halogen atom selected from the group consisting of fluorine, chlorine, bromine, or iodine. Preferably the halogen is fluorine (i.e., the compound is a fluorinated compound).

Most preferably the organic halide is a fluorinated compound which is perfluorinated (that is, fully fluorinated, e.g., a carbon compound wherein all hydrogen atoms directly attached to the carbon atoms have been replaced by fluorine atoms). The perfluorinated organic halide (perfluorinated compound) is preferably a perfluorocarbon or a perfluoroether. The organic halide may be in the form of a gas, a liquid (including a gaseous precursor), or a solid. Preferably the organic halide is a liquid, even more preferably a liquid which is a gaseous precursor that converts to a gas upon administration. Most preferably, the gaseous precursor converts to a gas at the site of (in close or touching proximity to) the cell.

"Gaseous precursor" refers to a liquid or solid which is activated upon attaining a certain temperature or pressure to convert to a gas. A gaseous precursor which is capable of converting to a gas at the site of the cell may increase the efficiency of cellular uptake of compounds, and is therefore preferred.

Ideally, the gaseous precursors are liquid (or solid) at ambient (room) temperature (e.g., 25° C.), but will convert to a gas either at physiological temperature (e.g., 37° C.) such as upon administration to a patient, or otherwise conveniently at the site of the cell such as upon application of heat (such as, for example, using ultrasound). If heat is applied, it should be done so at a temperature sufficient to convert the gaseous precursor to a gas, but insufficient to harm the cell (e.g., denature the proteins, etc.). Thus, ideally a gaseous precursor becomes a gas at less than about 80° C. Even more ideally, the gaseous precursor becomes a gas at between about 30° C. and about 70° C. Most ideally, the gaseous precursor becomes a gas at between about 37° C. and less than about 50° C.

A variety of different organic halides may be employed in this invention. Where the organic halide is a carbon based halide compound, the organic halide preferably contains from 1 to about 30 carbon atoms, more preferably 1 to about 24 carbon atoms, even more preferably 1 to about 12 carbon atoms, still even more preferably about 5 to about 12 carbon atoms, and most preferably about 6 to about 10 carbon atoms. Thus, the number of carbon atoms in the organic halide may be 1, 2, 3, 4, 5, 6, 7, 8, 9, 10, 11, 12, 13, 14, 15, 16, 17, 18, 19, 20, 21, 22, 23, 24, carbon atoms, and upwards. Sulfur or selenium based halide compounds, such as sulfur hexafluoride and selenium hexafluoride, are also within the scope of the invention and the phrase organic halide as used herein. The organic halides contemplated herein may also, for example, have carbon atoms interrupted by one or more heteroatoms, such as —O— bonds (as in ether compounds) or have other substituents such as amines, etc. Preferred organic halides of the present invention are the perfluorinated organic halides such as perfluorocarbons and perfluoroethers.

Table 1 lists representative organic halides useful in the present invention. Other organic halides suitable for use in the present invention will be readily apparent to one skilled in the art, once armed with the present disclosure. All such organic halides are intended to fall within the scope of the term organic halide, as used herein.

TABLE 1

Organic Halides

| Compound | Boiling Point (° C.) |
|---|---|
| 1. Mixed-halogenated Compounds | |
| 1-bromo-nonafluorobutane | 43 |
| perfluorooctyliodide | 160-161 |
| perfluoroocytlbromide | 142 |
| 1-chloro-1-fluoro-1-bromomethane | 38 |
| 1,1,1-trichloro-2,2,2-trifluoroethane | 45.7 |
| 1,2-dichloro-2,2-difluoroethane | 46 |
| 1,1-dichloro-1,2-difluoroethane | 45 |
| 1,2-dichloro-1,1,3-trifluoropropane | 50.4 |
| 1-bromoperfluorobutane | 43 |
| 1-bromo-2,4-difluorobenzene | 44 |
| 2-iodo-1,1,1-trifluoroethane | 53 |
| 5-bromovaleryl chloride | 43 |
| 1,3-dichlorotetrafluoroacetone | 43 |
| bromine pentafluoride | 40.3 |
| 1-bromo-1,1,2,3,3,3-hexafluoropropane | 35.5 |
| 2-chloro 1,1,1,4,4,4-hexafluoro-2-butene | 33 |
| 2-chloropentafluoro-1,3-butadiene | 37 |
| iodotrifluoroethylene | 30 |
| 1,1,2-trifluoro-2-chloroethane | 30 |
| 1,2-difluorochloroethane | 35.5 |
| 1,1-difluoro-2-chloroethane | 35.1 |
| 1,1-dichlorofluoroethane | 31.8 |
| heptafluoro-2-iodopropane | 39 |
| bromotrifluoroethane | −57.8 |
| chlorotrifluoromethane | −81.5 |
| dichlorodifluoromethane | −29.8 |
| dibromofluoromethane | 23 |
| chloropentafluoroethane | −38.7 |
| bromochlorodifluoromethane | −4 |
| dichloro-1,1,2,2-tetrafluoroethane | 3.1-3.6 |
| 2. Fluorinated Compounds | |
| 1,1,1,3,3-pentafluoropentane | 40 |
| perfluorotributylamine | 178 |
| perfluorotripropylamine | 130 |
| 3-fluorobenzaldehyde | 56 |
| 2-fluoro-5-nitrotoluene | 53 |
| 3-fluorostyrene | 40 |
| 3,5-difluoroaniline | 40 |
| 2,2,2-trifluoroethylacrylate | 45 |
| 3-(trifluoromethoxy)-acetophenone | 49 |
| 1,1,2,3,3,4,4-octafluorobutane | 44.8 |
| 1,1,1,3,3-pentafluorobutane | 40 |
| 1-fluorobutane | 32.5 |
| 1,1,2,2,3,3,4,4-octafluorobutane | 44.8 |
| 1,1,1,3,3-pentafluorobutane | 40 |
| perfluoro-4 methylquinolizidine | 149 |
| perfluoro-N-methyl-decahydroquinone | 150-155 |
| perfluoro-N-methyl-decahydroisoquinone | 150-155 |
| perfluoro-N-cyclohexyl-pyrrolidine | 145-152 |

TABLE 1-continued

Organic Halides

| Compound | Boiling Point (° C.) |
|---|---|
| tetradecaperfluoroheptane | 76 |
| dodecaperfluorocyclohexane | 52 |
| 3. Perfluorinated Compounds | |
| a. Perfluorocarbons | |
| perfluoromethane | −129 |
| perfluoroethane | −78.3 |
| perfluoropropane | −36 |
| perfluorobutane | −2 |
| perfluoropentane | 29.5 |
| perfluorohexane | 59-60 |
| perfluoroheptane | 81 |
| perfluorooctane | 102 |
| perfluorononane | 125 |
| perfluorodecane | ~143 |
| perfluorododecane | melting pt 75-77 |
| perfluoro-2-methyl-2-pentene | 51 |
| perfluorocyclohexane | 52 |
| perfluorodecalin | 142 |
| perfluorododecalin | — |
| perfluoropropylene | −28 |
| perfluorocyclobutane | −6 |
| perfluoro-2-butyne | −25 |
| perfluoro-2-butene | 1.2 |
| perfluorobuta-1,3-diene | 6 |
| b. Perfluoroether Compounds | |
| perfluorobutylethyl ether | 60 |
| bis(perfluoroisopropyl) ether | 54 |
| bis(perfluoropropyl) ether | 59 |
| perfluorotetrahydropyran | 34 |
| perfluoromethyl tetrahydrofuran | 27 |
| perfluoro t-butyl methyl ether | 36 |
| perfluoro isobutyl methyl ether | — |
| perfluoro n-butyl methyl ether | 35.4 |
| perfluoro isopropyl ethyl ether | — |
| perfluoro n-propyl ethyl ether | 23.3 |
| perfluoro cyclobutyl methyl ether | — |
| perfluoro cyclopropyl ethyl ether | — |
| perfluoro isopropyl methyl ether | 36 |
| perfluoro n-propyl methyl ether | — |
| perflouro diethyl ether | 3-4.5 |
| perfluoro cyclopropyl methyl ether | — |
| perfluoro methyl ethyl ether | −23 |
| perfluoro dimethyl ether | −59 |
| c. Other | |
| sulfur hexafluoride | m.p. −50.5, sublimes −63.8 |
| selenium hexafluoride | m.p. −34.6 sublimes −46.6 |

Preferred organic halides include 1-bromo-nonafluorobutane, 1,1,1,3,3-pentafluoropentane, perfluorohexane, perfluorocyclohexane, 1-bromo-1,1,2,3,3,3-hexafluoropropane, heptafluoro-2-iodopropane, 1,1,2,2,3,3,4,4-octafluorobutane, 1-fluorobutane, tetradecaperfluoroheptane and dodecaperfluorocyclohexane. Particularly preferred are perfluorohexane (especially n-perfluorohexane) and perfluorocyclohexane. A wide variety of other organic halides useful in the present invention will be readily apparent to those of skill in the art once armed with the present disclosure. Suitable additional organic halides include those, for example, disclosed in Long, Jr. in U.S. Pat. Nos. 4,987,154, 4,927,623, and 4,865,836, the disclosures of each of which are hereby incorporated herein by reference in their entirety.

The amount of organic halide employed in the present invention may vary, as one skilled in the art will recognize, once armed with the present disclosure, and may be dependent on such factors as the particular organic halide employed, type and nature of the compound to be delivered, the age, weight, cells or patient (animal) to be treated, the particular diagnostic, therapeutic or other application intended (including the disease state, if any, to be treated). Typically lower amounts are used and then increased until the desired delivery effect is achieved. Representative amounts are set forth in the examples herein. Of course, higher or lower amounts may be employed, as will be recognized by the skilled artisan.

Methods of introducing compounds into a cell (also referred to variously herein as methods for delivering a compound into a cell, methods of intracellular delivery, methods of promoting, effecting, facilitating or enhancing the uptake of a compound into a cell, and the like) include "transfection", which refers to the introduction of genetic material, i.e., a nucleotide sequence (e.g., DNA or RNA) into a host cell. Transfection is also sometimes referred to as transformation. DNA (or RNA) which is new to the cell into which it is incorporated is typically referred to as heterologous DNA (or RNA) or exogenous DNA (or RNA). Some bacterial species take up exogenous DNA and do not discriminate between uptake of DNA from a similar or same species or from a completely different species or organism. Exogenous DNA may also be taken up by cells, but may or may not be incorporated into nuclear material in a hereditable manner. The objective of transfection of a host cell may be to effect expression of one or more carefully selected sequences.

"Expression" and "gene expression" refer to the transcription and/or translation of a nucleic acid sequence resulting in the production of an amino acid, peptide and/or protein. The nucleic acid sequence may or may not be incorporated into the genetic material of the host cell. For example, the nucleic acid sequence may be incorporated into the genome of a host cell or may simply be introduced into the cell without incorporation into the genome.

Gene expression, upon administration of the composition of the present invention, may be effected (obtained, promoted, facilitated or enhanced), and in fact may be enhanced in that the expression of the nucleic acid sequences as compared to conventional transfection techniques such as calcium phosphate precipitation, viral vectors, microinjection, shock wave such as for example lithotripsy, and electroporation, may be increased. Methods of measuring enhanced gene expression will be known to skilled artisans once armed with the present disclosure and include enzyme-linked immunosorbent assay (ELISA) as well as methods disclosed in Sambrook, et al., *Molecular Cloning: A Laboratory Manual,* 2nd ed., Cold Spring Harbor Laboratory Press, Cold Spring Harbor, N.Y. (1989), the disclosures of which are hereby incorporated herein by reference in their entirety. Thus, as a result of the methods of the present invention, a product (e.g., a protein) may be produced. In addition, the prevention of the production of a product (such as, as a result of an antisense sequence delivered into the cell) by the host cell may also result.

Without being bound by any theory of operation, it is believed that delivery of nucleic acid sequences and other compounds in accordance with the methods of the present invention may induce a cell to take up the compound to be delivered thereto. Included within the definition of delivery of a compound into a cell in accordance with the methods of the present invention are active and passive mechanisms of cellular uptake. Ion channels and other means of transport utilized by cells to incorporate extracellular materials, including compounds to be delivered thereto, into the intracellular milieu are encompassed by the present invention.

"Nucleotide sequence and nucleic acid sequence" refer to single and double stranded DNA and RNA sequences, including and not limited to oligonucleotide sequences of about 100 kb to about 1,000,000 kb (including whole chromosomes), preferably of about 4 kb to about 6 kb, more preferably about 1,000 nucleotides in length, more preferably about 500 nucleotides in length, more preferably about 250 nucleotides in length, more preferably about 100 nucleotides in length, more preferably about 50 nucleotides in length, more preferably about 25 nucleotides in length, more preferably about 10 nucleotides in length, even more preferably about 3 to about 10 kbp in length. Embodied by the term "nucleotide sequence" are all or part of a gene, at least a portion of a gene, a gene fragment, a sense sequence, an antisense sequence, an antigene nucleic acid, a phosphorothioate oligodeoxynucleotide, and an alteration, deletion, mismatch, transition, transversion, mutation, conservative substitution, and homolog of a sequence. The phrase "at least a portion of," and "all or part of," as used herein, means that the entire gene need not be represented by the sequence so long as the portion of the gene represented is effective to block or exhibit, depending on the type of sequence used, gene expression. The sequences may be incorporated into an expression vector such as, and not limited to, a plasmid, phagemid, cosmid, yeast artificial chromosome (YAC), virus (e.g., adenovirus, vaccinia virus, retrovirus), and defective virus (also known as a "helper virus"). The nucleotide sequence may also be administered naked, that is without an expression vector.

"Cell" and "host cell" refer to prokaryotic cells and eukaryotic cells, including plant cells, animal cells, cells of unicellular organisms, cells of multicellular organisms, etc. Especially preferred are animal cells, more preferably mammalian cells and most especially human cells, including but not limited to living cells, tissues, and organs. Eukaryotic cells are cells of higher organisms in which genetic material is enclosed by a nuclear membrane. Prokaryotic cells are cells of lower organisms that lack a well defined nucleus and contain genetic material that is not enclosed within a membrane of its own. The cells may be present in vivo or in vitro (e.g. in cell culture).

The invention has wide applications for effecting (obtaining, promoting, facilitating or enhancing) and/or increasing the efficiency of, intracellular delivery (e.g., transfection) and/or, in the case of nucleotides, gene expression in both in vitro and in vivo applications, and is particularly useful for prokaryotic and eukaryotic animal cells, particularly mammalian cells. Intracellular delivery includes delivery into the cells through a cell membrane (plasma membrane), cell wall, and/or nuclear membrane.

The phrase "cell membrane" (also termed "plasma membrane") is used in its conventional sense as denoting the outer layer or boundary of the cytoplasm of a living cell. Cell membranes are typically comprised of protein and lipids, and are generally found in animal cells.

The phrase "cell wall" is also used in its conventional sense to denote a rigid or semi-rigid outer covering surrounding the protoplasts of plant cells and most prokaryotes. Cell walls are typically found, for example, in cells of bacteria, plants, algae, and fungi. Cell walls are, on the other hand, generally not present in animal cells. In plants, the wall typically comprises several layers; a primary wall composed of cellulose microfibrils running through a matrix of hemicelluloses and pectic substances surrounded by a secondary wall composed of cellulose which is generally lignified to a varying extent. Cell walls of fungi may contain varying amounts of chitin.

Cell walls of prokaryotes are typically strengthened by mucopeptides and may be surrounded by a mucilaginous capsule.

A wide variety of compounds can comprise the compounds to be delivered to the cells in accordance with the invention, including bioactive agents, diagnostic agents, pharmaceutical agents, and the like, and include proteins, DNA and RNA (both single and double-stranded), anti-sense and gene constructs, as well as other organic or inorganic compounds. Whole genes, multiple gene sequences, and gene fragments may be utilized as well as whole chromosomes and chromosome fragments.

As noted above, the methods of the present invention may, for example, be carried out in the presence of an organic halide, with or without the application of ultrasound, or in the absence of an organic halide but with the application of ultrasound. Where bioactive agents other than nucleotides are employed as the compound to be delivered, generally, for best results, an organic halide is used, although use of an organic halide in such a situation is not required.

If desired, the composition may further comprise a carrier. The carrier employed may comprise a wide variety of materials. Carriers may include, for example, lipids, polymers, proteins, surfactants, inorganic compounds, metal ions, and the like, alone or in combination with water and/or a solvent, or the carrier may simply comprise water and/or a solvent. The lipids, proteins, and polymers, for example, may be in liquid form or solid form (such as, for example, the form of particles, fibers, sheets, layers, etc.), or may take the form of a vesicle or other stable, organized form, which may include but is not limited to, such forms commonly referred to as, for example, liposomes, micelles, bubbles, microbubbles, microspheres, lipid-, polymer-, and/or protein-coated bubbles, microbubbles and/or microspheres, microballoons, aerogels, hydrogels, clathrates, hexagonal HII phase structures, and the like. The internal void of the vesicle or other stable form may, for example, be filled with a liquid (including, for example, a gaseous precursor), a gas, a solid, or solute material, or any combination thereof, including, for example, the compound to be delivered, the organic halide, and/or any targeting ligand, as desired. Typically, the carrier is provided as an aqueous milieu, such as water, saline (such as phosphate buffered saline), and the like, with or without other carrier components, although other non-aqueous solvents may also be employed, if desired. The carrier may comprise a mixture in the form of an emulsion, suspension, dispersion, solution, and the like. Lipid (including oil) in water emulsions are especially preferred. As indicated above, the carrier may also include buffers.

Thus, "vesicle", as used herein, refers to an entity which is generally characterized by the presence of one or more walls or membranes which form one or more internal voids. Vesicles may be formulated, for example, from stabilizing compounds, such as a lipid, including the various lipids described herein, a polymer, including the various polymers described herein, or a protein, including the various proteins described herein, as well as using other materials that will be readily apparent to one skilled in the art. Other suitable materials include, for example, any of a wide variety of surfactants, inorganic compounds, and other compounds as will be readily apparent to one skilled in the art. Also, as will be apparent to one skilled in the art upon reading the present disclosure, the organic halides may themselves act as suitable carriers, and may in certain embodiments themselves form vesicles and other organized structures. Thus the use of the organic halides of the invention in combination with a compound to be delivered, without an additional compound to serve as a carrier, is within the scope of the invention. The lipids, polymers, proteins, surfactants, inorganic compounds, and/or other compounds may be natural, synthetic or semi-synthetic. Preferred vesicles are those which comprise walls or membranes formulated from lipids. The walls or membranes may be concentric or otherwise. In the preferred vesicles, the stabilizing compounds may be in the form of a monolayer or bilayer, and the mono- or bilayer stabilizing compounds may be used to form one or more mono- or bilayers. In the case of more than one mono- or bilayer, the mono- or bilayers may be concentric, if desired. Stabilizing compounds may be used to form unilamellar vesicles (comprised of one monolayer or bilayer), oligolamellar vesicles (comprised of about two or about three monolayers or bilayers) or multilamellar vesicles (comprised of more than about three monolayers or bilayers). The walls or membranes of vesicles prepared from lipids, polymers or proteins may be substantially solid (uniform), or they may be porous or semi-porous. The vesicles described herein include such entities commonly referred to as, for example, liposomes, micelles, bubbles, microbubbles, microspheres, lipid-, protein- and/or polymer-coated bubbles, microbubbles and/or microspheres, microballoons, microcapsules, aerogels, clathrate bound vesicles, hexagonal H II phase structures, and the like. The vesicles may also comprise a targeting ligand, if desired.

"Lipid vesicle", "polymer vesicle" and "protein vesicle" refer respectively to vesicles formulated from one or more lipids, polymers and proteins.

"Liposome" refers to a generally spherical or spheroidal cluster or aggregate of amphipathic compounds, including lipid compounds, typically in the form of one or more concentric layers, for example, monolayers or bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal H2 phase configuration. In other preferred embodiments, the micelles may comprise a bilayer configuration.

"Aerogel" refers to generally spherical or spheroidal entities which are characterized by a plurality of small internal voids. The aerogels may be formulated from synthetic or semisynthetic materials (for example, a foam prepared from baking resorcinol and formaldehyde), as well as natural materials, such as polysaccharides or proteins.

"Clathrate" refers to a solid, semi-porous or porous particle which may be associated with vesicles. In preferred form, the clathrates may form a cage-like structure containing cavities which comprise the vesicles. One or more vesicles may be bound to the clathrate. A stabilizing material may, if desired, be associated with the clathrate to promote the association of the vesicle with the clathrate. Suitable materials from which clathrates may be formulated include, for example, porous apatites, such as calcium hydroxyapatite, and precipitates of polymers and metal ions, such as alginic acid precipitated with calcium salts.

"Emulsion" refers to a mixture of two or more generally immiscible liquids and is generally in the form of a colloid. The liquids may be homogeneously or heterogeneously dispersed throughout the emulsion. Alternatively, the liquids may be aggregated in the form of, for example, clusters or layers, including mono- or bilayers.

"Suspension" or "dispersion" refers to a mixture, preferably finely divided, of two or more phases (solid, liquid or gas), such as, for example, liquid in liquid, solid in liquid, liquid in gas, etc.) which can preferably remain stable for extended periods of time.

"Hexagonal H II phase structure" refers to a generally tubular aggregation of lipids, proteins, or polymers (especially lipids) in liquid media, for example, aqueous media, in which any hydrophilic portion(s) generally face inwardly in association with an aqueous liquid environment inside the tube. The hydrophobic portion(s) generally radiate outwardly and the complex assumes the shape of a hexagonal tube. A plurality of tubes is generally packed together in the hexagonal phase structure.

"Biocompatible" refers to materials which are generally not injurious to biological functions and which will not result in any degree of unacceptable toxicity, including allergenic responses and disease states. The compositions of the present invention and/or components thereof are typically biocompatible.

The nucleotide sequence or other compound to be delivered may be administered, if desired, "in combination with" an organic halide, and may further be administered, if desired, "in combination with" a carrier, including a vesicle (or other stable form). "In combination with" refers to the co-administration of the compound to be delivered and the organic halide (and/or carrier, if desired). The compound to be delivered and the organic halide (and/or any carrier) may be combined in any of a variety of different fashions, including simply being placed in admixture with one another. In addition, for example, the nucleotide or other compound to be delivered and/or the organic halide may be embedded, encapsulated, or attached to, or with, one another, as desired (including any and all combinations thereof). The phrase "in admixture" includes solutions, suspensions, emulsions, dispersions, mixtures, etc. The phrase "attached to" or variations thereof, as used herein, denotes being linked in some manner, such as through a covalent or ionic bond or other means of chemical or electrochemical linkage or interaction. The phrase "encapsulated" and variations thereof as used herein refers to a location inside an internal void of a vesicle or other structure. The phrase "embedded within" or variations thereof as used herein signifies a positioning within the wall of a vesicle or other structure. Thus, a nucleotide sequence, for example, can be positioned variably, such as, for example, entrapped within the internal void of the vesicle, situated on the internal wall of the vesicle, incorporated onto the external surface of the vesicle, and/or enmeshed within the vesicle structure itself. In addition, one or more vesicles may be administered as a cavitator. In such case, the vesicles accompany the administration of a compound and may serve to enhance the efficiency of ultrasound.

Lipids may be used in the present invention as a carrier. The lipids may be natural, synthetic or semisynthetic (i.e., modified natural). Lipids useful in the invention include, and are not limited to, fatty acids, lysolipids, oils (including safflower, soybean and peanut oil), phosphatidylcholine with both saturated and unsaturated lipids including phosphatidylcholine; dioleoylphosphatidylcholine; dimyristoylphosphatidylcholine; dipentadecanoylphosphatidylcholine, dilauroylphosphatidylcholine, dioleoylphosphatidylcholine, dipalmitoylphosphatidylcholine; distearoylphosphatidylcholine; phosphatidylethanolamines such as dioleoylphosphatidylethanolamine; phosphatidylserine; phosphatidylglycerol; phosphatidylinositol, sphingolipids such as sphingomyelin; glycolipids such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate, lipids with ether and ester-linked fatty acids, polymerized lipids (a wide variety of which are known in the art), diacetyl phosphate, stearylamine, cardiolipin, phospholipids with short chain fatty acids of about 6 to about 8 carbons in length, synthetic phospholipids with asymmetric acyl chains (e.g., with one acyl chain of about 6 carbons and another acyl chain of about 12 carbons), 6-(5-cholesten-3b-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylamino-coumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; (cholesteryl)4'-trimethyl-ammonio)butanoate; N-succinyldioleoylphosphatidylethanolamine; 1,2-dioleoyl-sn-glycerol; 1,2-dipalmitoyl-sn-3-succinyl-glycerol; 1,3-dipalmitoyl-2-succinylglycerol; 1-hexadecyl-2-palmitoyl-glycerophosphoethanolamine and palmitoylhomocysteine, and/or combinations thereof. Vesicles or other structures may be formed of the lipids, either as monolayers, bilayers, or multilayers and may or may not have a further coating.

The preferred lipid carrier may be in the form of a monolayer or bilayer, and the mono- or bilayer may be used to form one or more mono- or bilayers. In the case of more than one mono- or bilayer, the mono- or bilayers may be concentric. The carrier may form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of a vesicle may be substantially solid (uniform), or they may be porous or semi-porous.

Lipids bearing hydrophilic polymers such as polyethyleneglycol (PEG), including and not limited to PEG 2,000 MW, 5,000 MW, and PEG 8,000 MW, are particularly useful for improving the stability and size distribution of organic halide-containing composition. Dipalmitoylphosphatidylcholine (DPPC) may be useful in the present invention at about 70% to about 90%, dipalmitoylphosphatidylethanolamine-polyethylene glycol 5000 (DPPE-PEG 5000) may be useful at about 0% to about 20% and dipalmitoylphosphatidic acid (DPPA) may be useful at about 0% to about 20% (all percentages being in mole percent molecular weight). A preferred product which is highly useful as a carrier in the present invention contains about 82 mole percent DPPC, about 8 mole percent DPPE-PEG 5,000 MW and about 10 mole percent DPPA. Various different mole ratios of PEGylated lipid are also useful.

Additionally lipid moieties capable of polymerization are embraced in the invention as coatings for the vesicles. Examples of these include, but are not limited to, alkenyl and alkynyl moieties, such as oleyl and linoleyl groups, diacetylene, acryloyl and methacryloyl groups with or without polar groups to enhance water solubility, cyanoacrylate esters optionally carrying lipophilic esterifying groups or the compounds illustrated as A and B, below. A number of such compounds are described, for example, in Klaveness et al., U.S. Pat. No. 5,536,490. The disclosures of Klaveness et al., U.S. Pat. No. 5,536,490, are hereby incorporated herein by reference in their entirety.

Fluorinated or perfluorinated lipids may also be used in this invention, either as the organic halide component or as an additional carrier material. Examples of suitable fluorinated lipids include but are not limited to compounds of the formula

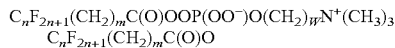

wherein: m is 0 to about 18, n is 1 to about 12; and w is 1 to about 8. Examples of and methods for the synthesis of these, as well as other fluorinated lipids useful in the present invention, are set forth in U.S. application Ser. No. 08/465,868, filed Jun. 6, 1995, Reiss et al. U.S. Pat. No. 5,344,930, Frezard, F., et al., *Biochem Biophys Acta* 1994, 1192:61-70, and Frezard, F., et al., *Art. Cells Blood Subs and Immob Biotech.* 1994, 22:1403-1408, the disclosures of each of which are incorporated herein by reference in their entirety. One specific example of a difluoroacyl glycerylphosphatidylcholine, nonafluorinated diacyl glycerylphosphatidylcholine, is represented by compound A, below. Those skilled in the art will appreciate that analogous fluorinated derivatives of other common phospholipids (diacylphosphatidyl serine, diacylphosphatidyl ethanolamine, diacylphosphatidyl glycerol, diacylphosphatidyl glycerol, etc.) as well as fluorinated derivatives of fatty acyl esters and free fatty acids may also function in accordance with the scope of the invention. Additionally lipid based and fluorinated (including perfluorinated) surfactants such as may be used as carriers in the present invention.

A wide variety of such fluorinated compounds may be employed, including, for example, the class of compounds which are commercially available as ZONYL® fluorosurfactants (the DuPont Company, Wilmington, Del.), including the ZONYL® phosphate salts and ZONYL® sulfate salts, which are fluorosurfactants having terminal phosphate or sulfate groups. Representative compounds are disclosed, for example, in U.S. Pat. No. 5,276,145, the disclosures of which are hereby incorporated herein by reference in their entirety. Suitable ZONYL® surfactants also include, for example, ZONYL® surfactants identified as Telomer B, including Telomer B surfactants which are pegylated (i.e., have at least one polyethylene glycol group attached thereto), also known as PEG-Telomer B, available from the DuPont Company. Most preferred are such pegylated fluorosurfactants.

Suitable polymerizable and/or fluorinated compounds include

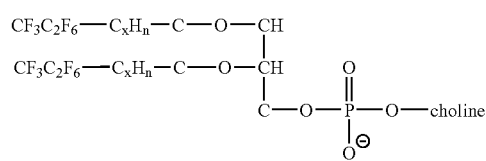

A

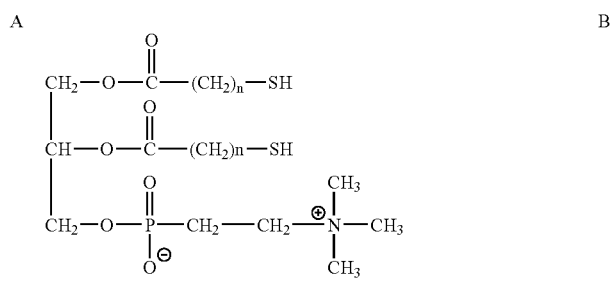

B

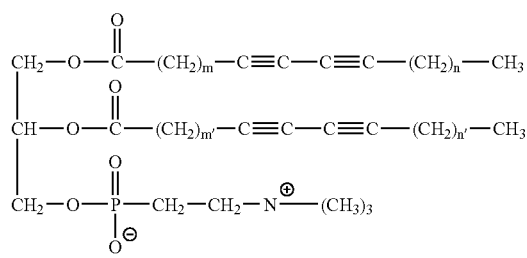

C

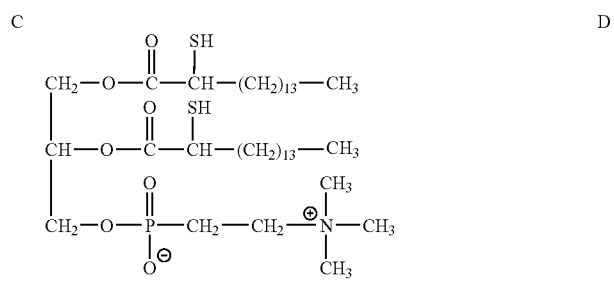

D

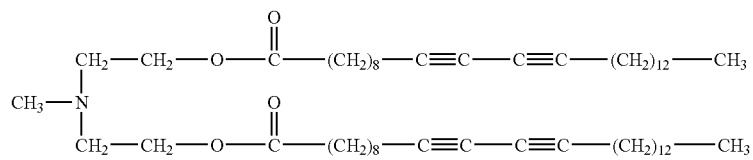

E

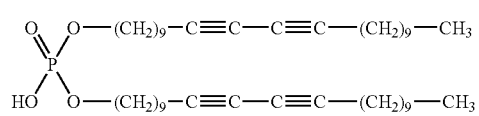

F

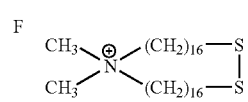

G

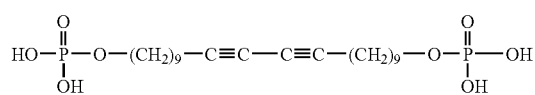

H

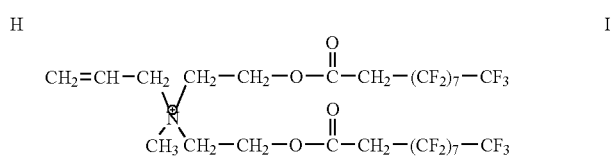

I

-continued

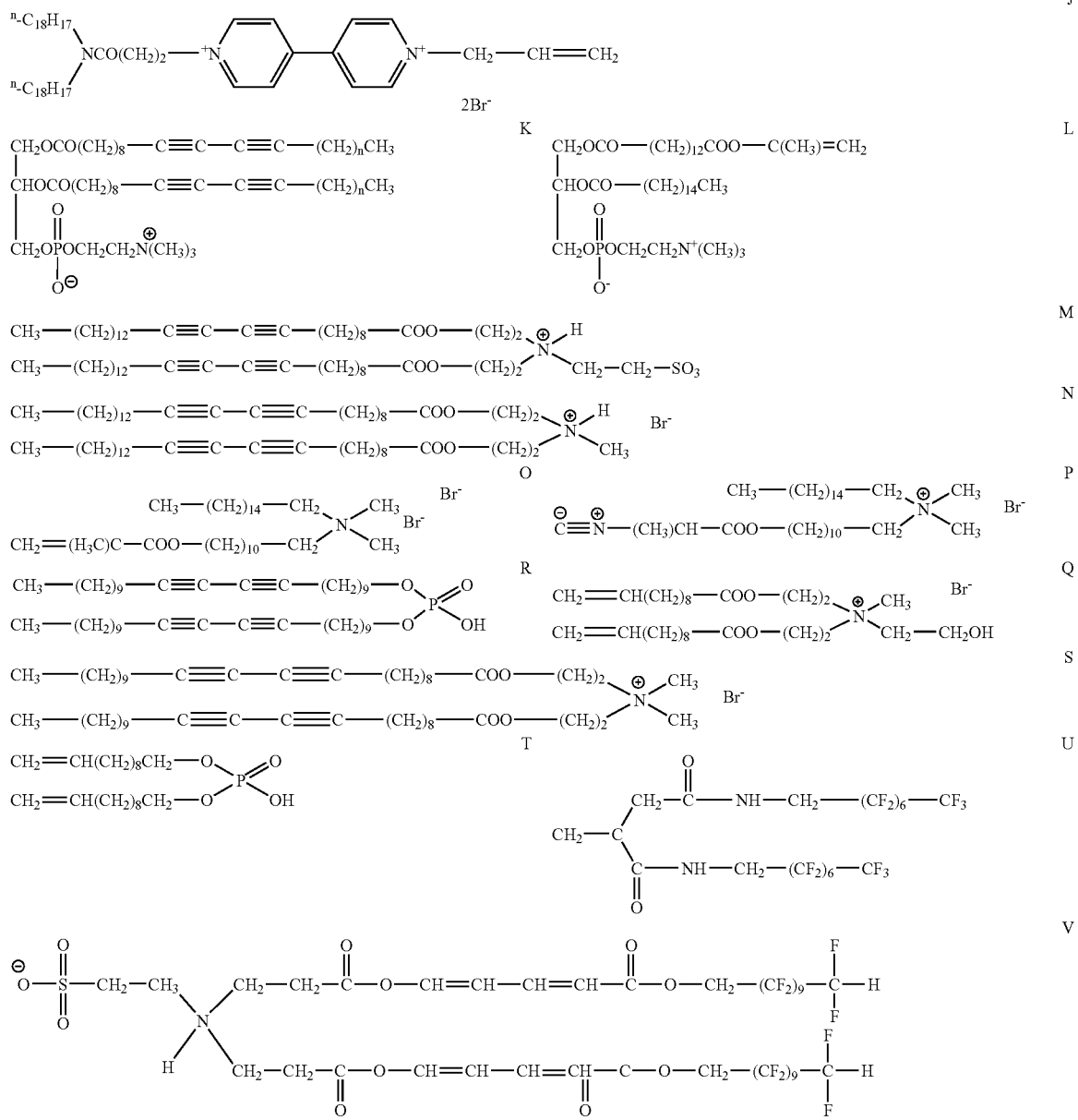

In formula A, above, preferably x is an integer from about 8 to about 18, and n is 2x. Most preferably x is 12 and n is 24.

Cationic lipids and other derivatized lipids and lipid mixtures also may be useful as carriers in the present invention. Suitable cationic lipids include dimyristyl oxypropyl-3-dimethylhydroxy ethylammonium bromide (DMRIE), dilauryl oxypropyl-3-dimethylhydroxy ethylammonium bromide (DLRIE), N-[1-(2,3-dioleoyloxyl) propal]-n,n,n-trimethylammonium sulfate (DOTAP), dioleoylphosphatidylethanolamine (DOPE), dipalmitoylethylphosphatidylcholine (DPEPC), dioleoylphosphatidylcholine (DOPC), polylysine, lipopolylysine, didoceyl methylammonium bromide (DDAB), 2,3-dioleoyloxy-N-[2-(sperminecarboxamidoethyl]-N, N-di-methyl-1-propanaminium trifluoroacetate (DOSPA), cetyltrimethylammonium bromide (CTAB), lysyl-PE, 3,β-[N,(N',N'-dimethylaminoethane)-carbamoyl]cholesterol (DC-Cholesterol, also known as DC-Chol), (-alanyl cholesterol, N-[1-(2,3-dioleoyloxy)propyl]-N, N, N-trimethylammonium chloride (DOTMA), dipalmitoylphosphatidylethanolamine-5-carboxyspermylamide (DPPES), dicaproylphosphatidylethanolamine (DCPE), 4-dimethylaminopyridine (DMAP), dimyristoylphosphatidylethanolamine (DMPE), dioleoylethylphosphocholine (DOEPC), dioctadecylamidoglycyl spermidine (DOGS), N-[1-(2,3-dioleoyloxy)propyl]-N-[1-(2-hydroxyethyl) ]-N, N-dimethylammonium iodide (DOHME), Lipofectin (DOTMA+DOPE, Life Technologies, Inc., Gaithersburg, Md.), Lipofectamine (DOSPA+DOPE, Life Technologies, Inc., Gaithersburg, Md.), Transfectace (Life Technologies, Inc., Gaithersburg, Md.), Transfectam (Promega Ltd., Madison, Wis.), Cytofectin (Life Technologies Inc., Gaithersburg, Md.). Other representative cationic lipids include but are not limited to phosphatidylethanolamine, phosphatidylcholine, glycero-3-ethylphosphatidylcholine and fatty acyl esters thereof, di- and trimethyl ammonium propane, di- and triethylammonium propane and fatty acyl esters thereof. A preferred derivative from this group is N-[1-(2,3-dioleoyloxy) propyl]-N,N,N-trimethylammonium chloride (DOTMA). Additionally, a wide array of synthetic cationic lipids function as compounds useful in the invention. These include common natural lipids derivatized to contain one or more basic functional groups. Examples of lipids which may be so modified include but are not limited to dimethyldioctadecylammonium bromide, sphingolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidyl-ethanolamine and palmitoylhomocystiene.

Other synthesized cationic lipids that are useful in the present invention are those disclosed in pending U.S. patent application Ser. No. 08/391,938, filed Feb. 2, 1995, and include, for example, N,N'-Bis (dodecyaminocarbonylmethylene)-N,N'bis((-N,N,N-trimethylammoniumethyl-aminocarbonylmethylene) ethylenediamine tetraiodide; N,N"-Bis (hexadecylaminocarbonylmethylene)-N,N',N"-tris((-N,N,N-trimethylammonium-ethylaminocarbonylmethylenediethylenetriamine hexaiodide; N,N'-Bis (dodecylaminocarbonylmethylene)-N,N"-bis((-N,N,N-trimethylammoniumethylamino-carbonylmethylene) cyclohexylene-1,4-diamine tetraiodide; 1,1,7,7-tetra-((-N,N,N,N-tetramethylammoniumethylaminocarbonylmethylene)-3-hexadecyl-aminocarbonyl-methylene-1,3,7-triaazaheptane heptaiodide; and N,N,N'N'-tetra((-N,N,N-trimethylammoniumethylaminocarbonylmethylene)-N'-(1,2-di oleoylglycero-3-phosphoethanolaminocarbonylmethylene) diethylenetriamine tetraiodide. Those of skill in the art will recognize that countless other natural and synthetic variants carrying positive charged moieties will also function in the invention.

Also useful as carriers in the present invention are a wide variety of surfactants (i.e., surface-active agents), including polyoxyalkylene fatty acid esters (such as polyoxyethylene fatty acid esters), polyoxyalkylene fatty alcohols (such as polyoxyethylene fatty alcohols), polyoxyalkylene fatty alcohol ethers (such as polyoxyethylene fatty alcohol ethers), polyoxyalkylene sorbitan fatty esters (such as, for example, the class of compounds referred to as TWEEN™, commercially available from ICI Americas, Inc., Wilmington, Del.), including poly(oxyethylene)poly(oxypropylene) copolymers (such as Pluronics), polysorbates (such as Tween20, Tween40, and Tween80), polyoxyethylene alcohols (such as Brij), and plasmalogens, the term applied to a number of a group of phospholipids present in platelets that liberate higher fatty aldehydes, e.g. palmital, on hydrolysis and may be related to the specialized function of platelets in blood coagulation and plasmalogens are also present in cell membranes of muscle and the myelin sheath of nerve fibers.

In the preferred embodiment of the invention the organic halide is incorporated into the core of a vesicle which vesicle carrier is also used to complex the compound to be delivered, such as DNA.

A wide variety of oils may be preferably employed as carriers in the present invention including, but not limited to, safflower, soybean, and peanut oil. The composition may take the form of an oil in water emulsion if desired.

The most preferred carrier is a cationic lipid (including a cationic liposome), particularly as employed in an aqueous milieu. A preferred cationic lipid is DPEPC in admixture with the neutral fusogenic lipid dioleoylphosphatidylethanolamine (DOPE). A preferred ratio of lipid to organic halide is 5:1 w/w. A preferred embodiment is to formulate the lipid or polymer as an organic halide-filled microsphere, such as a microsphere formed with the lipids dipalmitoylphosphatidylcholine (DPPC), dipalmitoylphosphatidylethanolamine coupled to polyethylene glycol 5000 (DPPE-PEG5000), and dipalmitoylphosphatidic acid (DPPA). DPPC:DPPE-PEG5000:DPPA may be combined in a ratio of about 82%:8%:10% (mole %) or 83%:8%:5%. DPPE-PEG5000 is comprised of DPPE and PEG5000 in a ratio of about 20%:80% (weight %). PEG5000 refers to PEG having an average molecular weight of about 5000.

Proteins (including peptides) useful as carriers in accordance with the present invention include molecules comprising, and preferably consisting essentially of, α-amino acids in peptide linkages. A wide variety of proteins may be employed as carriers in the present invention, including natural, synthetic, or semi-synthetic proteins. Included within the term "protein" are globular proteins, such as albumins, globulins and histones, and fibrous proteins such as collagens, elastins and keratins. Also included are "compound proteins", wherein a protein molecule is united with a nonprotein molecule, such as nucleoproteins, mucoproteins, lipoproteins, and metalloproteins. Preferable proteinaceous macromolecules include for example, albumin, collagen, polyarginine, polylysine, polyhistidine, γ-globulin and β-globulin, with albumin, polyarginine, polylysine, and polyhistidine being more preferred. Fluorinated peptides and synthetic pseudopeptides are also useful as carriers. Fluorinated peptides useful in the present invention include those described in Lohrmann, U.S. Pat. No. 5,562,892, the disclosures of which are hereby incorporated herein by reference in their entirety. Cationic peptides may also be usefully employed as carriers in the present invention. Various peptides suitable for use in the present invention will be apparent to one skilled in the art based on the present disclosure.

The methods of the present invention may also involve vesicles or other organized stable form formulated from proteins, peptides and/or derivatives thereof. Vesicles which are formulated from proteins and which would be suitable for use in the methods of the present invention are described, for example, in Feinstein, U.S. Pat. Nos. 4,572,203, 4,718,433, and 4,774,958, and Cerny et al., U.S. Pat. No. 4,957,656, all of the disclosures of each of which are hereby incorporated by reference in their entirety. Other protein-based vesicles, in addition to those described in the aforementioned patents, would be apparent to one of ordinary skill in the art, once armed with the present disclosure.

Included among the methods described in the aforementioned patents for the preparation of protein-based vesicles are methods which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, collagen, and the like. Preferably, the protein is a human protein, with human serum albumin (HSA) being more preferred. HSA is available commercially as a sterile 5% aqueous solution, which is suitable for use in the preparation of protein-based vesicles. Of course, as would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

The protein-based vesicles may be prepared using equipment which is commercially available. For example, in connection with a feed preparation operation as disclosed, for example, in Cerny, et al., U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonicating vessel, in series. Heat exchanger equipment of this type may be obtained from ITT Standard (Buffalo, N.Y.). The heat exchanger maintains operating temperature for the sonication process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commercially available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficient to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Such sonication methods may also be employed to prepare lipid-based or other types of carriers as will be apparent to the skilled artisan.

Suitable methods for the preparation of protein-based vesicles may involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as glutaraldehyde. For example, the vesicles may be reacted with 0.25 grams of 50% aqueous glutaraldehyde per gram of protein at pH 4.5 for 6 hours. The unreacted glutaraldehyde may then be washed away from the protein.

The carriers may also be formulated with polymers, natural, synthetic, or semisynthetic. A wide variety of polymers may be utilized as carriers in the present invention, including synthetic polymers including polyethylenes (such as, for example, polyethylene glycol), polyoxyethylenes (such as, for example, polyoxyethylene glycol), polypropylenes (such as, for example, polypropylene glycol), pluronic acids and alcohols, polyvinyls (such as, for example, polyvinyl alcohol), and polyvinylpyrrolidone. Exemplary natural polymers suitable for use in the present invention include polysaccharides. Polysaccharides include, for example, arabinans, fructans, fucans, galactans, galacturonans, glucans, mannans, xylans (such as, for example, inulin), levan, fucoidan, carrageenan, galactocarolose, pectin (including high methoxy pectin and low methoxy pectin; with low methoxy pectin denoting pectin in which less than 40% of the carboxylic acid groups are esterified and/or amidated, and high methoxy pectin denoting pectin in which 40% or more of the carboxylic acid groups are esterified and/or amidated), pectic acid, amylose, pullulan, glycogen, amylopectin, cellulose, carboxymethylcellulose, hydroxypropyl methylcellulose, dextran, pustulan, chitin, agarose, keratan, chondroitin, dermatan, hyaluronic acid and alginic acid, and various other homopolymers or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, guluronic acid, glucosamine, galactosamine and neuraminic acid. It is recognized that some polymers may be prepared by chemically modifying naturally occurring polymers. Such chemically modified natural polymers also referred to as semisynthetic polymers. The polymers employed may also comprise fluorinated polymers, including those described in Lohrmann, U.S. Pat. No. 5,562,892, the disclosures of which are hereby incorporated herein by reference in their entirety. Furthermore, the polymers may be in the form of vesicles, such as for example, those described in Unger, U.S. Pat. No. 5,205,290, the disclosures of which are hereby incorporated herein by reference in their entirety. As used herein, the term "polymer" denotes molecules formed from the chemical union of two or more repeating units, and include dimers, trimers, and oligomers. In preferred form, the term "polymer" refers to molecules which comprise 10 or more repeating units.

Metal ions may also be employed as carriers in the present invention. Suitable metal ions include calcium ions, magnesium ions, zinc ions, and the like, as well as a wide variety of inorganic compounds. Other suitable metal ions as well as other suitable inorganic compounds will be readily apparent to those skilled in the art once armed with the present invention.

Other useful agents that may be employed in the carrier of the present invention include osmotic agents, anti-microbials, viscosity raising agents, suspending agents, humectants and anti-humectants, depending upon the particular formulation desired.

One or more emulsifying or stabilizing agents may also be employed as or be included in the carrier. These agents help to maintain the size of any discrete units (e.g., liquid droplets, particles, gas bubbles, etc.) of the organic halide and/or compounds to be delivered that may have formed the composition. The size of these discrete units will generally affect the size of any resultant gas bubbles that may form from any gaseous precursors. The emulsifying and stabilizing agents also may be used to generally coat or stabilize the organic halides, compounds to be delivered, etc. Stabilization is desirable to maximize the intracellular delivery effect. Although stabilization is preferred, this is not an absolute requirement. Because any gas resulting from organic halide gaseous precursors is more stable than air, they may still be designed to provide useful delivery means; for example, they pass through the pulmonary circulation following peripheral venous injection, even when not specifically stabilized by one or more coating or emulsifying agents. One or more coating or stabilizing agents is preferred however, as are flexible stabilizing materials. Also, it should be noted that compositions stabilized by polysaccharides, gangliosides, and polymers are generally more effective than those stabilized by albumin and other proteins. Also, liposomes prepared using aliphatic compounds are preferred, since microspheres stabilized with these compounds are much more flexible and stable to pressure changes.

The carrier of the invention may also comprise a wide variety of viscosity modifiers, including and not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Glycerol propylene glycol, polyethylene glycol, polyvinyl pyrrolidone, and polyvinyl alcohol may also be useful as carriers or stabilizers in the present invention. Particles which are porous or semi-solid such as hydroxyapatite, metal oxides and coprecipitates of gels, e.g., hyaluronic acid with calcium may be used and may formulate a center or nidus to stabilize compositions of the invention.

Emulsifying and/or solubilizing agents may also be used in a carrier, particularly in conjunction with lipids or liposomes. Such agents include and are not limited to, acacia, cholesterol, diethanolamine, glyceryl monostearate, lanolin alcohols, lecithin, mono- and di-glycerides, mono-ethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan, sorbitan mono-laurate, sorbitan mono-oleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be particularly useful with lipid or liposome solutions include but are not limited to, acacia, agar, alginic acid, aluminum mono-stearate, bentonite, magma, carbomer 934P, carboxymethylcellulose, calcium and sodium and sodium 12, glycerol, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol, alginate, silicon dioxide, sodium alginate, tragacanth, and xanthum gum. A preferred product of the present invention incorporates lipid as a mixed solvent system in a ratio of 8:1:1 or 9:1:1 normal saline:glycerol:propylene glycol.

The amount of carrier material employed in connection with the subject invention may vary, as one skilled in the art will recognize upon being placed in possession of the subject disclosure, and may be dependent on such factors as the particular carrier used, the type and nature of the compound to be delivered, the age, weight, cells or patient (animal) to be treated, the particular diagnostic, therapeutic or other application intended (including the disease state, if any, to be treated), and the organic halide (if any) used. Generally, smaller amounts of carrier are employed, and increased until the desired delivery result is obtained. Representative amounts are set forth in the examples herein. Of course, higher or lower amounts may be employed, as will be recognized by the skilled artisan.

A wide variety of different methods may be used to mix the organic halide, compound to be delivered, and/or carrier, and incorporate the compound to be delivered with or into any organic halide and/or carrier. Methods include shaking by hand, vortexing, mechanical shaking (e.g. with an Espe Cap-Mix, Espe Medizin-Dental GMBH, Seefeld, Germany), extruder (e.g. with a Lipex Biomembranes Extruder Device, Vancouver, B.C., Canada), microemulsification (e.g. with a Microfluidizer, Microfluidics Corp., Newton, Mass.), mixing with static in line mixers (Cole-Parmer Instrument Co., Vernon Hills, Ill.), spray drying (e.g. with a Bucchi spray dryer, Brinkmann Ind., Inc., Westbury, Mass.), mechanical stirring/mixing (e.g. with a Silverson Mixer, Silverson Machines, Ltd., Waterside Chesham Bucks, England) and sonication. In general it is desirable to mix the carrier (e.g. lipids such as DPEPC and DOPE) together with the organic halide prior to adding the compound to be delivered (e.g., DNA). After adding the DNA, a carrier and organic halide association will form with the DNA. If desired, additional mixing may then be performed by one of the above techniques. In some other situations, e.g. calcium precipitation, the DNA, organic halide, and cations may be added together with one or more stabilizing agents to form the precipitates of DNA/carrier/organic halide in a single step process. Again, one of a variety of mixing techniques as described above may be employed to decrease the size of the resultant particles.

The carriers may be combined with the compound to be delivered and the organic halide in varying amounts and percentages, as will be understood by those skilled in the art once armed with the present disclosure. Typically, smaller amounts of all compositional components are employed, and increased selectively in increments until the desired delivery effect is achieved. Generally, when the compound to be delivered is employed with a carrier, the ratio of organic halide and any carrier to the compound to be delivered may be from about 6 to about 1, to about 1 to about 6, and variations therebetween. Preferably, the carrier to compound to be delivered ratio is about 6 to about 1. Representative ratios are provided by the examples herein. Of course, other ratios can be suitably employed over a wide variety of ranges as desired, as will be recognized by the skilled artisan, and all such ratios are within the scope of the present invention.

The resulting composition may be stored as a lyophilized, or freeze dried, material for inhalation or hydration prior to use or as a preformed suspension. Cryopreservatives known to skilled artisans once armed with the present disclosure may be used in the lyophilized form of the composition. To prevent agglutination or fusion of vesicles as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG polymers having a molecular weight of from about 400 to about 10,000, with PEG polymers having molecular weights of about 1000, 3000 (such as PEG3350) and 5000 being preferred. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life. As noted above, if desired, the lyophilized composition may be (and preferably is) rehydrated prior to use.

The route of administration varies depending upon the intended application. For cell culture applications, the composition is typically contacted with the cells by, for example, adding it to the cell culture media or applying it directly to the cells. Advantages of this invention for transfection in cell culture media include high activity in serum containing media and a single step transfection process with higher efficiency transfection than in other more complicated systems. Indeed, the present invention makes it possible to obtain gene expression in cells in which transfection was otherwise impossible or extremely difficult. For in vivo administration the composition may simply be injected, such as intravenously, intravascularly, intralymphatically, parenterally, subcutaneously, intramuscularly, intranasally, intrarectally, intraperitoneally, interstitially, into the airways via nebulizer, hyperbarically, orally, topically, or intratumorly, or otherwise administered.

One or more targeting ligands may be incorporated into the carrier to facilitate uptake by selected cells. Targeting ligands include, for example, peptides, antibodies, antibody fragments, glycoproteins, carbohydrates, etc. Preferably, the targeting ligand is covalently attached to the carrier, e.g., to a lipid. Preferably the targeting ligand is attached to a linker which is attached to the surface of the carrier. Preferred linkers are polymers, for example, bifunctional PEG having a molecular weight of about 1,000 to about 10,000, most preferably 5,000. Generally, the targeting ligand is incorporated into the carrier from about 0.1 mole % to about 25 mole %, preferably about 1 mole % to about 10 mole %.

In this regard, the composition may be targeted to coated pits of selected cells and taken up into endosomes via a process of receptor mediated endocytosis. If desired ultrasound energy may be applied to the target tissue to facilitate gene expression. For inhalation the composition may be inhaled via a nebulizer or via an inhaler. Also, oral or rectal routes may be utilized to administer these composition. Transcutaneous application may be accomplished by the use of penetration enhancing agents with or without the application of sonophoresis (e.g. low frequency sound in range of 10 to 100 Khz) or iontophoresis. Also interstitial (e.g. intratumoral) and subcutaneous injection may be performed to administer the composition.

Also the invention may be practiced with gene gun techniques or electroporation, or in combination with other transfection techniques known in the art. In either case, ultrasound may be applied to the cells before, after, and/or simultaneously with the gene gun or electroporation procedure. The electric fields of electroporation may also be pulsed in tandem with the ultrasound energy to further increase the efficacy of transfection.

The compounds and compositions may, in accordance with the present invention, be administered alone, or together with ultrasound. If ultrasound is employed, it is administered at a frequency and energy level sufficient to assist in inducing the uptake of the compound to the cell. Where organic halide gaseous precursors are employed, the ultrasound may be applied at a frequency and energy level sufficient to convert the organic halide gaseous precursor to a gas. For example, the present invention of administering compounds to cells includes administering a nucleotide sequence (or other compound of interest to be delivered) to a cell and applying ultrasound to the cell for a time effective to induce the uptake of the nucleotide sequence (or other compound). Enhanced delivery of the compound (and expression of the nucleotide sequence, in the case of nucleotide sequence being administered) results. Ultrasound is carried out at a frequency, energy level, and duty cycle for a therapeutically effective time in which to induce delivery of the nucleotide sequence. Suitable frequencies, energy levels and duty cycles are disclosed herein, and other ranges will be readily apparent to one skilled in the art once armed with the present disclosure.

The methods of the present invention permit the delivery of sequences coding for the gene expression of a variety of proteins, and antisense sequences which block gene expression of a variety of proteins. As a result, a number of diseases may be treated with the transfection methods of the present invention. In addition, the methods of transfection of the present invention may be practiced in vivo, ex vivo, and in vitro.

Administration of a nucleotide sequence by a microsphere utilizes a nucleotide sequence attached to a microsphere in various positions relative to the microsphere as set forth above. While not intending to be bound by any particular theory or theories of operation, the microsphere approach is believed to rely on the fusion of the nucleotide sequence containing microsphere with the plasma membrane of the host cell. The nucleotide sequence subsequently traverses the cytoplasm and enters the nucleus. The use of a microsphere results in little toxic effects to the host cell, tissue, and the patient (in the case of in vivo use).

Intracellular delivery and transfection in accordance with the methods of the present invention may be performed in vivo, ex vivo, and in vitro. Included within the above three methods is human gene therapy including wherein cells to be treated are excised from a patient. The cells are treated with an appropriate nucleotide sequence and transfection with ultrasound is carried out in cell culture. The transfected cells are analyzed for gene expression of the appropriate protein. The successfully transfected cells, measured by gene expression, are then returned to the body of the patient. Transfection with ultrasound thereby results in the treatment of diseases by gene therapy. Diseases to be treated with the methods of the present invention include and are not limited to acquired immune deficiency syndrome, autoimmune diseases, chronic viral infection, hemophilia, muscular dystrophy, cystic fibrosis, diabetes, atherosclerosis, liver cancer, lung cancer, prostate cancer, ovarian cancer, brain cancer, kidney cancer, melanoma, neuroblastoma, and breast cancer. Many other diseases may, of course, be treated with the methods of the present invention, as will be apparent to the skilled artisan upon reading the present disclosure, and the treatment of all such diseases are to be considered within the scope of the present methods.

The use of heat, for example in the form of ultrasound, lithotripsy shock waves, and increased body temperature, in the present invention is useful in aiding the delivery of compounds, such as, for example, nucleotide sequences, into cells for therapeutic purposes. The introduction of a nucleotide sequence into the cell is the first step in incorporating the sequence into the genome. Such transfection techniques may be useful in conjunction with testing the range of ultrasound frequency useful in inducing the delivery of compounds, including nucleotide sequences, to cells.

Each of the methods of the present invention include administering all or part of a sense or an antisense sequence for insulin (Giddings and Carnaghi, *Mol. Endocrinol.* 1990

4:1363-1369), Bcl 2 (Tsujimoto, Y., et al., *PNAS, USA* 1986, 83:5214-5218), human leukocyte antigen (Trucco, G., et al., *Diabetes* 1989, 38:1617-1622), thymidine kinase (Axel, R., et al., *J. Supramol. Struct.* 1979, 8 (Suppl. 3):41), HLA-B7, Factor VIII (Higuchi, M., et al., *Genomics* 1990, 6:65-71, ras/p53 (Arai, N., et al., *Mol Cell Biol* 1986, 6:3232-3239, Mitsudomi, T., et al., *Chest* 1993, 104:362-365), high density lipoprotein (hdl), leutinizing hormone releasing hormone (Maier, C. C., et al., *Cell Mol Neurobiol* 1992, 12:447-454) and leutinizing hormone releasing hormone antagonist, antitumoral agents such as and not limited to insulin-like growth factor-1 (IGF-1, Barnes, M., et al., *Obstetrics and Gynecology* 1997, 89:145-155), anti-IGF-1 (human IGF-1 gene fragment from published patent application GB2241703 GenBank accession number A29119), anti-k-ras (dog spleen mRNA 212 nucleotides GenBank accession number S42999), anti-c-fos (*Rattus norvegicus* Sprague Dawley c-fos gene, 5' flanking region GenBank accession number U02631), bcr-abl (Barnes, M., et al., *Obstetrics and Gynecology* 1997, 89:145-155), c-myc (mouse c-myc gene, exons 1 and 2 GenBank accession number L00038, J00373, and J00374), c-myc promoter (Barnes, M., et al., *Obstetrics and Gynecology* 1997, 89:145-155), erbB-2 promoter (Barnes, M., et al., *Obstetrics and Gynecology* 1997, 89:145-155), erbB2 promoter-cytosine deaminase (human c-erb B2/neu protein gene, partial cDNA (cds) GenBank accession number M95667), and antivirals such as and not limited to anti-human papilloma virus (HPV), anti-human immunodeficiency virus (HIV) such as HIVenv+rev (HIV type 1, isolate BTSPR, env gene, C2V3 region, partial cds GenBank accession number U53195), tar/Td-rev (HIV type 1 rev-1 gene, 5' end GenBank accession number M38031, synthetic HIV1 TAR, 5' end GenBank accession number M27943), ribozyme, zeta-chimpanzee receptor, and the like, and all or part of a sequence encoding cytokines such as and not limited to interleukin 2 (IL-2) (human brain MRNA 418 nucleotides GenBank accession number S77835), interleukin 4 (Arai, N., et al., *J Immunol* 1989, 142:274-282), interleukin 7 (human gene, exon 1 GenBank accession number M29048), interleukin 12 (mouse 5' flanking region of IL-12 p35 gene GenBank accession number D63334), interleukin 4 (human IL-4 gene, complete cds GenBank accession number M23442), interleukin 6 (human gene for nuclear factor NF-IL-6 GenBank accession number X 52560); gp130 (LIF receptor/IL-6 receptor complex component MRNA 150 nucleotides GenBank accession number S80479), interleukin 6 receptor, granulocyte macrophage colony stimulating factor (GM-CSF) (human GM-CSF gene, 5' flanking/promoter region GenBank accession number U31279), interferon including interferon gamma (human immune IFN-γ gene, complete cds GenBank accession number J00219, M37265, V00536), tumor necrosis factor beta, TNF-β, (human 5' sequence of TNF-β gene GenBank accession number X59351)), vascular endothelial growth factor (VEGF), human growth hormone (hGH, Fidders, J. C., et al., *Proc Natl Acad Sci* (USA) 1979 76:4294-4298), colony stimulating factor, Factor VIII, Factor IX, Factor X, and the like. Other sequences useful in the methods of the present invention include ribozymes including catalytic RNA which may have a hammerhead secondary structure (Bratty, et al., *Biochim. Biophys. Acta* 1993 1216:345-349 and McKay, D. B., *RNA* 1996 2:395-403), c-myc, c-myb, tumor suppressor genes such as and not limited to human tumor antigen p53 (5' end GenBank accession number M26864), genes offering chemoprotection such as and not limited to those encoding multidrug resistance protein (MDR) (human mdr1 gene GenBank accession number X 78081), genes for antigen overexpression such as and not limited to HLA-B7 (beta 2 microglobulin) (mouse MHC class I HLA-B7 gene, 5' flanking region GenBank accession M35971), carcinoembryonic antigen (CEA) (human 5' region GenBank accession number U17131), suicide genes such as and not limited to thymidine kinase (TK) (human TK gene encoding TK and promoter region GenBank accession number M13643), Ras, gene complementation genes such as and not limited to cystic fibrosis transmembrane conductance regulator (CFTR) (human CFTR gene, exon 1 GenBank accession number M55106 and M55499), adenosine deaminase (ADA) (human ADA gene, complete cds GenBank accession number M13792), glucocerebrosidase, IRAP/TK (human MRNA for IRAP GenBank accession number X53296), vascular endothelial growth factor (VEGF) (mus musculus VEGF gene, partial cds and promoter region GenBank accession number U41383), LDLR (human LDL receptor gene fragment GenBank accession number M60949), Fanconi Anemia Complementation Group C (FACC) (human FACC gene, 5' region GenBank accession number X83116), p47-phox (human P47 LBC oncogene MRNA, complete cds GenBank accession number U03634), Factor IX (human Factor IX gene, exon 1 GenBank accession number K02048), α-1 antitrypsin (human α-1 antitrypsin gene S variant, complete cds GenBank accession number K02212), α-1 iduronidase (human iduronidase gene sequence GenBank accession number M88001), and iduronate sulfatase (Ids) (Mus musculus Ids MRNA, complete cds GenBank accession number L07921), and gene markers such as and not limited to NeoR and LacZ, (bacteriophage T4 td gene, exon 2, 3' end; ORF2, complete cds and ORF3, 5' end GenBank accession number M22627, and cloning vector pZEO (isolate SVLacZ) β-galactosidase (lacZ) gene, phleomycin/zeocin-binding protein (ShBle) gene, (complete cds GenBank accession number L36850).

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, Thompson, L., *Science,* 1992, 258, 744-746. Nucleotide sequences for the above-identified proteins are available in the scientific literature, including GENBANK, and are known to skilled artisans.

In addition to a coding sequence or antisense sequence, the nucleotide sequence administered to cells may have additional sequences to assist in the expression of the sequence. Suitable expression vectors, promoters, enhancers, and other expression control elements are known in the art and may be found in Sambrook et al., *Molecular Cloning: A Laboratory Manual,* second edition, Cold Spring Harbor Laboratory Press, Cold Spring Harbor, N.Y. (1989). Promoters such as and not limited to SV40, RSV, CMV, cd5k, IL5R α pgk-1, srα, TK, and the like are useful in the present invention. Transcription and/or translation control elements may be operatively linked to the sequence. For example, in an upstream position, a promoter may be followed by a translation initiation signal, comprising a ribosome binding site and an initiation codon, and in a downstream position may be a transcription termination signal. The transcription and translation control elements may be ligated in any functional combination or order. The transcription and translation control elements used in any particular embodiment of the invention will be chosen with reference to the type of cell into which the expression vector will be introduced, so that an expression system is created. The selection of promoters, enhancers, and other expression control elements and the preparation of expression vectors suitable for use in the present invention will be well within the ambit of one skilled in the art once armed with the present disclosure. Also, introduction of the expression vector incorporating a sequence into a host cell can be performed in a variety of ways known in the art.

Mammalian cells may be primed to be more susceptible to uptake of DNA for gene therapy by the addition of various media, buffers, and chemicals known to those of skill in the art and set forth in Sambrook, supra. Administration of nucleotide sequences in vivo may include, if desired, more than one sequence. For example, a single carrier may contain more than one sequence or carriers containing different sequences may be co-administered. In addition, one sequence may be delivered in a carrier and another naked sequence coadministered. Additional sequences, such as promoter sequences, may be delivered together with a sequence for therapeutic delivery, to increase expression thereof. For example, a heat shock protein nucleic acid sequence is an example of an upregulating gene sequence which may be used to increase expression of a second gene sequence.

A wide variety of compounds (in addition to genetic material) may also be delivered to cells in accordance with the methods of the invention. Such other compounds include various other bioactive agents. As used herein, "bioactive agent" refers to any substance which may be used in connection with an application that is therapeutic or diagnostic in nature, such as, for example, in methods for diagnosing the presence or absence of a disease in a patient or in methods for the treatment of disease in a patient. As used herein, "bioactive agent" refers also to substances which are capable of exerting a biological effect in vitro, in vivo, and/or ex vivo. The bioactive agents may be neutral, or positively or negatively charged, etc., as desired. Examples of suitable bioactive agents include diagnostic and pharmaceutical agents, including drugs, synthetic organic molecules, proteins, peptides, vitamins, steroids, steroid analogs; and also include genetic material, including nucleosides, nucleotides and polynucleotides.

The phrase "diagnostic agent", as used herein, refers to any agent which may be used in connection with methods for imaging an internal region of a patient and/or diagnosing the presence or absence of a disease in a patient. Exemplary diagnostic agents include, for example, contrast agents for use in connection with ultrasound imaging, magnetic resonance imaging or computed tomography imaging of a patient. Diagnostic agents may also include any other agents useful in facilitating diagnosis of a disease or other condition in a patient, whether or not imaging methodology is employed.

The terms "pharmaceutical agent" or "drug", as employed herein, refer to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug, as are various other therapeutically useful organic or inorganic compounds.

Particular examples of pharmaceutical agents which may be delivered by the methods of the present invention include, but are not limited to: mitotic inhibitors such as the vinca alkaloids, radiopharmaceuticals such as radioactive iodine, phosphorus and cobalt isotopes; hormones such as progestins, estrogens and antiestrogens; anti-helminthics, antimalarials and antituberculosis drugs; biologicals such as immune sera, antitoxins and antivenins; rabies prophylaxis products; bacterial vaccines; viral vaccines; aminoglycosides; respiratory products such as xanthine derivatives, theophylline and aminophylline; thyroid therapeutics such as iodine salts and anti-thyroid agents; cardiovascular products including chelating agents and mercurial diuretics and cardiac glycosides; glucagon; blood products such as parenteral iron, hemin, hematoporphyrins and their derivatives; targeting ligands such as peptides, antibodies, and antibody fragments; biological response modifiers such as muramyl dipeptide, muramyl tripeptide, microbial cell wall components, lymphokines (e.g. bacterial endotoxin such as lipopolysaccharide and macrophage activation factor); subunits of bacteria (such as Mycobacteria and Cornebacteria); the synthetic dipeptide N-acetyl-muramyl-L-alanyl-D-isoglutamine; antifungal agents such as ketoconazole, nystatin, griseofulvin, flucytosine (5-fc), miconazole, and amphotericin B; toxins such as ricin; immunosuppressants such as cyclosporins; and antibiotics such as β-lactam and sulfazecin; hormones such as growth hormone, melanocyte stimulating hormone, estradiol, beclomethasone dipropionate, betamethasone, betamethasone acetate, betamethasone sodium phosphate, betamethasone disodium phosphate, betamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, and vasopressin, as well as their derivatives; vitamins such as cyancobalamin neionic acid; retinoids and derivatives such as retinol palmitate and α-tocopherol; peptides and enzymes such as manganese superoxide dismutase and alkaline phosphatase; anti-allergens such as amelexanox; anticoagulation agents such as phenprocoumon and heparin; tissue plasminogen activators (TPA), streptokinase, and urokinase; circulatory drugs such as propranolol; metabolic potentiators such as glutathione; antibiotics such as p-aminosalicyclic acid, isoniazid, capreomycin sulfate cycloserine, ethambutol hydrochloride ethionamide, pyrazinamide, rifampin, streptomycin sulfate dapsone, chloramphenicol, neomycin, ceflacor, cefadroxil, cephalexin, cephadrine erythromycin, clindamycin, lincomycin, amoxicillin, ampicillin, bacampicillin, carbenicillin, dicloxacillin, cyclacillin, picloxicillin, hetacillin, methicillin, nafcillin, oxacillin, penicillin (G and V), ticarcillin rifampin and tetracycline; antivirals such as acyclovir, DDI, Foscamet, zidovudine, ribavirin and vidarabine monohydrate; antianginals such as diliazem, nifedipine, verapamil, erythritol tetranitrate, isosorbide dinitrate, nitroglycerin (glyceryl trinitrate) and pentaerythritol tetranitrate; antiinflammatories such as difluisal, ibuprofin, indomethacin, meclofenamate, mefenamic acid, naproxen, oxyphenbutazone, phenylbutazone, piroxicam, sulindac, tolmetin, aspirin, and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine, and opium; cardiac glycosides such as deslanoside, digitoxin, digoxin, digitalin, and digitalis; neuromuscular blockers such as atracurium nesylate, gallamine triethiodide, hexaflorenium bromide, metrocurine iodide, pancurium bromide, succinylcholine chloride (suxamethonium chloride), tubocurarine chloride and vecuronium bromide; sedatives such as amorbarital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, secobarbital sodium, tulbutal, temazepam and trizolam; local anesthetics such as bupivacaine hydrochloride, chloroprocaine hydrochloride, etidocaine hydrochloride, lidocaine hydrochloride, mepivacaine hydrochloride, procaine hydrochloride, and tetracaine hydrochloride; general anaesthetics such as droperidol, etamine hydrochloride, methohexital sodium and thiopental sodium; antineoplastic agents such as methotrexate, fluorouracil, adriamycin, mitomycin, ansamitomycin, bleomycin, cystein arabinoside, arabinosyl adenine, mercaptopolylysine, vincristine, busulfan, chlorambucil, azidothymidine, melphalan (e.g. PAM, L-PAM or phenylalanine mustard), mercaptopurine, mitotane, procarbazine hydrochloride dactinomycin (actinomycin D), danorubicin hydrochloride, dosorubicin hydrochloride, taxol, plicamycin (mithramycin), aminoglutethimide, estramustine phosphate sodium, flutamide, leuprolide acetate, leuprolide acetate, megestrol acetate, tamoxifen citrate, testolactone, trilostane, amsacrine (m-AMSA), asparaginase, etoposide (VP-16), interferon α-2a, interferon α-2b, teniposide (VM-26), vinblastine sulfate (VLB), vincristine sulfate, hydroxyurea, procarbaxine, and dacarbazine.

Although a wide variety of compounds, including nucleotides, may be delivered in accordance with the present invention, preferably the nucleotides are less than about 10,000 bases (or base pairs) in length, more preferably between about 20 to about 10,000 bases (or base pairs) in length, even more preferably between about 2,000 and about 8,000 bases (or base pairs) in length, and most preferably between about 4,000 and 6,000 bases (or base pairs) in length. Other (non-nucleotide) compounds or bioactive agents to be delivered are preferably less than about 5000 kilodaltons (5000 kD) in molecular weight, more preferably between about 10 and about 1000 kD, even more preferably between about 100 and about 500 kD. As one skilled in the art will recognize, however, larger and smaller sized compounds may also be delivered in accordance with the present invention.

The useful dosage of nucleotide sequences or other compounds to be administered or delivered, as well as the mode of administration, will vary depending upon type and nature of the compound to be delivered, the age, weight, cells or patient (animal) to be treated, the particular diagnostic, therapeutic, or other application intended (including the disease state, if any, to be treated), and the organic halide (if any) and carrier (if any) employed. Typically, dosage is initiated at lower levels and may be increased until the desired therapeutic effect is achieved. The desired dosage, including any therapeutically or diagnostically effective dosage amounts, will be well within the ambit of one skilled in the art, armed with the prevailing medical literature and with the present disclosure. Representative amounts are provided in the examples herein. Of course, higher or lower amounts may be employed, as will be recognized by the skilled artisan.

As one skilled in the art would recognize, administration of compositions of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, or intratumorly, using a variety of dosage forms. One method of topical administration is the addition of a nucleotide sequence (or other compound to be delivered), preferably in a carrier such as and not limited to a hydrogel, applied to the outside of a balloon catheter. The catheter is inserted into the blood stream of a patient. Once the balloon of the catheter reaches the location to which the sequence is to be administered, the balloon is pumped up and the sequence-containing hydrogel adheres to the blood vessel surface thus delivering the sequence. In addition, ultrasound may be applied to the cells endoscopically and intravascularly, for example, as well as, of course, applied externally.

A number of transfection and other intracellular delivery techniques are possible in accordance with the methods of the present invention employing the subject methods and the organic halides and/or carriers as disclosed herein. Two methods, using calcium phosphate and viral vectors, are indirect methods of introducing the nucleotide sequence into cells because they involve the passive uptake of the nucleotide sequence by the cell which is to be transfected.

Calcium phosphate coprecipitation is a chemical-mediated indirect method of transfection. The nucleotide sequence (or other compound to be administered) is introduced into mammalian cells, for example, by coprecipitation of the sequence with calcium phosphate, calcium chloride, calcium hydroxybutyrate, and the like; then the mixture is presented to the cells. The purified nucleotide sequence is mixed with buffers containing phosphate and calcium chloride which results in the formation of a very fine precipitate, and the mixture is presented to the cells in culture. A protocol for cells that grow attached to a substratum as set forth in Keown, W. A., et al., "Methods for Introducing DNA into Mammalian Cells," in *Methods in Enzymology*, Vol. 185, *Gene Expression Technology*, Ed., Goeddel, David V., pp. 527-537, Academic Press, Inc., New York, N.Y., 1991 is incorporated herein by reference in its entirety. Briefly, on day 1, cells are seeded at $2-3 \times 10^4$ cells/cm$^2$ in normal growth medium and allowed to attach. At the time of transfecting, the cells should be 80-90% confluent. On day 2, the nucleotide sequence-calcium phosphate coprecipitate is prepared, mixed and allowed to stand at room temperature for about 30 minutes. The nucleotide sequence is added to TE buffer (10 mM tris, 1 mM EDTA Ph 8.0), 2×HBAS (Hanks' balanced slats, 1.4 mM $Na_2HPO_4$, 10 mM KCl, 12 mM glucose, 275 mM NaCl, and 40 mM HEPES, ph 6.95), and 2M $CaCl_2$ (calcium chloride in 10 mM HEPES, pH 5.8). The medium is removed from the cells and replaced with fresh medium. The precipitate is mixed gently by shaking or pipetting and added directly to the medium in dishes containing cells. The cells are incubated at 37° C. for 4 hours. The medium containing the precipitate is removed and dimethyl sulfoxide in 1×HBS. After 2 minutes, 4 ml of serum-free medium is added to each dish. The mixture is aspirated, washed twice with serum-free medium, and medium is added and incubated overnight at 37° C. The cells are trypsinized and the contents of each plate is split into 3-4 new plates. Selection may be applied for stable transfectants, in which selective medium may be used at this time or a day later.

The present invention employing the methods of the invention and the organic halides and/or carriers may also be useful concurrently with microinjection and electroporation. Microinjection involves the direct microinjection of nucleotide sequences into the nucleus of a host cell. Microinjection does not expose the nucleotide sequence to the cytoplasm or organelles within it. This is beneficial since considerable damage may result to the DNA during transit from the cell exterior to the nucleus. Electroporation involves electric field-mediated nucleotide sequence transfection. When membranes are subjected to an electric field of sufficiently high voltage, regions of the membrane undergo a reversible breakdown, resulting in the formation of pores large enough to permit the passage of nucleotide sequences. Electroporated nucleotide sequences remain free in the cytosol and nucleoplasm. Very few copies of transfected nucleotide sequences may be introduced with electroporation. Cells susceptible to electroporation include, for example, lymphocytes, hematopoietic stem cells, and rat hepatoma cells.

"Ultrasound", "Sonoporation", and similar terms, refer to pulses of sound energy, preferably repetitive pulses, sufficient to assist in inducing the delivery of a compound into a cell, and, if desired, the formation of a gas from a gaseous precursor. Preferably, the ultrasound is in the frequency range of from about 10 kilohertz to less than about 50 megahertz and at an energy level of from about 200 milliwatts/cm$^2$ to about 10 watts/cm$^2$. While not intending to be bound to any particular theory of operation, the ultrasound may assist in the delivery of the compounds to the cells by inducing openings in the cell membrane, or perhaps bursting endosomes inside a cell allowing compounds to escape. Indeed, cells may be induced to take up (e.g., be transfected with) compounds (e.g., nucleotide sequences) with ease compared to conventional methods. Typically the ultrasound is applied by external application, via a standard clinical ultrasound device, but may also be applied in other fashions, such as endoscopically and intravascularly, as described above. The use of ultrasound in connection with the present invention may, in certain embodiments, be preferred. However, as noted herein, the use of ultrasound is not necessary or critical to the operation of the methods of the invention. Thus, the subject methods may be carried out with the application of ultrasound, or without the application of ultrasound, as desired.

In accordance with the present invention, for in vivo applications, a lower frequency of sound is usually selected for cells of deep seated or thick tissues, e.g. transcutaneous application of ultrasound to cells of the deep seated muscle or organs in the abdomen or retroperitoneum. For cells of small tissues a higher frequency of sound energy is applied, e.g. for the eye. For intravascular applications, which may employ intravascular catheters equipped with ultrasound transducers for endovascular gene therapy, higher frequencies may be employed such as over about 20 megahertz. For most applications however the frequency of the sound ranges from about 500 kilohertz to about 3 megahertz, preferably from about 500 kilohertz to about 1 megahertz, more preferably about 200 kilohertz, more preferably about 40 kilohertz to about 25 megahertz, even more preferably about 10 megahertz. Compared to lithotripsy, the frequency employed in the present invention is more than about 2 or 3 orders of magnitude higher and the energy levels of the present invention are lower.

The sound energy is applied in waves of sonic energy over a given duty cycle (sometimes referred to as pulse duration) and level of intensity. Generally continuous wave ultrasound which applies a constant train of ultrasound pulses is employed. The duty cycle is selected so that the level of energy output is in a desired range. The duty cycle may be varied from between 1% and 100% meaning that the ultrasound energy will be pulsing from between 1% and 100% of the time. For example, a period of ultrasound treatment may take place over 25 minutes with three duty cycles of ultrasound, each five minutes in duration, interrupted by two periods of no ultrasound. Preferably the duty cycle is 100%, more preferably about 75%, more preferably about 50%, even more preferably about 20%, even more preferably about 15%, and even more preferably about 10%.

Ultrasound for use in the present invention is typically provided at a frequency lower than the frequency used for imaging by ultrasound. The frequency of ultrasound which is selected will vary depending upon the location of cells which are being transfected, and or other factors that will be readily apparent to one skilled in the art based upon the present disclosure.

In addition to frequency, the energy level (sometimes referred to as power intensity or power level) also has a large effect on total energy which is applied to the cells or tissue for ultrasound enhanced transfection. Suitable energy levels will be readily apparent to one skilled in the art based upon the present disclosure. Typically, the energy level settings are somewhat higher than employed in diagnostic ultrasound but may range from about 500 milliwatts/cm$^2$ to about 10 watts/cm$^2$, more preferably from about 200 milliwatts/cm$^2$ to about 10 milliwatts/cm$^2$, and more preferably of from about 50 milliwatts/cm$^2$ to about 2 watts/cm$^2$. The power level which is applied is selected so that both peak spatial temporal power and total energy deposition is generally below the cytotoxic threshold for the cells or tissue. Generally, frequencies and energy levels are applied at lower amounts, then increased until the desired cellular uptake of the administered compound is achieved.

As one skilled in the art would recognize, high energies of ultrasound may be used for hyperthermia to heat the tissue and also to directly ablate tissues with very high levels of energy. In the ultrasound enhanced transfection and gene expression of the present invention, energy levels are far below those which cause tissue ablation and below those which cause a significant hyperthermic effect. As one skilled in the art would recognize once armed with the present disclosure, energy deposition is a function of both power intensity and duty cycle. Higher spatial peak temporal average power tends to shift the bioeffect curve such that lower total energy may be applied to create a greater bioeffect. Higher energy levels and lower ultrasonic frequencies are required for penetration into deep seated tissues; conversely lower energy levels and higher ultrasonic frequencies are needed for treatment of superficial tissues or when the ultrasound transducer can be applied directly to the tissue surface. Small volume cell culture samples need less power for ultrasound enhanced transfection than large volume bioreactor chambers which may be multiple liters in size and therefore need higher energy levels to enhance gene expression. The geometry of a cell culture container will also affect the ultrasound energy requirements.

In accordance with the present invention, ultrasound energy may be used to increase the efficiency of cellular uptake of a compound (e.g. transfection) by inducing a cell to take up a compound. In addition, gene expression of a nucleotide sequence is enhanced by the application of ultrasound.

The ultrasound energy may be applied to the tissue or cells either before, simultaneously with, or after administration of the compound to the cell, preferably simultaneously with or after. Typically the ultrasound energy is applied from no more than about 48 hours prior to administration of the compound or genetic material to the cells and/or up to no more than about 48 hours after the genetic material has been administered to the cell, although longer or shorter times may be applied. More preferably, the ultrasound energy is applied at some time or at various time points from about 4 hours before administration of the compound or genetic material up to about 24 hours after administration. Most preferably the ultrasound energy is applied within about 1 hour prior to transfection up to about 12 hours post transfection.

Either one or multiple applications of ultrasound energy may be employed. The duration of ultrasound energy exposure (exposure time) will vary depending upon the power level of the ultrasound and the duty cycle. To determine the preferable duration, ultrasound is typically applied at lower exposure times, and increased until the desired cellular uptake of the compound administered is achieved. A high intensity (high power level; typically greater than about 2 watts/cm², preferably over about 5 watts/cm², and also preferably over about 10 watts/cm², depending on the pulse duration) ultrasound shock wave may require only a few milliseconds of exposure. This may also be the case when cavitation nuclei such as gas filled liposomes or perfluorocarbon emulsions are present within the medium. A very brief exposure to high energy ultrasound may be sufficient to enhance transfection. The presence of cavitation nuclei in the transfection medium will lower the cavitation threshold and therefore potentially decrease energy requirements for ultrasound enhanced transfection as well as to potentially decrease the necessary exposure time. More typically the exposure time ranges from about a few seconds to up to about an hour of ultrasound energy application to the cell to achieve most effective ultrasound enhanced gene transfection. Even more preferably the duration of ultrasound exposure ranges from about a few seconds to about a few minutes and may be repeated at various intervals during transfection. The duration of ultrasound energy exposure should be sufficient to cause the desired effect but not so long that significant cytotoxicity may result.

The effect of ultrasound enhanced transfection is independent of hyperthermia. While the application of ultrasound energy necessary to increase the efficiency of transfection may result in a few degrees centigrade increase in temperature, any increase in temperature is typically transient and the temperature rapidly returns to baseline. More preferably the temperature does not increase significantly during application of the ultrasound. An increase in temperature is typically less than about 1° C. to about 2° C. Progressively higher levels of ultrasound energy will result in progressive rises in temperature but temperature is preferably maintained below the level where significant cytotoxicity will occur (e.g. 44° C. or higher). As one may note, the sample measures the temperature in a solution of normal saline when exposed to ultrasound. The applied energy is 10 watts imparted through a 5.0 cm² transducer, or 2 W cm⁻². Sound energy from the ultrasound transducer may be simply converted to thermal energy in the aqueous milieu. The amount of energy and/or the time of exposure may be modified so as to prevent temperature-induced cell destruction.

The ultrasound energy may be applied with any of a variety of commercially available ultrasound systems. For example a Rich-Mar model 25 ultrasonic therapy apparatus (Rich-Mar Corporation, Inola, Okla.) with the center frequency residing at approximately 1.0 Mhz, in pulsed or continuous mode, may be used to practice the invention. Conventionally available transducers, power amplifiers and other component systems for practicing the invention can also be readily assembled. Wave synthesizers and pulsers may also be incorporated into the system to allow control over the pulse repetition intervals, duty cycles, etc. Advantageously, these components can also be used to modify the ultrasound pulses to employ varying frequency and amplitude effects such as CHIRP (increasing in frequency) and PRICH pulses (decreasing in frequency) waveform patterns. Ultrasonic energies can also be supplied from commercially available amplifiers, transducers and frequency generators. By way of example, a power transducer with a center frequency of 1.0 Mhz from Valpey-Fisher (Valpey-Fisher, Hopkinton, Mass.), a power RF amplifier from ENI (ENI, Rochester, N.Y.), and a function generator from Hewlett Packard (Hewlett Packard, Sunnyvale, Calif.) may be a suitable setup to accomplish the above goals. Alternatively, a pulse/function generator or an arbitrary function generator may also be used to accomplish variable pulse formats. In addition, methods that would allow for gating the various signals together, could conceivably be accomplished.

The high energy ultrasound system may also be incorporated with ultrasound imaging such as described in U.S. patent application U.S. Ser. No. 08/468,052, filed Jun. 6, 1995, and the disclosures of which are hereby incorporated herein by reference in their entirety. Also application of high energy ultrasound may be performed under other forms of conventional imaging such as endoscopy (e.g. fiberoptic), computed tomography, magnetic resonance imaging, angiography, and nuclear medicine. Such imaging may be employed, for example, to locate and identify in a patient the cells to which the ultrasound induced (or other) heating should be applied, or used to follow and/or locate the composition of the invention after administration to a patient.

Figure 5:
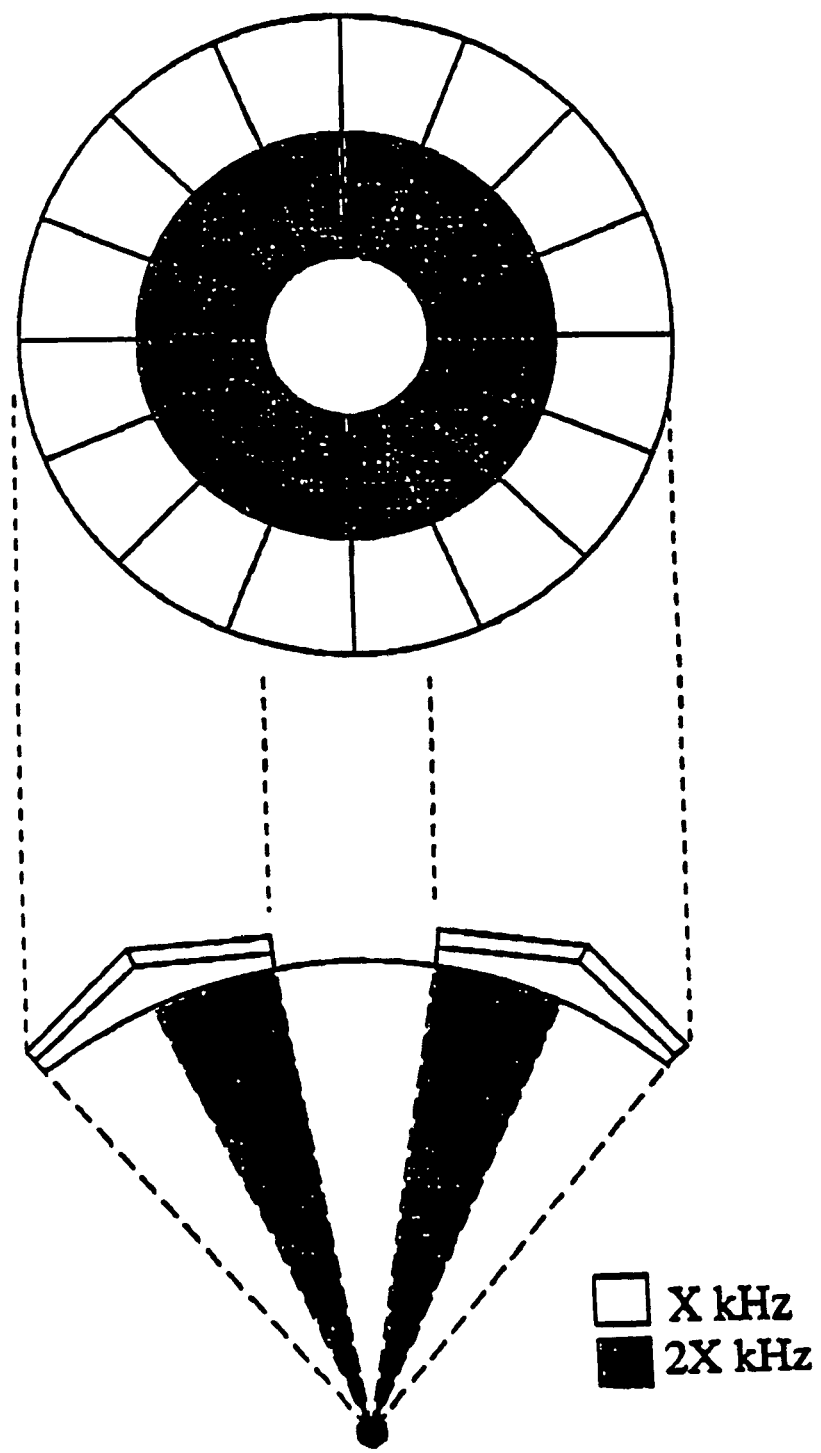
FIG. 5 is a prototype second harmonic transducer that emits X and 2X frequencies and superimposes two beams at one focal point for enhanced ultrasound effect. The transducer may be employed in conjunction with in vitro, ex vivo and in vivo delivery of compounds and compositions in accordance with the invention.
Figure 6:
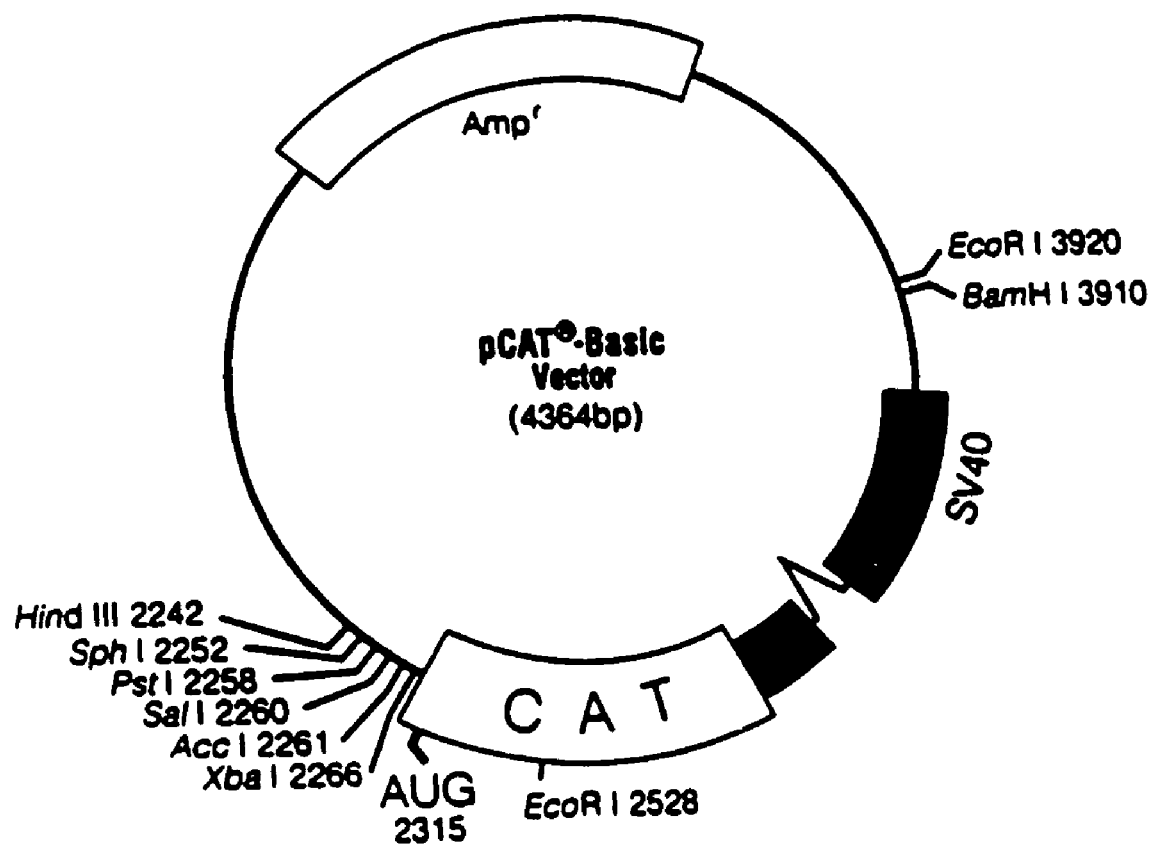
FIG. 6 is a map of the pCAT® basic vector (Promega, Montgomeryville, Pa.) used in the preparation of sequences introduced into cells in Example 10.

The ultrasound may be applied so as to effectively create second harmonic superimposition on the target treatment zone of tissue to increase the effectiveness of transfection. For example, a prototype sector-vortex phased array transducer, depicted in FIG. 5, 120 mm in diameter, which generates 750 kHz and 1.5 MHz ultrasound may be employed. As described in the reference by K. Kawabata and S. Umemura, *Ultrasonics Sonochemistry* 1996, 3:1-5, a transducer may be constructed with 32 piezoelectric (PZT) transducer elements from lead zirconate PZT material. The transducer may be constructed in two tracks such that there are 16 sectors in each track. The lower frequency ultrasound could be applied from the outer track and the higher frequency, 1.5 MHz, from the inner track. A shell may be constructed with a 120 mm radius of curvature for geometric focusing. The beam profile provided by the piezoelectric elements and spherical shape of the transducer cell assembly can be designed so as to superimpose the focal zones of the two different frequencies of ultrasound. This may result in focal acoustic power with superimposition of the lower frequency and higher frequency ultrasound sources. This results effectively in second harmonic superimposition of the ultrasound signal. While not intending to be bound by any particular theory of operation, it is believed that this ultrasound assembly will allow for improved transfection efficiency at lower total amounts of energy and thus result in reducing damage to the cell.

Skilled artisans would recognize, once armed with the present disclosure, that the two ultrasound energy sources may be at other frequencies such that the first source (low frequency) is one half the frequency of the second source. For example, 500 kHz in the outer assembly and 1 MHz in the inner assembly may be employed. A range of different frequencies may be selected such that the outer assembly is 1X and the inner assembly is 2X. Alternatively, the assemblies may be designed such that the higher frequency is in the outer assembly and the lower frequency is in the inner assembly. Alternatively still, odd harmonics may be utilized such that the outer and inner tracks may be represented by X and 3X frequencies or X and 5X frequencies. The second harmonic, ultraharmonic, or subharmonic frequencies are superimposed at the focal zone which is directed towards the target tissues or cells to be transfected. Thus, ultrasound may be administered simultaneously at two or more frequencies to result in superimposition of ultrasonic frequencies, including and not limited to second harmonic frequencies.

The present invention is also directed to a pharmaceutical kit which comprises a compound to be delivered, an organic halide and/or a carrier (including combinations thereof) for use to those desirous of delivering to a cell a compound. The compound, organic halide, and/or carrier may be mixed together or separately provided (as in, for example, separate containers, such as separate vials or packets). The pharmaceutical kit may further comprise conventional kit components known to those skilled in the art once armed with the present disclosure, such as, mixing vials, syringes, gauze, etc.

The invention is further demonstrated in the following actual Examples 1-3, 10-19, and 23, and prophetic Examples 4-9, and 20-22. The examples, however, are not intended to in any way limit the scope of the present invention.

EXAMPLES

Example 1

Effect of Ultrasound on the Temperature of an Aqueous-Based Medium in Culture Plate Well Phantoms and on Cell Viability The first phase of evaluating the effect of ultrasound was to measure the amount of heating caused by the ultrasound energy. The experimental protocol was designed to evaluate the heating in an individual well of a 6 well culture plate while exposed to ultrasound. Ultrasound was applied for 30 seconds to each well and the relationship between energy and heating is shown in Table 2 below.

TABLE 2

| Energy | Temperature increase at 10% Duty Cycle | Temperature increase at 100% Duty Cycle |
|---|---|---|
| 0.5 W/cm$^2$ | 0° C. | 0.5° C. |
| 1 W/cm$^2$ | 0° C. | 1.5° C. |
| 2 W/cm$^2$ | 0.5° C. | 2.9° C. |

A follow-up experiment was carried out to assay the cell viability after ultrasound exposure. A cell proliferation kit using sodium 3'-[1-(phenylamino-carbonyl) 3,4-tetrazolium]-bis(4-methoxy-6-nitro)benzene sulfonic acid hydrate (XTT, Boehringer-Mannheim, Indianapolis, Ind.) as the cell viability indicator was carried out to evaluate whether cell damage had occurred. In this experiment, higher absorbance is due to viable cells causing uptake of XTT. Table 3 contains the results from this study.

TABLE 3

Cell Viability as a Function of Ultrasound Power Input

| Treatment | Mean absorbance | Standard Deviation |
|---|---|---|
| No Ultrasound | 7.83 | 0.41 |
| 0.5 W/cm$^2$ 10% Duty Cycle | 7.83 | 0.41 |
| 0.5 W/cm$^2$ 100% Duty Cycle | 7.83 | 0.41 |
| 1 W/cm$^2$ 10% Duty Cycle | 7.17 | 0.75 |
| 1 W/cm$^2$ 100% Duty Cycle | 6.00 | 1.41 |
| 1.5 W/cm$^2$ 10% Duty Cycle | 7.67 | 0.82 |
| 1.5 W/cm$^2$ 100% Duty Cycle | 1.83 | 0.98 |
| 2 W/cm$^2$ 10% Duty Cycle | 6.83 | 0.75 |
| 2 W/cm$^2$ 100% Duty Cycle | 1.60 | 0.55 |

As the data in Table 3 shows, the first noticeable change in cell viability occurs with an energy of 1 W/cm$^2$ and a 100% Duty Cycle. At higher energies with a 100% duty cycle a significantly larger number of cells are destroyed.

Example 2

Effect of Ultrasound on Gene Expression in Cell Culture

Materials and Methods for Transfection and Measurement of Gene Expression

Figure 3:
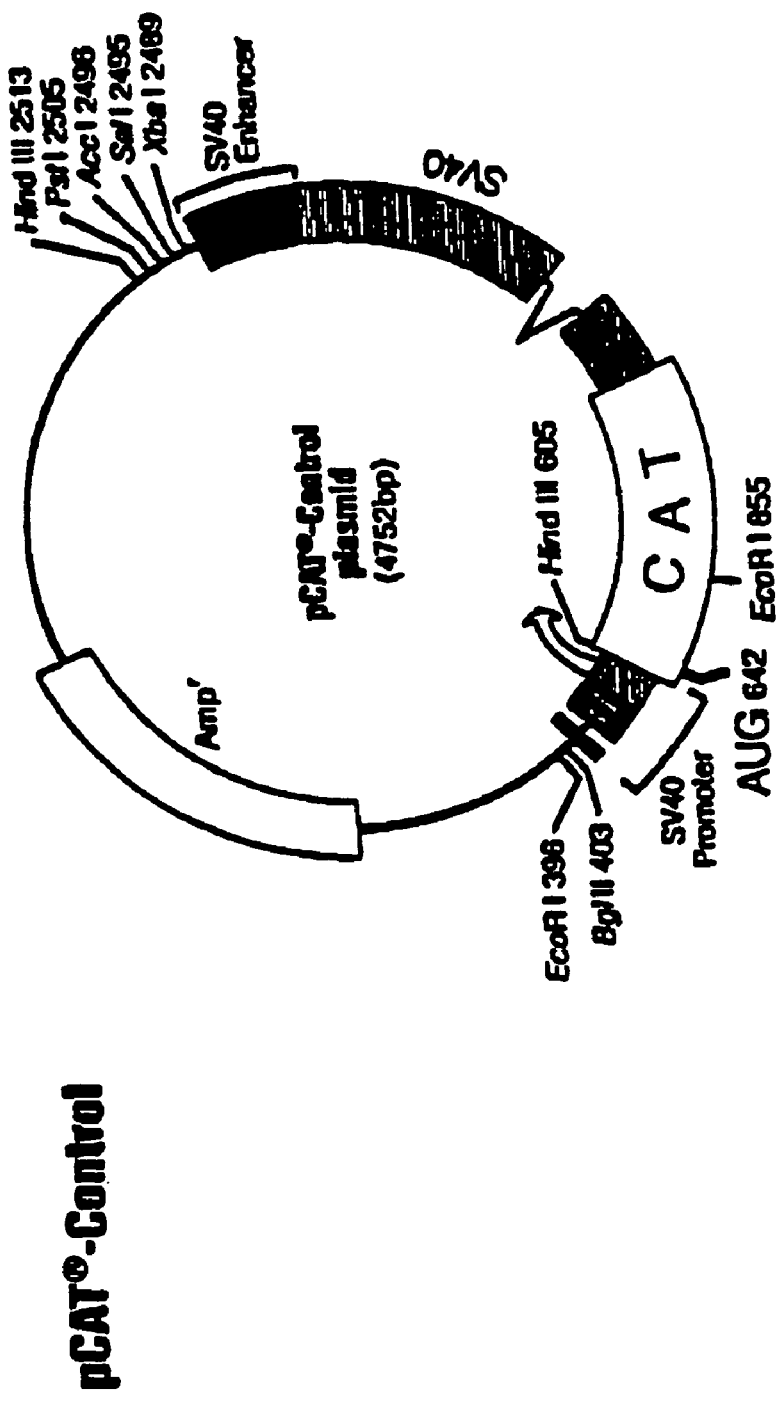
FIG. 3 is a map of the pCAT® control vector (GenBank accession number X65321) (Promega, Madison, Wis.) used in the preparation of sequences introduced into cells in Examples 2 and 3.

The DNA plasmid used was pCAT Control (GenBank accession number X65321) (Promega, Madison, Wis.) (see FIG. 3).

The plasmid was transformed into DH5-α *Escherichia coli* competent cells (Life Technologies, Gaithersburg, Md.). The cells were plated on LB agar plates (Bio 101, Vista, Calif.) that contained ampicillin (Boehringer Mannheim Biochemicals (BMB), Indianapolis, Ind.). Resistant colonies were selected, grown up and a Wizard mini-prep (Promega) plasmid DNA extraction was carried out. Plasmid DNA was cut with restriction enzyme EcoRI (BMB) and run on a 1% agarose gel (BMB). After fragments were evaluated for size, the remaining culture was used to start a large culture and a Wizard maxi-prep was carried out to produce DNA for transfection. The DNA was quantified using a Hoefer TKO-100 mini-DNA fluorometer. The DNA was then ready for use in transfections.

Cationic liposomes were made by mixing dipalmitoyl ethylphosphocholine and dioleolyl phosphoethanolamine (Avanti Polar Lipids Alabaster, Ala.). The lipid mixture was resuspended in water and then sonicated to form small liposomes.

A human cervical cancer cell line (HeLa) was obtained from the American Type Culture Collection (Rockville, Md.) and grown in EMEM culture media (Mediatech, Washington, D.C.) supplemented with calf serum (Life Technologies). These cells were used in the transfections.

The DNA/lipid complex was formed in HEPES buffered saline (HEPES 20 mmol/l, NaCl, 150 mmol/l, pH 7.4) (Sigma, St. Louis, Mo.) by mixing the lipid and DNA at a ratio of 6 parts lipid to one part DNA. This was incubated for 30 minutes at room temperature and then used for transfection.

The pCAT control plasmid encodes for the enzyme chloramphenicol acetyl transferase (CAT). This enzyme is not found in mammalian systems. The CAT expression is assayed using a CAT ELISA kit (BMB). This non-radioactive kit allows for sensitive detection of CAT expression. The kit is based on a sandwich of antibodies. A 96 well plate is coated with anti-CAT, this antibody binds the CAT in the sample. The next antibody is the anti-CAT-digoxigenin, digoxigenin is a hapten found only in the digitalis plant. The rarity of this compound makes it ideal for non-radioactive labelling. The next antibody added is an anti-digoxigenin that has been labelled with horseradish peroxidase. Horseradish peroxidase breaks down a substrate and causes a color reaction which is then read with an SLT Spectra Shell plate reader (SLT-Labinstruments Ges.m.b.h., Groedin/Salzburg, Austria). Using a standard curve, this plate reader allows for measurement of protein concentration.

Protocol

The DNA complex was formed and added at a concentration of 30 µg of lipid and 5 µg of DNA per well in a 6 well plate containing HeLa cells in 4 mls of EMEM. A Rich-Mar model 25 therapeutic ultrasound machine (Rich-Mar Corporation, Inola, Okla.) was used to apply ultrasound to the wells of the 6 well plate. The ultrasound was applied either 30 minutes before the DNA/lipid complex was added, 1 hour after the complex was added or 4 hours after the complex was added. In the first experiment, a standoff pad was used that covered the entire base of the 6 well plate and allowed sound to conduct from one well to another. The power setting was 0.5 w/cm$^2$ with a 10% duty cycle.

Three conditions were tested. No ultrasound, ultrasound applied 30 minutes before the transfection and ultrasound applied 1 hour after the transfection.

The results set forth in Table 4 are from a transfection with a 1:1 mix of dipalmitoylethyphosphocholine and dioleoyl phosphoethanolamine (Avanti Polar Lipids, Alabaster, Ala.). The transfection was carried out in the presence of serum. In addition, a negative control was added which included cells grown up not transfected with the 1:1 mix of dipalmitoylet-hyphosphocholine and dioleoyl phosphoethanolamine and without ultrasound treatment.

TABLE 4

Quantification of Gene Expression in Cells Exposed to Ultrasound

| Treatment | Cat expression (ng/ml) |
| --- | --- |
| negative control | 0 |
| no ultrasound | 15.876 |
| Ultrasound 30' pretreatment | 20.529 |
| Ultrasound 1 hour post treatment | 43.794 |

Figure 4:
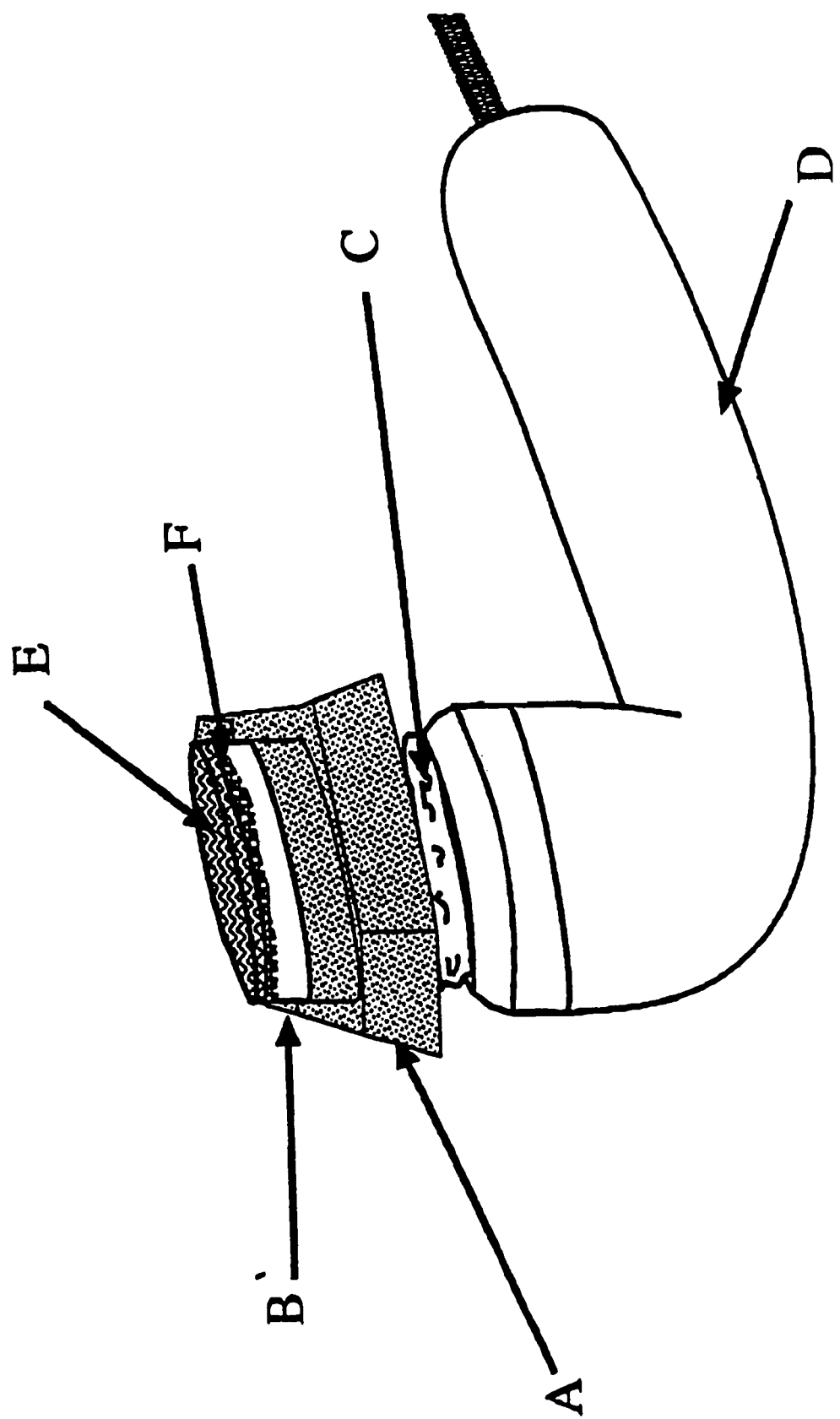
FIG. 4 is a cutaway from FIG. 1, depicting one of the six wells (B') of a six well plate B.

This experiment was repeated with a standoff pad designed to isolate the wells from each other, see FIG. 1 and FIG. 4. The base of a 6 well plate was cut away to allow transducer access and a second 6 well plate was inverted above it. 2% agarose was poured onto this mold to form a standoff pad. The standoff pad was constructed to allow for open (dead air) spaces between the portions of the standoff pad that contacted the 6 well plate, such that each well was raised above the standoff pad on a vertical support with open spaces under each of the wells where the standoff pad was cut away. The vertical supports were made of 2% agarose and conducted the sound from the ultrasound transducer. The transducer was placed below the standoff pad and sound was projected up through the pad into the each of the wells of the 6 well plate. The 6 well plate was placed upright on the standoff pad such that the cells on the bottom of the well were close to the transducer. In both experiments, the expression of the CAT protein was measured by CAT ELISA after 48 hours of incubation. Ultrasound was applied at 1 W/cm$^2$ and 100% duty cycle. The ultrasound was applied for 30 seconds on each well.

The same transfection reagent was used as in the first example. The test conditions were no ultrasound, 30 minutes before transfection, 1 hour after transfection and 4 hours post transfection. Again the transfection was carried out in the presence of serum. In addition, a negative control was added which included cells grown up not transfected with CAT/lipid complex and without ultrasound treatment. The results are shown in Table 5.

TABLE 5

| Treatment | Cat expression (ng/ml) |
| --- | --- |
| negative control | 0 |
| no ultrasound | 5.339 |
| Ultrasound 30' pretreatment | 5.339 |

TABLE 5-continued

| Treatment | Cat expression (ng/ml) |
| --- | --- |
| Ultrasound 1 hour post treatment | 10.078 |
| Ultrasound 4 hours post treatment | 4.988 |

Example 3

Application Using DNA with a Lipid Carrier and a Cavitator

The cells and the DNA/lipid complex were prepared as in Example 2. Six well plates were seeded with HeLa cells and filled with 16 ml of media as in Example 2. The lipid added was increased to 135 µg to allow for the increase in volume and the DNA was also increased to 22.5 µg per well. One hour after the complex was added, 100 µl of a liposome comprised of the lipids dipalmitoylphosphatidylcholine (DPPC), dipalmitoylphosphatidylethanolamine coupled to polyethylene glycol 5000 (DPPE-PEG5000), and dipalmitoylphosphatidic acid (DPPA), in a ratio of about 82%:8%:10% (mole %) was added to each well. The DPPE-PEG5000 was comprised of DPPE and PEG5000 in a ratio of about 20%:80% (weight %). PEG5000 refers to PEG having an average molecular weight of about 5000. In addition, a negative control was added which included cells grown up not transfected with CAT/lipid complex and without ultrasound treatment.

The six well plate was then covered with a sheet of parafilm to prevent leakage, the lid was replaced and the plate was inverted. By inverting the plate, the gas filled liposomes (cavitator) were allowed to float up to the cells, now on top of the standoff pad, plate construct. The ultrasound was applied from the bottom, however, in this case, the sound was propagated through the media to the cells. After the ultrasound exposure the plates were returned to an upright position and the parafilm removed. The plates were then incubated for 4 hours and the CAT ELISA performed the results of which are set forth in Table 6.

TABLE 6

| Treatment | Cat expression in ng/ml |
| --- | --- |
| Negative control | 0 |
| No ultrasound | 4.584 |
| 0.5 w/cm$^2$/35% duty cycle | 9.634 |
| 0.5 w/cm$^2$/100% duty cycle | 19.910 |
| 1 W/cm$^2$/100% duty cycle | 9.811 |

Example 4

Industrial Applications of Ultrasound Enhanced Transfection

A large scale bioreactor vessel containing a free suspension of cells is equipped with a flow through chamber housing an ultrasound transducer. Plasmid DNA containing the gene of interest is added to the cell suspension with and without an organic halide. As the cells circulate through the chamber 500 kilohertz ultrasound is applied with a 10 percent duty cycle at an energy level of 200 milliwatts per cm$^2$. Enhanced gene expression is attained, both with and without the organic halide. By varying the rate of flow of the cell suspension through the flow through chamber the proper ultrasound exposure time is attained for optimal transfection efficiency.

Example 5

Ex Vivo Enhancement of Gene Expression in Human Cells

Plasmaphoresis is used to harvest the T cells of a patient with metastatic malignant melanoma. The T cells are placed in tissue culture and incubated with granulocyte macrophage colony stimulating factor (GMCSF) to increase multiplication of the lymphocytes. After sufficient cell densities have been achieved the gene for interleukin-2 (IL-2) is added to the cells with a cationic liposomal vector, with and without an organic halide. One hour later 1 megahertz ultrasound energy is applied at a power level of 0.5 watts with a 10% duty cycle for a duration of 5 minutes. Twenty-four hours later the cells are infused back into the patient in an effort to treat the metastatic tumors. Promising results in the form of a perceptible decrease in tumor mass are observed, both with and without the organic halide. Additional testing also reveals enhanced IL-2 expression in the treated cells.

Example 6

Therapeutic Applications of Ultrasound Mediated Gene Delivery: Duchenne's Muscular Dystrophy In a patient with Duchenne's Muscular Dystrophy plasmid DNA encoding the gene for dystrophin is injected at multiple sites into the muscles of the thighs and legs, with and without an organic halide. Ultrasound is then applied to the thighs and legs using silicone gel as couplant between the transducer and the patient's skin. The frequency is 200 kilohertz with a 10% duty cycle and a power level of 1 watt. The transducer remains for about 2 to 3 minutes over any one location on the skin. Enhanced expression for the gene for dystrophin is attained resulting in increased muscle strength, both with and without the organic halide.

Example 7

Therapeutic Applications of Ultrasound Mediated Gene Delivery: Atherosclerotic Heart Disease A patient with atherosclerotic disease has marked narrowing of the left anterior coronary artery. A balloon angioplasty catheter coated with a hydrogel material binding the gene for vascular endothelial growth factor (VEGF), both with and without an organic halide, is placed at the site of arterial stenosis and the balloon is inflated to a pressure of 9 atmospheres. An endovascular ultrasound catheter is placed inside the vessel at the region where the angioplasty was performed and ultrasound energy is applied. The frequency is 20 megahertz at 1 watt per $cm^2$ with 15% duty cycle for 3 minutes. Enhanced gene expression of VEGF is observed with diminished propensity to restenosis at the angioplasty site; both with and without the organic halide.

Example 8

Therapeutic Applications of Ultrasound Mediated Gene Delivery

Similarly to Example 7 angioplasty is performed in a patient using a balloon catheter coated with the gene for VEGF, and with and without an organic halide, but in this case the ultrasound energy is applied transcutaneously with a 1 megahertz focused transducer equipped with both imaging and therapeutic elements. The therapeutic 1 megahertz sound is applied at an energy level of 500 milliwatts/$cm^2$ using a 20% duty cycle for a period of 5 minutes. The energy is focused upon the angioplasty site. Again enhanced VEGF gene expression is observed and decreased propensity to restenosis, both with and without the organic halide.

Example 9

Therapeutic Applications of Ultrasound Mediated Gene Delivery

Colonoscopy is performed in a patient with genetic predisposition to colon cancer. A region of epithelial metaplasia is identified in the descending colon. An ultrasound transducer equipped with a semipermeable membrane and drug storage reservoir containing the gene for Bcl 2 with a liposomal vector, both with and without an organic halide, is positioned over the area of epithelial metaplasia and ultrasound energy is applied at a frequency of 500 kilohertz with an energy level of 500 milliwatts/$cm^2$ and 10% duty cycle for a period of 3 to 5 minutes, to deliver the Bcl 2 gene to the cells in the region. On follow-up colonoscopy 8 weeks later the epithelial metaplasia has decreased significantly, particularly where an organic halide is employed in the administration process. Further testing reveals enhanced Bcl 2 expression in the region, both with and without the organic halide employed in the delivery process.

Example 10

Transfection Efficiency of DPEPC/DOPE with and without Organic Halides

Dipalmitoylethylphosphocholine (DPEPC) (Avanti Polar Lipids, Alabaster, Ala.) was mixed with dioleoylphosphatidylethanolamine (DOPE) (Avanti Polar Lipids, Alabaster, Ala.) at a 1:1 (w:w) ratio in 10 ml of deionized water at a lipid concentration of 1 mg per ml. 100 microliters of n-perfluorohexane (PCR, Inc., Gainesville, Fla.) was added and mixed by shaking for 5 minutes on a Heavy Duty #6 Wig-L-Bug (Crescent Dental, Lyons, Ill.). The mixture was then extruded five times through two 0.8 µm filters in a Lipex Biomembranes Extruder Device (Vancouver, BC, Canada). Particles without a fluorinated organic halide were sonicated for 10 minutes at room temperature in a bath sonicator. The mixture was then diluted in HEPES buffered saline at a ratio of 30 µl of lipid mix to 70 µl of HBS per well. pCMVCAT (Life Technologies, Inc., Gaithersburg, Md.) containing the gene for chloramphenicol acetyl transferase and the promoter from human cytomegalovirus (CMV) was used to transfect HeLa cells. pCMVCAT may be produced in accordance with the methods set forth in Foeeking and Hofstetter, *Gene* 1986 45:101-105, incorporated herein by reference in its entirety.

The pCAT® (Promega, Montgomeryville, Pa.) basic vector lacks eukaryotic promoter and enhancer sequences. This allows maximum flexibility in cloning any putative regulatory sequences into the convenient multiple cloning sites. Expression of CAT activity in cells transfected with this vector is dependent on insertion of a functional promoter upstream from the CAT gene. Enhancer elements can be inserted at the BamH I site downstream from the CAT gene. The vector map sequence reference points are multiple cloning sites (Hind III-Xba I) 2242-2271, SV40 small T antigen region 3064-3917, CAT gene start site 2315, CAT gene stop site 2974, and β-lactamase (Amp') coding region 209-1069.

Plasmid DNA was diluted to 5 µg per 100 µl in HBS. The DNA and lipid mixes were combined and incubated for 45 minutes at room temperature. HeLa cells (ATCC certified cell line 2 (CCL 2)) were plated at a concentration of $4 \times 10^5$ per well in Eagle's MEM with non-essential amino acids and Earle's BSS, 90%; fetal bovine serum, 10%. 200 µl of the lipid/DNA complex were added to each well and incubated 48-72 hours in the presence of serum. The process was repeated using n-perfluorohexane in volumes of 50, 25, and 12.5 microliters. CAT expression was assayed using a CAT ELISA from Boehringer Mannheim Biochemical (Indianapolis, Ind.). The results are shown in Table 7.

tion of $1 \times 10^5$ per well. NIH3T3 cells (ATCC cell repository line 1658 (CRL 1658)) were propagated in Dulbecco's modified Eagle's medium with 4.5 g/liter glucose, 90% and calf serum, 10% and plated at a concentration of $1 \times 10^5$ per well. C127:LT cells (ATCC cell repository line 1804 (CRL 1804)) were propagated in Dulbecco's modified Eagle's medium with 4.5 g/liter glucose, 90% and fetal bovine serum, 10% and plated at a concentration of $1 \times 10^5$ per well. DPEPC:DOPE was prepared with perfluorohexane at a volume of 12.5 microliters and without perfluorohexane as Example 10. The lipid/DNA mixtures were incubated with the cells for 72 hours as described in Example 10. Lipofectin and Lipofectamine (Life Technologies, Gaithersburg, Md.), commer-

TABLE 7

Effect of Various Amount of Organic Halide on Chloramphenical Transacetylase Expression in Various Cell Lines

| Lipids | Organic Halide (OH) | OH Volume µl | Cell Line | CAT Expression | Standard Deviation |
|---|---|---|---|---|---|
| Lipofectin | None | | HeLa | 59.624 | 6.828 |
| Lipofectamine | None | | HeLa | 27.917 | 5.112 |
| Lipofectin | None | | C127 | 0 | 1.582 |
| Lipofectamine | None | | C127 | 0 | 3.164 |
| Lipofectin | None | | COS1 | 104.424 | 117.883 |
| Lipofectamine | None | | COS1 | 305.392 | 23.254 |
| Lipofectin | None | | NIH3t3 | 0 | 1.582 |
| Lipofectamine | None | | NIH3t3 | 5.766 | 8.809 |
| DPEPC/DOPE | None | | HeLa | 28.946 | 11.852 |
| DPEPC/DOPE | None | | C127 | 24.493 | 21.491 |
| DPEPC/DOPE | None | | COS1 | 4930.403 | 262.278 |
| DPEPC/DOPE | None | | NIH3t3 | 36.368 | 21.952 |
| DPEPC/DOPE | Perfluorohexane | 12.5 | HeLa | 3642.958 | 229.17 |
| DPEPC/DOPE | Perfluorohexane | 25 | HeLa | 126.976 | 19.126 |
| DPEPC/DOPE | Perfluorohexane | 50 | HeLa | 33.454 | 10.94 |
| DPEPC/DOPE | Perfluorohexane | 100 | HeLa | 28.69 | 2.61 |
| DPEPC/DOPE | Bromononafluorobutane | 12.5 | HeLa | 1795.29 | 1054.14 |
| DPEPC/DOPE | Bromononafluorobutane | 25 | HeLa | 2725.611 | 1004.542 |
| DPEPC/DOPE | Bromononafluorobutane | 50 | HeLa | 2634.161 | 456.709 |
| DPEPC/DOPE | Bromononafluorobutane | 100 | HeLa | 2703.144 | 600.767 |
| DPEPC/DOPE | Perfluorohexane | 12.5 | C127 | 167.911 | 88.724 |
| DPEPC/DOPE | Perfluorohexane | 12.5 | COS1 | 5348.326 | 93.809 |
| DPEPC/DOPE | Perfluorohexane | 12.5 | NIH3t3 | 1968.405 | 316.894 |

*DPEPC/DOPE is dipalmitoylethylphosphatidylcholine: dioleylphosphatidylethanolamine;
CAT expression units are ng/ml (protein).

Example 11

Transfection Efficiency of DPEPC with Organic Halides

An example of transfection of DPEPC with perfluorohexane and 1-bromononafluorobutane (BNFB, Fluoroseal, Houston, Tex.) was carried out. Particles were prepared as set forth in Example 10 except that the BNFB sample was cooled before and after shaking on the Wig-L-Bug to keep the BNFB in the liquid state. The results are shown in Table 7.

Example 12

Improved Transfection in Cell Lines Normally Resistant to Transfection with Perfluorohexane COS-1 cells (ATCC cell repository line 1650 (CRL 1650)) were propagated in Dulbecco's modified Eagle's medium, 90% and fetal bovine serum, 10% and plated at a concentracially available controls, were used according to the manufacturer's instructions. The results are shown in Table 7.

Example 13

Transfection Using Cationic Microspheres Filled with Perfluorobutane Gas

A lipid solution with 1 mg per ml of lipid composed of 1:1 (w:w) DPEPC with dipalmitoylphosphatidylethanolamine (DPPE) was prepared and placed in a 2 ml vial with a head space of perfluorobutane gas. The samples were shaken for 1 minute of an ESPE CapMix at 4500 RPM resulting in gas filled lipid coated microspheres. To each sample pCMVCAT was added at a DNA concentration of 1 µg per 6 µg lipid. The process was repeated using 1:1 w:w DPEPC with DOPE. The gas filled microspheres prepared from DPEPC/DPPE (gel state saturated lipids) formed stable gas filled microspheres binding the DNA. When transfection experiments were repeated substantially as outlined in Example 11, however, there was no evidence of any appreciable gene expression. When gas filled microspheres were prepared from the DPEPC/DOPE lipids (DOPE is liquid crystalline state at physiologically relevant temperature) the particle count was lower than for the DPEPC/DPPE vesicles. When DNA was added to the lipids, the vesicles fell apart, indicating how cationic lipid microspheres composed of liquid crystalline state lipid are unstable to bind DNA when the interior of the microsphere is filled with a gas PFC (perfluorobutane) as opposed to a liquid PFC (see above).

Example 14

Transfection with Organic Halides

The experiment conducted in Example 12 was repeated except that fluorinated organic halides were used in eight samples and eight samples were subjected to ultrasound. Sixty minutes following the incubation of the DNA/lipid complex with the cells, ultrasound was applied by immersing the head of a 1 Mz transducer directly to the top of the cell culture well and ultrasound was applied for 5 to 30 seconds at a 10% duty cycle. Control groups were cells not exposed to ultrasound with and without transfection materials. Table 8 indicates that organic halides increase the efficiency of ultrasound such that lower levels of energy are more effective. 1-bromononafluorobutane (BNFB) together with ultrasound results in about a 50% enhancement of expression; whereas about a 30% enhancement of expression is evident with perfluorohexane (PFC6) and ultrasound.

TABLE 8

| Lipids | OH | US (sec.) | Expression Actual | SD |
|---|---|---|---|---|
| DPEPC/DOPE | BNFB | 0 | 7007 | 2084 |
| DPEPC/DOPE | BNFB | 5 | 10442 | 610 |
| DPEPC/DOPE | BNFB | 15 | 9910 | 656 |
| DPEPC/DOPE | BNFB | 30 | 9381 | 140 |
| none | — | 0 | −137 | 23 |
| DPEPC/DOPE | — | 0 | 1647 | 396 |
| DPEPC/DOPE | — | 5 | 6444 | 846 |
| DPEPC/DOPE | — | 30 | 8167 | 1206 |
| Lipofectamine | — | 0 | 389 | 125 |
| Lipofectin | — | 0 | −118 | 14 |
| DPEPC/DOPE | PFC6 | 0 | 7290 | 2235 |
| DPEPC/DOPE | PFC6 | 5 | 9477 | 1017 |
| DPEPC/DOPE | PFC6 | 15 | 8545 | 401 |
| DPEPC/DOPE | PFC6 | 30 | 9630 | 827 |

In all cases above the cell line is NIH/3T3. Units of DNA expression are ng/ml protein. Ultrasound was applied at 0.5 W/cm$^2$, 10% duty cycle. OH-organic halide, US (sec.)—ultrasound in seconds, BNFB—(1-bromonanofluorobutane), PFC6—(perfluorohexane), SD—standard deviation.

As can be seen above the lipid mixture of DPEPC/DOPE carrying the gene results in above background expression compared to Lipofectin or Lipofectamine. This expression is enhanced with the addition of either a fluorocarbon or by ultrasound. The best results were obtained with fluorocarbons and ultrasound in combination.

Example 15

Transfection with Perfluoroethers

The experiment described in Example 10 was repeated with the following perfluoroethers: perfluoromethylbutyl ether (PFMBE), perfluoro-4-methyl-tetrahydrofuran (PMTH) and perfluorotetrahydropyran (PFTH). Transfection data is shown in Table 9 below. Table 9 shows that perfluoroethers perform similar to perfluorocarbons of the previous examples. Increased levels of perfluoroethers do not appear to have a detrimental effect on transfection and expression. Each of the perfluoroethers enhance transfection greater than 100% over the control lipid (DODO).

TABLE 9

| Lipids | Perfluoroether | PFE (vol) | CAT expression | Std. Dev. |
|---|---|---|---|---|
| (none) | none | — | −54.773 | 4.957 |
| DODO | none | — | 1490.801 | 183.278 |
| DODO | PFMBE | 0.125 mls | 3578.363 | 55.702 |
| DODO | PFMBE | 0.250 mls | 3167.014 | 246.912 |
| DODO | PFMBE | 0.500 mls | 3509.693 | 109.497 |
| DODO | PFMTH | 0.250 mls | 3424.945 | 25.837 |
| DODO | PFMTH | 0.500 mls | 3373.024 | 36.736 |
| DODO | PFTH | 0.250 mls | 3306.029 | 67.332 |
| DODO | PFTH | 0.500 mls | 3344.886 | 235.041 |

In all cases above the cell line is HeLa, and the lipid coating for the perfluoroether dioleyl-glycero-3 phosphocholine. CAT expression units are ng/ml protein. Std. dev.—standard deviation, PFE (vol)—perfluoroether in volume.

Example 16

Transfection Efficiency with Perfluorohexane

The experiment of Example 10 was repeated in HeLa cells using DMRIE-C, DODO, DPDO, or other commercial cationic lipids with and without perfluorohexane. The results are shown in Table 10 below. Table 10 shows that perfluorocarbons are effective with a variety of lipids. Indeed, the enhancement of expression is independent of the type of lipid used. DODO+PFC6 results in about 8 to about 10 fold increase in expression, DMRIE-C results in about a 40% enhancement of expression, and DPDO results in about a 4 fold increase.

TABLE 10

| Lipids | PFC | PFC (vol) | CAT expression | Std. Dev. |
|---|---|---|---|---|
| (none) | none | — | −5.608 | 5.015 |
| DMRIE-C | none | — | 1615.096 | 79.088 |
| DMRIE-C | PFC6 | 0.125 mls | 2118.489 | 72.325 |
| DODO | none | — | 611.594 | 228.548 |
| DODO | PFC6 | 0.250 mls | 6331.664 | 443.727 |
| DODO | PFC6 | 0.500 mls | 4829.148 | 379.244 |
| DPDO | none | — | 426.652 | 238.019 |
| DPDO | PFC6 | 0.125 mls | 1675.285 | 1146.279 |
| Lipofectamine | none | — | −8.891 | 1.895 |
| Lipofectin | none | — | 100.542 | 56.863 |

DODO—dioleyl-glycero-3 phosphoethylcholine. CAT expression units are ng/ml protein. DPDO—dipalmitoyl-glycero-3 phosphocholine, Std. Dev.—standard deviation, PFC (vol)—perfluorocarbon in volume.

Example 17

Effect of Ultrasound Alone on DMRIE and DODO Vesicle Transfection

The experiments described above in the previous examples were repeated using the DMRIE, DODO, and no lipids, in each case without an organic halide, using the same procedures set forth above in Example 16.

TABLE 11

| Lipids | OH | US (sec.) | Expression Actual | SD |
|---|---|---|---|---|
| none | none | 0 | 76 | 4 |
| DMRIE | none | 0 | 426 | 49 |
| DMRIE | none | 5 | 1450 | 317 |
| DMRIE | none | 30 | 1204 | 120 |
| DODO | none | 0 | 2719 | 102 |
| DODO | none | 5 | 4073 | 61 |
| DODO | none | 30 | 3914 | 53 |

In all cases above the cell line is HeLa. Units of DNA expression are ng/ml protein. Ultrasound was applied at 0.5 W/cm$^2$, 10% duty cycle. OH—organic halide, PFC—perfluorocarbon, US (sec.)—ultrasound in seconds, SD—standard deviation.

Example 18

Effect of Poly-L-Lysine (in Place of Lipids) on Transfection with Perfluorohexane The experiments described above in the previous examples were repeated using the DODO with or without a fluorinated organic halide, Poly-L-Lys with or without a fluorinated organic halide, and no lipids and no organic halide, using the same procedures set forth above in Example 16.

TABLE 12

| Carrier | OH | OH (vol) | CAT expression | Std. Dev. |
|---|---|---|---|---|
| (none) | none | — | 1.378 | 1.012 |
| DODO | none | — | 2190.158 | 684.125 |
| DODO | PFC6 | 0.125 | 3322.927 | 39.520 |
| Poly-L-Lys | none | — | 37.901 | 2.072 |
| Poly-L-Lys | PFC6 | 0.125 | 50.909 | 5.128 |

DODO—dioleyl-glycero-3 phosphoethylcholine. CAT expression units are ng/ml protein. OH—organic halide, OH (vol)—organic halide in volume in mls, Std. Dev.—standard deviation.

Example 19

Comparison of Different Organic Halides as Transfection Enhancers

The experiment was carried out as in Example 10 using HeLa cells, dioleyl-glycero-3-phosphoethanolamine (DOPE) as the lipid carrier and either perfluoropentane (PFC$_5$), 1-bromoperfluorooctane (perfluoro-octylbromide, BrPFC$_8$), perfluorodecane (PFC$_{10}$) or perfluorohexane (PFC$_6$). The Table 13 illustrates the transfection results.

TABLE 13

| Lipids | OH | OH vol (in mls) | CAT expression | Std. Dev. |
|---|---|---|---|---|
| (none) | none | — | −11.434 | 1.478 |
| DOPE | none | — | 295.447 | 18.828 |
| DOPE | PFC5 | 0.125 | 1204.762 | 198.020 |
| DOPE | PFC5 | 0.250 | 900.344 | 247.634 |
| DOPE | PFC5 | 0.500 | 1089.989 | 245.888 |
| DOPE | BrPFC8 | 0.125 | 276.236 | 57.468 |
| DOPE | BrPFC8 | 0.250 | 248.652 | 26.723 |

TABLE 13-continued

| Lipids | OH | OH vol (in mls) | CAT expression | Std. Dev. |
|---|---|---|---|---|
| DOPE | BrPFC8 | 0.500 | 114.175 | 65.473 |
| DOPE | PFC10 | 0.125 | 839.263 | 302.202 |
| DOPE | PFC10 | 0.250 | 811.678 | 171.344 |
| DOPE | PFC10 | 0.500 | 1186.044 | 322.248 |
| DOPE | PFC6 | 0.125 | 1108.215 | 164.989 |
| DOPE | PFC6 | 0.250 | 829.904 | 156.464 |
| DOPE | PFC6 | 0.500 | 441.745 | 33.219 |

OH—organic halide,
OH (vol)—organic halide in volume,
Std. Dev.—standard deviation.

The above results indicate that liquid (perfluorohexane or perfluorodecane) perfluorocarbons work as well as perfluorocarbons which would undergo at least a partial liquid to gas phase transition at physiological temperatures (perfluoropentane). Only the brominated compound, BrPFC$_8$, was markedly less effective in enhancing transduction.

The data also indicate that a preferred quantity of perfluorocarbon for transfection generally is in the range of 0.125 mls to 0.250 mls or from about 1% to 3% v/v.

Example 20

Transfection in the Presence of Fluorinated Surfactants

The experiment described in Example 10 is repeated except the lipids are suspended in varying amounts (1.25% to 5%) of Zonyl® surfactant, (Du Pont Chemical Co., Wilmington, Del.). In some samples perfluorohexane (0.125 mls, 0.250 mls or 0.500 mls) is shaken with the surfactant. The sizes range from about 300 nm to about 900 nm. Transfection efficiency where samples are prepared from Zonyl® is about 10% to about 25% of the transfection where samples are prepared without Zonyl®.

Example 21

Transfection with Cationic Lipid Carrier and Lipid Suspension with Organic Halides and with and without Ultrasound The experiment described in Example 14 is modified such that the control lipid mixture is DPPC/DPPA/PEG-5000+ perfluoropropane and results are compared to transfection using a suspension of the cationic lipid DOTMA+perfluoropropane. After incubation ultrasound is applied as in Example 14 to some of the samples. Results similar to those obtained in Example 14 are observed.

Example 22

Transfection with Cationic Lipid Carrier and Lipid Suspension with Ultrasound and 1-Bromononafluorobutane Cationic liposomes are prepared from dioleyolyethylphosphocholine and DOPE at a concentration of 1 mg/ml lipid. To this is added 0.125 μl 1-bromo-nonafluorobutane (BNFB). The mixture is agitated with a Wig-L-Bug for 60 seconds and the resulting vesicles are extruded with a 0.8 micron filter. The resulting BNFB filled cationic liposomes are then complexed with ribozymal RNA (hammerhead motif) encoding catalytic RNA specific for vascular endothelial growth factor (VEGF) at a lipid to RNA ratio of 1:6 using conventional methods. The liposomal RNA preparation (1.0 ml) is injected IV into a patient with diabetic retinopathy. A 5 megahertz ultrasound transducer is placed on the patient's anesthetized cornea using a silicone acoustic coupling gel. Ultrasound energy is focused onto the patient's retina using 2.0 Watts and a 10% duty cycle. As the liposomes enter the region of ultrasound the gaseous precursor expands and pulsates. Local shock waves are created. The ribozyme RNA is delivered to the endothelial cells in the region of ultrasound application the therapeutic RNA construct enters the target endothelial cells. Catalytic RNA then causes reduction in VEGF production. The patient's retinal deterioration is halted and blindness is avoided.

Example 23

In Vivo Transfection Using Perfluorocarbons

Liposomes were prepared from dipalmitoylethylphosphocholine (DPEPC) and dioleoylphosphatidylethanolamine (DOPE). Both lipids were purchased from Avanti Polar Lipids (Alabaster, Ala.). Lipofectin® and Lipofectamine® and DMRIE-C® were obtained in a ready to use form from Life Technologies Inc. (Gaithersburg, Md.). Plasmid pCMVCAT which contains the human cytomegalovirus promoter and the chloramphenicol acetyl transferase gene was provided by Life Technologies (Gaithersburg, Md.). Plasmid DNA was prepared by large scale extraction from E. coli and purified by CsCl banding by Lofstrand Labs Limited (Gaithersburg, Md.). In a preliminary set of experiments the ratios of the two lipids as well as the ratio of lipid to DNA was optimized by measuring the levels of gene expression in HeLa cells following transfection with the pCMVCAT plasmid using DPEPC/DOPE in a ratio of 1:1, with a lipid to DNA ratio of 6:1 (the lipid and DNA combination collectively being referred to as DPDO). The liposomes were prepared by suspending the dried lipids in water and lyophilizing the mixed lipids and resuspending the lipids in water. The rehydrated lipids were agitated at about 2,000 r.p.m. on a dental amalgamator (Heavy duty #6 Wig-L-Bug Crescent Dental, Lyons, Ill.) for 5 minutes and then extruded through two 0.8 micron polycarbonate filters (Nucleopore Costar, Cambridge, Mass.) using an Extruder Device (Lipex Biomembranes, Vancouver, B.C., Canada) at about 30 psi. For preparation of perfluorocarbon (PFC) filled liposomes, 100 microliters, 50, 25 or 12.5 microliters of PFC was added to the lipid solution prior to shaking on the dental amalgamator. PFC's which were tested included perfluoropentane, perfluorohexane, 1-bromononafluorobutane, perfluorooctylbromide and perfluoromethylbutylether.

In vivo experiments were carried out in 50 male Balb/C mice. The body weight of the mice was 15-20 g. The lipoplex was formed in the same manner as for cell transfection using the DPEPC/DOPE lipid mixture. The perfluorocarbon used in this experiment was perfluorohexane. The mixture was injected intramuscularly at a does of 200 µl per hind leg. The ultrasound (US) was applied at 1 W/cm² for one minute to each leg in the animals that received ultrasound. The animals were held for 2 days and then euthanized by carbon dioxide asphyxiation. The hind legs were removed from the animals and the muscle collected. The muscle was frozen in liquid nitrogen and ground in a mortar and pestle. The tissue was transferred to a pre-weighed 50 ml conical tube and the tissue weight was recorded. The tissue was then placed into one ml of the lysis buffer from the CAT ELISA kit. The CAT ELISA was then carried out according to the manufacturer's protocol. The data was transferred into Microsoft Excel and converted into ng CAT protein per gram of tissue. Statistical analysis was carried out using the JMP 3.1.5 statistical analysis package for the Macintosh.

Figure 7:
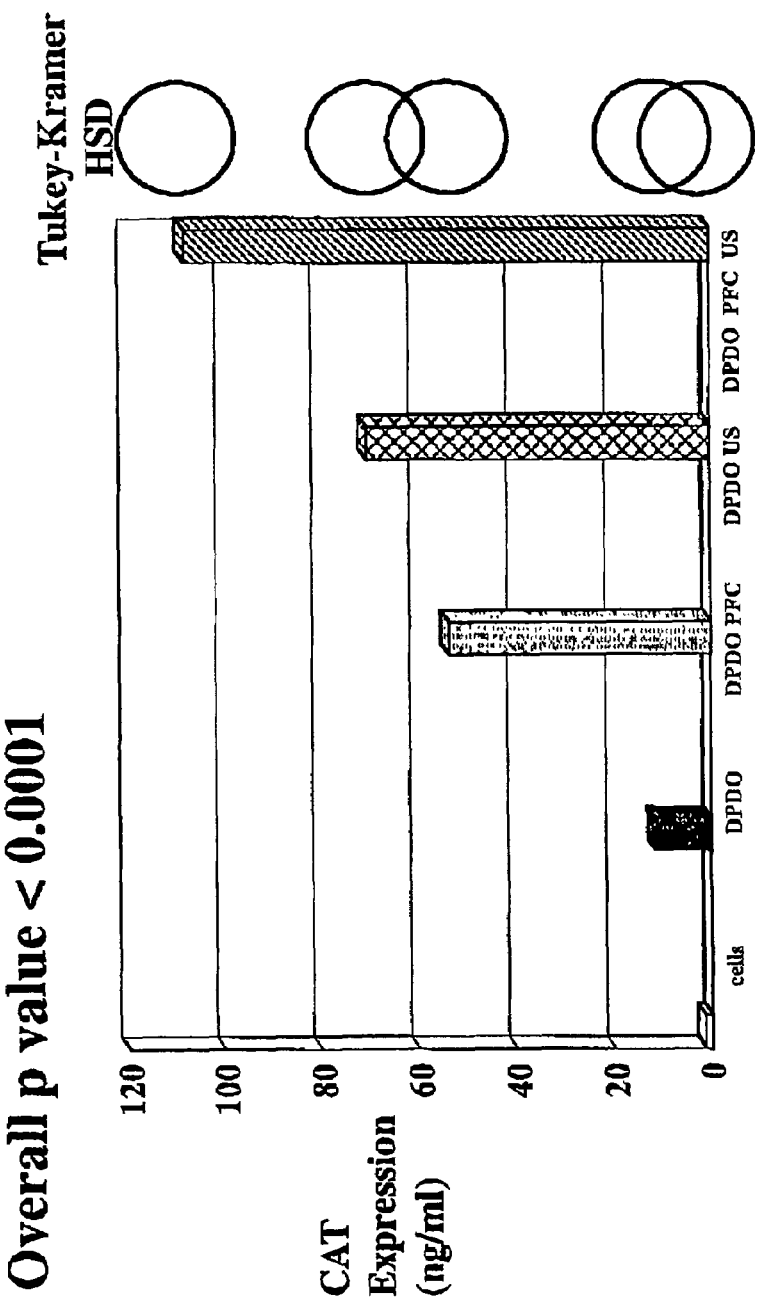
FIG. 7 depicts the results of the in vivo transfection studies in mice set forth in Example 23.

The results are shown in FIG. 7. As the figure shows, the use of a perfluorocarbon (with or without ultrasound) greatly enhanced CAT expression in mice.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method for delivering a protein into a cell in vivo, comprising:
    (a) forming a plurality of protein-halide vesicles comprising the protein to be delivered and an organic halide incorporated in the core of the vesicles; and
    (b) administering the protein-halide vesicles to the cell, wherein the organic halide is selected from the group consisting of 1-bromo-nonafluorobutane, perfluorooctyliodide, perfluoroocytlbromide, 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1-bromoperfluorobutane, 2-iodo-1,1,1-trifluoroethane, 5-bromovaleryl chloride, 1,3-dichlorotetrafluoroacetone, 1-bromo-1,1,2,3,3,3-hexafluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, heptafluoro-2-iodopropane, bromotrifluoroethane, chlorotrifluoromethane, dibromofluoromethane, chloropentafluoroethane, bromochlorodifluoromethane, dichloro-1,1,2,2-tetrafluoroethane, 1,1,1,3,3-pentafluoropentane, perfluorotributylamine, perfluorotripropylamine, 2,2,2-trifluoroethylacrylate, 3-(trifluoromethoxy)-acetophenone, 1,1,2,2,3,3,4,4-octafluorobutane, 1,1,1,3,3-pentafluorobutane, 1-fluorobutane, 1,1,2,2,3,3,4,4-octafluorobutane, 1,1,1,3,3-pentafluorobutane, tetradecaperfluoroheptane, dodecaperfluorocyclohexane, perfluoromethane, perfluoroethane, perfluoropropane, perfluorobutane, perfluoropentane, perfluorohexane, perfluoroheptane, perfluorooctane, perfluorononane, perfluorodecane, perfluorododecane, perfluoro-2-methyl-2-pentene, perfluorocyclohexane, perfluoropropylene, perfluorocyclobutane, perfluoro-2-butyne, perfluoro-2-butene, perfluorobuta-1,3-diene, perfluorobutylethyl ether, bis (perfluoroisopropyl) ether, bis(perfluoropropyl) ether, perfluoromethyl tetrahydrofuran, perfluoro t-butyl methyl ether, perfluoro isobutyl methyl ether; perfluoro n-butyl methyl ether, perfluoro isopropyl ethyl ether, perfluoro n-propyl ethyl ether, perfluoro cyclobutyl methyl ether, perfluoro cyclopropyl ethyl ether, perfluoro isopropyl methyl ether, perfluoro n-propyl methyl ether, perfluoro diethyl ether, perfluoro cyclopropyl methyl ether, perfluoro methyl ethyl ether, and perfluoro dimethyl ether,
    wherein the path of administering of the protein-halide composition to the cell is selected from a group consisting of the administering through a cell membrane, cell wall, and nuclear membrane, or any combination thereof,
    to achieve the intracellular delivery of the protein thereby.

2. The method of claim 1, wherein the organic halide is selected from the group consisting of 1-bromo-nonafluorobutane, 1,1,1,3,3-pentafluoropentane, perfluorohexane, perfluorocyclohexane, 1-bromo-1,1,2,3,3,3-hexafluoropropane, heptafluoro-2-iodopropane, 1,1,2,2,3,3,4,4-octafluorobutane, 1-fluorobutane, tetradecaperfluoroheptane, and dodecaperfluorocyclohexane.

3. The method of claim 1, wherein the organic halide is selected from the group consisting of perfluorohexane and perfluorocyclohexane.

4. The method of claim 1, wherein the protein is selected from the group consisting of albumin, collagen, polyarginine, polylysine, polyhistidine, γ-globulin, and β-globulin.

5. The method of claim 1, wherein the protein is a cationic protein.

6. The method of claim 5, wherein the cationic protein is selected from the group consisting of polylysine and polyethyleneimine.

7. The method of claim 1, further comprising applying ultrasound to the cell.

8. The method of claim 7, wherein the ultrasound is applied at a frequency between about 40 kHz and 25 MHz, and an energy level between about 500 mW/cm$^2$ and 10 W/cm$^2$.

9. The method of claim 7, wherein the ultrasound is applied at a frequency between about 200 kHz and 500 kHz, and the energy level is between about 200 mW/cm$^2$ and 500 W/cm$^2$.

10. The method of claim 7, wherein the ultrasound is applied at a frequency between about 1 MHz and 20 MHz, and the energy level is between about 100 W/cm$^2$ and 200 W/cm$^2$.

11. The method of claim 10, wherein the ultrasound is applied at a duty cycle between about 1% and 100% of the treatment time.

12. The method of claim 7, wherein the protein and the ultrasound are administered and applied simultaneously.

* * * * *

UNITED STATES PATENT AND TRADEMARK OFFICE
CERTIFICATE OF CORRECTION

PATENT NO. : 7,612,033 B2
APPLICATION NO. : 10/802919
DATED : November 3, 2009
INVENTOR(S) : Unger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 772 days.

Signed and Sealed this

Fourteenth Day of December, 2010

David J. Kappos
*Director of the United States Patent and Trademark Office*